(12) United States Patent
Benamou et al.

(10) Patent No.: US 11,937,843 B2
(45) Date of Patent: Mar. 26, 2024

(54) ARTHROSCOPIC DEVICES AND METHODS

(71) Applicant: Relign Corporation, Campbell, CA (US)

(72) Inventors: Steffan Benamou, Morgan Hill, CA (US); Michael D Walker, San Francisco, CA (US); Aaron Germain, San Jose, CA (US)

(73) Assignee: Relign Corporation, Campbell, CA (US)

( * ) Notice: Subject to any disclaimer, the term of this patent is extended or adjusted under 35 U.S.C. 154(b) by 358 days.

(21) Appl. No.: 17/494,970

(22) Filed: Oct. 6, 2021

(65) Prior Publication Data
US 2022/0022908 A1    Jan. 27, 2022

Related U.S. Application Data

(63) Continuation of application No. 15/920,258, filed on Mar. 13, 2018, now Pat. No. 11,207,092.
(Continued)

(51) Int. Cl.
*A61B 17/32* (2006.01)
*A61B 17/00* (2006.01)
(Continued)

(52) U.S. Cl.
CPC .... *A61B 17/32002* (2013.01); *A61B 17/1615* (2013.01); *A61B 18/148* (2013.01);
(Continued)

(58) Field of Classification Search
CPC ........... A61B 2017/00039; A61B 2017/00269; A61B 2017/00274; A61B 2017/00367;
(Continued)

(56) References Cited

U.S. PATENT DOCUMENTS 5,672,945 A   9/1997 Krause
6,149,620 A   11/2000 Baker et al.
(Continued)

FOREIGN PATENT DOCUMENTS

CN    110678135 A    1/2020
EP    3600099 A1     2/2020
(Continued)

OTHER PUBLICATIONS

"U.S. Appl. No. 15/920,258, Advisory Action dated Mar. 2, 2021", 3 pgs.
(Continued)

*Primary Examiner* — Ronald Hupczey, Jr.
*Assistant Examiner* — Bradford C. Blaise
(74) *Attorney, Agent, or Firm* — SCHWEGMAN LUNDBERG & WOESSNER, P.A.

(57) ABSTRACT

An electrosurgical probe includes an elongated shaft assembly having a proximal end, a distal end, and a longitudinal axis. A distal housing is mounted on the distal end of the shaft and optionally includes a laterally open window where a plane of the window is generally perpendicular to the longitudinal axis of the shaft. An interior channel extends axially through the shaft and further through an interior of the housing to the window in the housing. An electrode member with a serrated or other elongated edge may extend longitudinally across the window and may be configured to reciprocate the elongated edge longitudinally relative to the window.

21 Claims, 33 Drawing Sheets

Related U.S. Application Data

(60) Provisional application No. 62/477,313, filed on Mar. 27, 2017.

(51) Int. Cl.
*A61B 17/16* (2006.01)
*A61B 17/30* (2006.01)
*A61B 18/00* (2006.01)
*A61B 18/14* (2006.01)
*A61B 90/00* (2016.01)

(52) U.S. Cl.
CPC ............ *A61B 2017/00039* (2013.01); *A61B 2017/00075* (2013.01); *A61B 2017/00398* (2013.01); *A61B 2017/0088* (2013.01); *A61B 2017/306* (2013.01); *A61B 17/320016* (2013.01); *A61B 2017/320024* (2013.01); *A61B 2017/320028* (2013.01); *A61B 2017/320032* (2013.01); *A61B 2018/00196* (2013.01); *A61B 2018/00202* (2013.01); *A61B 2018/00208* (2013.01); *A61B 2018/00565* (2013.01); *A61B 2018/00577* (2013.01); *A61B 2018/00601* (2013.01); *A61B 2018/00982* (2013.01); *A61B 2018/1422* (2013.01); *A61B 2018/144* (2013.01); *A61B 2090/067* (2016.02); *A61B 2217/005* (2013.01); *A61B 2218/007* (2013.01)

(58) Field of Classification Search
CPC .. A61B 2017/00398; A61B 2017/0088; A61B 17/320016; A61B 17/32002; A61B 17/320036; A61B 17/320783; A61B 17/320791; A61B 2017/320024; A61B 2017/320028; A61B 2017/320032; A61B 2017/32004; A61B 2018/00166; A61B 2018/00184; A61B 2018/00196; A61B 2018/00202; A61B 2018/00208; A61B 2018/00607; A61B 2018/0091; A61B 2018/00982; A61B 2018/1475; A61B 18/148; A61B 18/1482; A61B 18/149; A61B 2218/001; A61B 2218/002; A61B 2218/007; A61B 2217/005
See application file for complete search history.

(56) References Cited

U.S. PATENT DOCUMENTS

| | | |
|---|---|---|
| 7,678,069 B1 | 3/2010 | Baker et al. |
| 2008/0188848 A1 | 8/2008 | Deutmeyer et al. |
| 2011/0196400 A1 | 8/2011 | Robertson et al. |
| 2012/0330307 A1 | 12/2012 | Ladtkow et al. |
| 2013/0085498 A1 | 4/2013 | Matusaitis et al. |
| 2013/0253498 A1 | 9/2013 | Germain et al. |
| 2014/0100567 A1 | 4/2014 | Edwards et al. |
| 2014/0263538 A1 | 9/2014 | Leimbach et al. |
| 2014/0336643 A1 | 11/2014 | Orczy-timko et al. |
| 2015/0105791 A1 | 4/2015 | Truckai |
| 2016/0081737 A1 | 3/2016 | Germain et al. |
| 2016/0113706 A1 | 4/2016 | Truckai et al. |
| 2016/0157916 A1 | 6/2016 | Germain et al. |
| 2016/0346036 A1 | 12/2016 | Orczy-timko et al. |
| 2017/0224368 A1 | 8/2017 | Germain et al. |
| 2019/0083121 A1 | 3/2019 | Benamou et al. |

FOREIGN PATENT DOCUMENTS

| | | |
|---|---|---|
| JP | 2020512147 A | 4/2020 |
| WO | WO-2016171963 A1 | 10/2016 |
| WO | WO-2018183002 A1 | 10/2018 |

OTHER PUBLICATIONS

"U.S. Appl. No. 15/920,258, Final Office Action dated Dec. 31, 2020", 18 pgs.

"U.S. Appl. No. 15/920,258, Non Final Office Action dated Apr. 30, 2020", 20 pgs.

"U.S. Appl. No. 15/920,258, Notice of Allowance dated Aug. 19, 2021", 12 pgs.

"U.S. Appl. No. 15/920,258, Response filed Feb. 22, 2021 to Final Office Action dated Dec. 31, 2020", 11 pgs.

"U.S. Appl. No. 15/920,258, Response filed May 27, 2021 to Advisory Action mailed Mar. 2, 2021", 7 pgs.

"U.S. Appl. No. 15/920,258, Response filed Oct. 21, 2020 to Non Final Office Action dated Apr. 30, 2020", 8 pgs.

"European Application Serial No. 18775016.1, Extended European Search Report dated Nov. 23, 2020", 8 pgs.

"European Application Serial No. 18775016.1, Response filed Jun. 21, 2021 to Extended European Search Report dated Nov. 23, 2020", 14 pgs.

"International Application Serial No. PCT/US2018/022952, International Preliminary Report on Patentability dated Oct. 10, 2019", 8 pgs.

"International Application Serial No. PCT/US2018/022952, International Search Report dated Jun. 6, 2018", 2 pgs.

"International Application Serial No. PCT/US2018/022952, Written Opinion dated Jun. 6, 2018", 6 pgs.

ARTHROSCOPIC DEVICES AND METHODS

CROSS-REFERENCE TO RELATED APPLICATION

The present application is a continuation of U.S. patent application Ser. No. 15/920,258, filed Mar. 13, 2018 (and issued as U.S. Pat. No. 11,207,092 B2 on Dec. 28, 2021), which claims the benefit of Provisional Application 62/477,313, filed on Mar. 27, 2017, the full disclosure of which is incorporated herein by reference.

BACKGROUND OF THE INVENTION

1. Field of the Invention

This invention relates to arthroscopic tissue cutting and ablation devices by which anatomical tissues may be resected, ablated and removed from a joint or other site. More specifically, this invention relates to electrosurgical probes and methods for ablating and removing soft tissue.

In many arthroscopic procedures including subacromial decompression, anterior cruciate ligament reconstruction, and resection of the acromioclavicular joint, there is a need for cutting and removing and soft tissue. Currently, surgeons use arthroscopic shavers having rotational cutting surfaces to remove soft tissue in such procedures.

The need exists for arthroscopic instrument that remove soft tissue rapidly. Recently, arthroscopic surgical cutters capable of selectively removing both hard tissues and soft tissues have been developed. Such cutters are described in the following US Patent Publications which are commonly assigned with the present application: US20130253498; US20160113706; US20160346036; US20160157916; and US20160081737, the full disclosures of which are incorporated herein by reference.

While very effective, it would be desirable to provide arthroscopic surgical cutters and cutter systems as "reposable" devices with disposable cutting components and reusable, sterilizable handles. Preferably, the handles would incorporate as many of the high value system components as possible. Further preferably, the handle designs would have a minimum number of external connections to simplify sterilization and set-up. Still more preferably, the cutters and systems would allow for bipolar cutting as well as monopolar and mechanical (cutting blade) resection. In particular, it would be desirable to provide arthroscopic cutters having non-rotational cutters, such as axially reciprocating cutters and RF cutting wires, and cutters that can also operate in an ablation mode. At least some of these objectives will be met by the inventions described herein.

2. Description of the Background Art

U.S. Pat. Nos. 6,149,620 and 7,678,069 describe tools for the volumetric removal of soft tissue in the knee and elsewhere. Co-pending, commonly owned U.S. patent application Ser. No. 15/421,264, filed on Jan. 31, 2017, describes a tissue removal device which can remove tissue by cutting (resection) and/or by radiofrequency (RF) ablation. US 2008/0188848 describes an electrosurgical cutter with a handpiece and a removable cutter instrument. Other commonly assigned published US Patent Applications have been listed above, including US20130253498; US20160113706; US20160346036; US20160157916; and US20160081737.

SUMMARY OF THE INVENTION

The present invention provides apparatus such as electrosurgical probes. In exemplary embodiments, an electrosurgical probe comprises an elongated shaft assembly having a proximal end, a distal end, and a longitudinal axis. A distal housing is mounted on the distal end of the shaft and in one embodiment has a laterally open window, that is, a plane of the window is generally perpendicular to the longitudinal axis of the shaft. An interior channel extends axially through the shaft and extends through an interior of the housing to a window in the housing. An electrode member with an elongated edge which may be serrated extends longitudinally across the window and is configured to reciprocate the elongated edge longitudinally relative to the window.

In specific embodiments, the shaft may comprise an outer sleeve and an inner sleeve, and the distal housing may be a ceramic and is mounted on a distal end of the outer sleeve. The electrode member is mounted on a distal end of the inner sleeve, and the inner sleeve may be reciprocatably mounted in the outer sleeve. A proximal hub is attached to a proximal end of the outer sleeve and a sliding collar is coupled to a proximal end of the inner sleeve, the sliding collar being mounted and configured to axially reciprocate within the proximal hub while being restrained from rotation relative to the proximal hub. In particular examples, a rotating drive coupling is mounted to rotate in the proximal hub while being restrained from axially translating relative to the proximal hub. The rotating drive coupling can have a distal surface which engages a proximal surface on the sliding collar, and the distal and proximal surfaces may have cam surfaces or otherwise shaped so that rotation and/or rotational oscillation of the rotating coupling causes the sliding collar to axially reciprocate within the proximal hub which in turn will cause the elongate edge of the electrode member to axially reciprocate relative to the window in the distal housing.

While the dimensions and geometries of the probe are usually not critical, in specific designs, the electrode member may reciprocate with a stroke in a range from 0.01 mm and 10 mm, often being in a range between 0.1 mm and 5 mm. The elongate edge may be substantially flush with the circumference of the distance housing. Further, the electrode edges may be configured to extend over edges or the window during reciprocation.

The electrosurgical probes of the present invention may further comprise a handpiece and motor drive operatively coupled to the shaft and configured to axially reciprocate the electrode at high speed relative to the window to provide a method of dynamic ablation. Usually, a proximal hub is connected to the proximal end of the elongated shaft, and the handpiece and motor drive are detachably coupled to the proximal hub. A negative pressure source is provided for coupling through the handpiece and proximal hub to an interior channel of the shaft which communicates with the window in the distal housing. The motor drive is typically configured to axially reciprocate the electrode edge at a rate in a range from 1 Hz and 1,000 Hz.

The distal housing or tip is a ceramic and may have a variety of specific geometries, and in one embodiment is attached to the distal end of the shaft. The ceramic tip has an opening therein that typically defines a circular or flower-shaped window that communicates with an interior channel in the tip and the shaft. In specific embodiments, the reciprocating component carries an electrode member that has a L-shaped or hook geometry with an axial region extending through ceramic tip and is coupled to an elongate member disposed in the shaft and configured for reciprocation through the opening. The ceramic tip or housing may be mounted on a distal end of the outer sleeve and the hook electrode may be mounted or crimped to the distal end of the elongate member which is reciprocatably mounted in the outer sleeve.

In a broad aspect, the present invention provides a method for ablating and/or resecting, cutting or slicing tissue. The method comprises engaging an electrode protruding from the housing against a surface of the tissue. An elongate edge of an electrode member may be reciprocated longitudinally to the window in a plane perpendicular to the plane of the window, and a radiofrequency current with a cutting waveform may be applied to the electrode member to dynamically ablate tissue and generate tissue debris. A vacuum may be applied to the interior channel in the housing to aspirate the tissue debris through window.

In some embodiments, the elongate edge of the electrode member may protrude beyond the plane of the housing, while in other embodiments the edge may be flushed with or recessed into the housing circumference. The electrode member is typically reciprocated at a rate in a range from 1 Hz and 1,000 Hz, usually between 1 Hz and 500 Hz.

In a first specific aspect, the present invention provides an electrosurgical probe for use with a handpiece having a motor drive unit and a radiofrequency (RF) current contact. The probe comprises an elongate shaft having a longitudinal axis, a distal dielectric tip, and a proximal hub configured to be detachably secured to the handpiece. An RF hook electrode may be reciprocatably mounted on or in the distal dielectric tip of the elongate shaft, and an RF connector on the hub is configured to couple to the RF current contact in the handpiece when the hub is secured to the handpiece. The hub of the probe further includes a drive mechanism which is mechanically coupled to the hook electrode. The drive mechanism is configured to engage a rotational component which is part of the motor drive unit when the hub is secured to the handpiece. Typically, the rotational component will be a rotating spindle of the type commonly found on electric motors, where the spindle drives or includes a mechanical coupler configured to releasably or detachably engage and mechanically couple to the drive mechanism of the probe. The drive mechanism in the hub of the probe is configured to convert rotational motion from the rotational component of the handpiece into axial reciprocation or translation (e.g., being a rotating cam assembly) and to transmit the axial reciprocation or translation to the hook electrode, resulting in axial displacement of the hook electrode between a non-extended position and an extended position relative to the dielectric tip of the elongate shaft.

In exemplary embodiments, the drive mechanism comprises a rod, tube, or other elongate member disposed in, on, or through the elongate shaft and has a distal end attached to the hook electrode. The drive mechanism includes a device or assembly, such as a rotatable cam assembly, located in the hub to receive rotational motion from the spindle or other rotational component of the motor drive unit. The cam or other assembly converts the rotational motion into axial reciprocation which is delivered to the elongate member and subsequently transmitted through the shaft.

In further exemplary embodiments of the electrosurgical probe, the elongate member may be electrically conductive and connected to deliver RF current from the RF connector in the hub to the RF electrode. For example, the elongate member may be an electrically conductive metal rod or tube which extends the entire length of the elongate shaft to provide an electrically conductive path from the RF connector on the hub to the hook electrode. In particular embodiments, a proximal portion of the elongate member extends through a central opening in the hub and an intermediate portion of the elongate member extends through a central lumen in the shaft. The hook electrode is then reciprocatably disposed in an opening in the dielectric tip. Typically, the central lumen in the shaft is configured to be connected to a negative pressure (vacuum or suction) source, and the hub is configured to connect the central lumen to the negative pressure source.

In more specific exemplary embodiments, the shaft comprises an outer tube having a longitudinal lumen and an inner member reciprocatably received in the longitudinal lumen of the outer tube. The distal dielectric tip is typically attached to a distal end of the outer tube and will have an opening which is contiguous with the longitudinal lumen of the outer tube. The hook electrode is attached to a distal end of the inner member so that the electrode can reciprocate within the inner member relative to the outer tube.

In alternative particular embodiments, the inner member may comprise a rod, and the hook electrode may comprise a bent wire attached to a distal end of the rod. In such cases, the longitudinal lumen of the outer member is configured to be connected to a negative pressure source. Often, a distal face of the dielectric distal tip may have a recess and a notch so that a lateral end of the bent wire of the hook electrode can be retracted into the recess and notch when the hook electrode is in its non-extended position.

In still further exemplary embodiments, the shaft may have at least one interior channel, and the dielectric distal tip may have at least one flow channel. Usually, the at least one interior channel and at least one flow channel are contiguous and configured to be connected to a negative pressure source to provide a continuous suction or vacuum path therethrough. Usually, at least one flow channel will have a cross-sectional area of at least 0.001 in$^2$. The cross-sectional area of the at least one flow channel is typically configured to accommodate fluid outflows of at least 50 ml/min when the at least one interior channel and the at least one flow channel are connected to the negative pressure source. In certain embodiments, the at least one flow channel comprises a portion of an opening in the dielectric distal tip which receives the hook electrode. In other embodiments, the distal electric tip may have at least one opening to receive the hook electrode and in additional have at least one flow channel.

In still further exemplary embodiments, the distal electrode tip includes at least one opening to receive the hook electrode. The at least one opening which receives the hook electrode is usually (i) shaped with a plurality of support elements adapted or configured to support elongate member and/or (ii) includes a plurality of flow channels adapted or configured to provide fluid flow in response to suction from the negative pressure source. In such embodiments, there will typically be at least three support elements, sometimes being four or more support elements, and the dielectric tip typically comprises a ceramic material.

In a second specific aspect, the present invention provides an electrosurgical system comprising an electrosurgical probe and a handpiece configured to be detachably connected to the electrosurgical probe. The electrosurgical probe may have any of the configurations, components, and designs described previously and elsewhere herein. The handpiece will be configured to detachably connect to the hub on the electrosurgical probe, and the handpiece will include a motor drive unit which is configured to mechanically couple to the drive mechanism of the electrosurgical probe in order to longitudinally reciprocate the elongate member and hook electrode between non-extended positions and extended positions when the hub is secured to the handpiece.

In exemplary embodiments, the systems of the present invention may further comprise a controller configured to activate and de-activate (energize and de-energize), the motor drive unit in order to shift the elongate member and hook electrode between the non-extended position and the extended position relative to the dielectric trip. Usually, the controller will be further configured to deliver RF current to the electrode. The RF current may be delivered only when the electrode is in its extended position or may be delivered only when it's in the retracted condition, or still further at all times while the electrode is being reciprocated. The RF current may have a waveform selected for any known surgical purpose, for example cutting wave forms, coagulation wave forms, and the like.

In still further specific embodiments, the controller may be configured to longitudinally reciprocate the elongate member while simultaneously delivering RF current to the hook electrode. In other embodiments, the hook electrode may be further optionally configured to rotate or rotationally oscillate the hook electrode, either with or without the simultaneous delivery of RF current. More usually, however, the hook electrodes will be axially reciprocated with no rotational and/or oscillational motion.

The drive mechanism, motor drive unit, controller, and other components of the systems in the present invention may be configured to reciprocate the hook electrode over a distance in the range from 0.01 mm to 5 mm, usually between 0.1 mm and 4 mm. The controller and motor drive unit may be further configured to reciprocate the hook electrode at a rate in the range from 5 Hz to 500 Hz, usually at a rate in the range from 10 Hz to 100 Hz.

In a third specific aspect, the present invention provides methods for assembling an electrosurgical probe system. The methods comprise providing a first electrosurgical probe, providing a handpiece, and removably attaching a hub on the first electrosurgical probe to the handpiece. Attaching the hub to the probe causes mechanical attachment of a motor drive unit in the handpiece to a drive mechanism in the electrosurgical probe. The drive mechanism in the probe longitudinally reciprocates the elongate member in the probe to in turn reciprocate an RF electrode located at a distal end of the elongate member between a non-extended position and an extended position.

Removably attaching the hub on the electrosurgical probe to the first handpiece will usually also couple or otherwise connect an RF connector on the hub to the RF current contact on the first handpiecce. The assembly methods may further comprise detaching the first electrosurgical probe from the handpiece after the electrosurgical probe system has been used to treat a patient. In some cases, after the first electrosurgical probe has been removed, the hub on a second different probe can then be removably attached to the handpiece and used to treat the patient.

In a fourth aspect, the present invention provides a method for electrosurgically resecting tissue. The method comprises positioning a distal tip of a shaft having a longitudinal axis at a tissue target site. By placing the distal tip of the shaft adjacent to the target tissue and rotating a motor in the handpiece, the hook electrode can be axially reciprocated at the distal tip of the shaft. The hook electrode typically is shifted between an axially non-extended or partially extended position and an axially extended position relative to the dielectric tip. By engaging the hook electrode against the target tissue, and delivering RF current through the hook electrode to the target tissue engaged by the electrode, the tissue may be resected, ablated, coagulated, or the like.

In some specific embodiments, the motor is driven only enough to move the hook electrode to a stationary position, typically either a fully extended position or a fully retracted position. Alternatively, the motor and handpiece may be run continuously in order to effect tissue resection as the RF electrode acts as a cutting blade when the probe is advanced through tissue. In all cases, a negative pressure will usually be drawn through an interior lumen of the shaft assembly to aspirate a region around the target tissue where the resection, ablation, or the like, is being effected.

In yet an additional embodiment of the present invention, a medical system for treating tissue comprising an elongated shaft assembly, typically formed as an arthroscopic or other medical probe, having a longitudinal axis and including a first member mounted to rotate and/or axially translate relative to a second member. The first member typically has at least one default position as well as other non-default positions relative to the second member. The non-default positions are typically all relative positions of the first member relative to the second member other than the defined default positions as discussed below. The first and second members are usually concentric inner and outer tubular members as described in detail elsewhere herein. A magnet is coupled to rotate with the first member, typically being fixedly attached to the first member, and a sensor is coupled to the second member, typically being fixedly attached to the second member. The sensor is configured to sense rotation of the magnet as the first member rotates and configured produce rotational position information, and may for example be a Hall sensor as discussed elsewhere herein. A motor drive is adapted to rotate the first member relative to the second member, typically being mechanically coupled to each, and a processor is configured to receive rotational position information from the sensor and to control the motor to rotate and rotationally position the first member relative to the second member. Usually, the processor is further configured to stop rotation first member relative to the second member in response to a predetermined event and to rotate the first member to the default position of the first member relative to the second member in the event that the first member is not initially in the default position.

In specific aspects of this additional embodiment of the present invention, an electrode is mounted on or otherwise coupled to move with the first member and is positionable in a window in the second member in the default position. Alternatively, a window in the first member is positionable in a window in the second member in the default position.

In other aspects of this additional embodiment, the predetermined event includes at least one of (1) activation of the electrode. (2) actuation of a negative pressure source in communication with a lumen in the elongated shaft assembly. (3) a time interval. (4) system set up. (5) system calibration, and (6) assembly of disposable and non-disposable components of the system. For example, the predetermined event may be a time interval between 0.1 ms and 10 seconds, often being between 1 ms and 5 seconds.

In certain aspects of this additional embodiment, the processor may be further configured modulate a treatment parameter in response determining that the first member is in a non-default position. Alternatively or additionally, the processor may be configured modulate or terminate activation of the electrode, for example following modulating or terminating activation of the electrode. Further alternatively or additionally, the processor may be configured to re-activate the electrode after moving the first member to the default position. Alternatively or additionally, the processor may be configured modulate or terminate actuation of the negative pressure source, for example being configured to move the first member to the default position following the step of modulating or terminating actuation of the negative pressure source. Alternatively or additionally, the processor may be configured to re-actuate the negative pressure source after moving the first member to the default position. Alternatively or additionally, an electrode carried by the first member is positioned in a center region of the window in the second member in the default position. Alternatively or additionally, an electrode carried by the first member is positioned away from the edges of the window in the second member in the default position. Alternatively or additionally, an electrode carried by the first member is positioned at a selected rotational angle relative to said axis and the window in the second member in the default position. Alternatively or additionally, the processor an electrode carried by the first member is positioned at a selected axial position relative to said axis and an opening in the second member in the default position.

Other aspects of the present invention are described in the following numbered calluses:

Clause 1: A medical system for treating tissue, comprising a handpiece carrying a motor drive detachably coupled to disposable tool with a first member disposed within a hub fixed to a second member, wherein the motor drive is adapted to move the first member relative to the hub and second member; a first sensor in the handpiece adapted to sense a magnetic parameter of at least one magnet in the hub to indicate a first orientation or a second orientation of the hub relative to the handpiece; a second sensor in the handpiece adapted to sense a magnetic parameter of at least one magnet in the first member to indicate a position of the first member relative to the second member; and a processor configured (i) to determine if the hub is in said first orientation or said second orientation using the first sensor and (ii) to stop movement of the first member relative to the second member in a pre-selected default position using the second sensor.

Clause 2: The medical system of clause 1 wherein the default position consists of positioning an electrode carried by the first member in a pre-selected location relative a window in the second member.

Clause 3: The medical system of clause 1 wherein the default position consists of positioning a window in the first member in a pre-selected location relative a window in the second member.

Clause 4: A medical system comprising a handpiece carrying a motor drive having a shaft; a shaver blade having a hub coupled to an elongated sleeve assembly comprising an outer sleeve fixed to the hub and a rotatable inner sleeve, the hub adapted to be detachably received by a receiver of the handpiece; a drive coupling connected to the inner sleeve configured to be detachably coupled to the motor shaft; a first sensor in the handpiece adapted to sense a magnetic parameter of at least one magnet carried in the hub to indicate a first orientation or a second orientation of the hub relative to the handpiece; a second sensor in the handpiece adapted to sense a magnetic parameter of at least one magnet in the drive coupling to indicate a position of the inner sleeve relative to the outer sleeve.

Clause 5: A medical system comprising a handpiece carrying a motor drive having a shaft; a shaver blade having a hub coupled to an elongated sleeve assembly extending along a central axis, the sleeve assembly comprising an outer sleeve fixed to the hub and a rotatable inner sleeve; a drive coupling connected to the inner sleeve configured to be detachably coupled to the motor shaft; first and second magnets carried in opposing surfaces of the drive coupling wherein the North and South poles of each magnet are oriented differently relative to said central axis.

Clause 6: A medical system for treating tissue comprising a probe coupled to an elongated shaft assembly including first and second members; a motor drive adapted to moves the first member relative to the second member; and a processor having a dynamic braking algorithm configured to control the motor drive to stop movement of the first member relative to the second member in a targeted default position; wherein the processor is further configured to determine if the first member is in a non-default position after being stopped by the dynamic braking algorithm; and wherein the processor is further configured to move the first member to the default position if the first member is determined to be in a non-default position.

Clause 7: An arthroscopic cutter comprising a cutter body having a central axis and a plurality of cutting edges separated by flutes; wherein the cutting edges have cutting edge portions that (i) face radially outward from a surface of the cutter body, (ii) face distally from a surface of the body, and face radially inward toward said central axis in a distal recess in the cutter body.

Clause 8: The arthroscopic cutter of clause 7 wherein said distal recess has an axial depth of at least 1 mm.

Clause 9: The arthroscopic cutter of clause 7 wherein said distal recess has an axial depth of at least 2 mm.

Clause 10: The arthroscopic cutter of clause 7 wherein said distal recess transitions to a bore extending through the cutter body.

Clause 11: The arthroscopic cutter of clause 7 wherein the cutter body is formed from a wear-resistant ceramic material.

Clause 12: The arthroscopic cutter of clause 7 wherein each cutting edge is non-helical and aligned with said central axis to facilitate ceramic injection molding of the cutter body.

Clause 13: The arthroscopic cutter of clause 7 wherein each cutting edge is helical.

Clause 14: The arthroscopic cutter of clause 7 wherein the number of cutting edges is within the range of 2 to 100.

Clause 15: The arthroscopic cutter of clause 7 further comprising at least one electrode in a surface of the cutter body.

Clause 16: The arthroscopic cutter of clause 7 further comprising an electrode in a flute of the cutter body.

Clause 17: The arthroscopic cutter of clause 7 further comprising a window in a surface of the cutter body communicating with a negative pressure source.

Clause 18: An arthroscopic cutter comprising a ceramic cutter body with a central lumen extending therethrough; and a plurality of cutting edges that extend radially outward on the cutter body, and extend distally around a distal nose of the cutter body and face radially inward in a wall of said central lumen.

Clause 19: The arthroscopic cutter of clause 18 further comprising at least one electrode in a surface of the cutter body.

Clause 20: The arthroscopic cutter of clause 18 further comprising a negative pressure source communicating with the central lumen.

Clause 21: A method of operating a medical system, comprising providing a fluid management system including an inflow pump coupled to inflow line for delivering a distention fluid through an access cannula to a working space, wherein a sensor coupled to the inflow line is configured to sense fluid pressure in the working space during a procedure, and wherein the sensor is adapted to send signals to a controller to control the inflow pump; actuating the inflow pump to provide a flow through the inflow cannula prior to introduction into the working space to thereby determine a cannula back pressure value; calibrating the system with said back pressure value to allow for measurement of fluid pressure in the working space.

Clause 22: The method of operating the medical system of clause 21 further comprising introducing the cannula into the working space, and operating the inflow pump to maintain a selected fluid pressure in the working space based on signals from said pressure sensor as adjusted by said back pressure value.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to devices for cutting, ablating and removing bone and soft tissue and related methods of use. Several variations of the invention will now be described to provide an overall understanding of the principles of the form, function and methods of use of the devices disclosed herein. In one variation, the present disclosure provides for an arthroscopic cutter or burr assembly for cutting or abrading bone that is disposable and is configured for detachable coupling to a non-disposable handle and motor drive component. This description of the general principles of this invention is not meant to limit the inventive concepts in the appended claims.

In general, one embodiment provides a high-speed rotating ceramic cutter or burr that is configured for use in many arthroscopic surgical applications, including but not limited to treating bone in shoulders, knees, hips, wrists, ankles and the spine. More in particular, the device includes a cutting member that is fabricated entirely of a ceramic material that is extremely hard and durable, as described in detail below. A motor drive is operatively coupled to the ceramic cutter to rotate the burr edges at speeds ranging from 3,000 RPM to 20,000 RPM.

Figure 1:
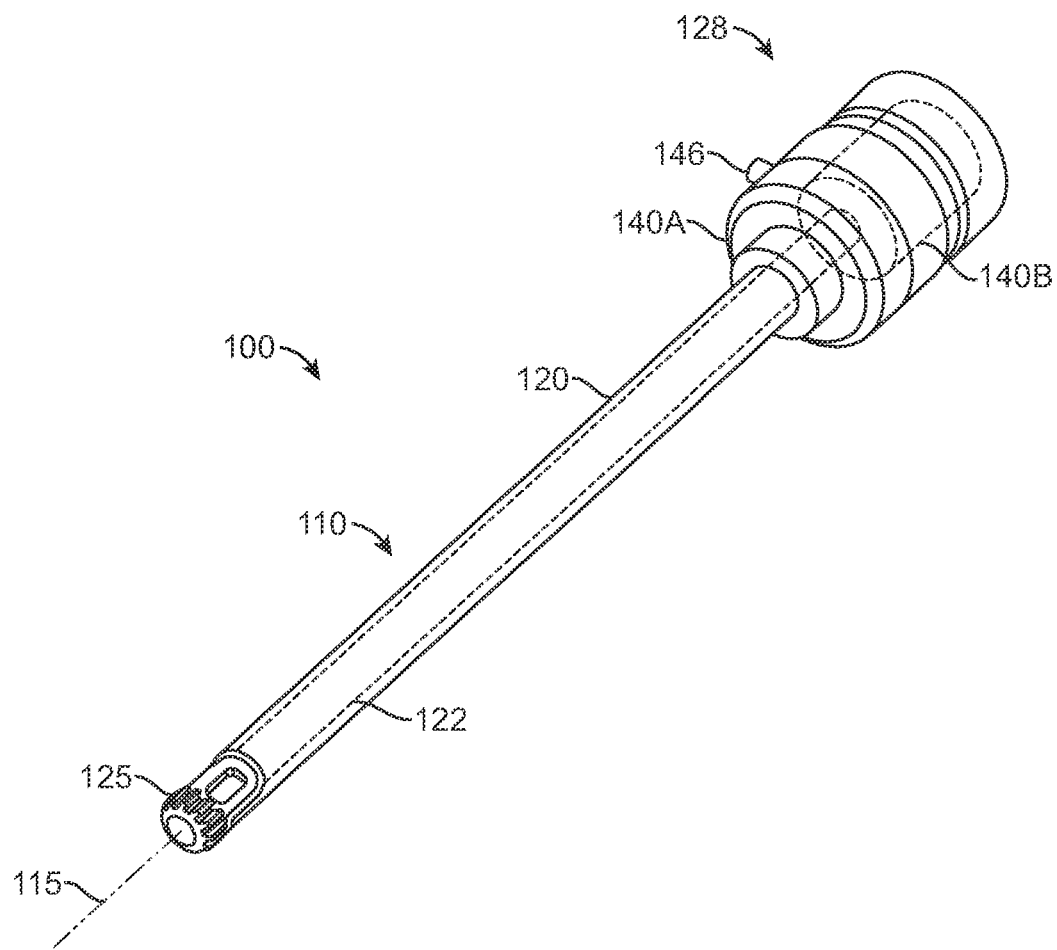
FIG. 1 is a perspective view of a disposable arthroscopic cutter or burr assembly with a ceramic cutting member carried at the distal end of a rotatable inner sleeve with a window in the cutting member proximal to the cutting edges of the burr.
Figure 2:
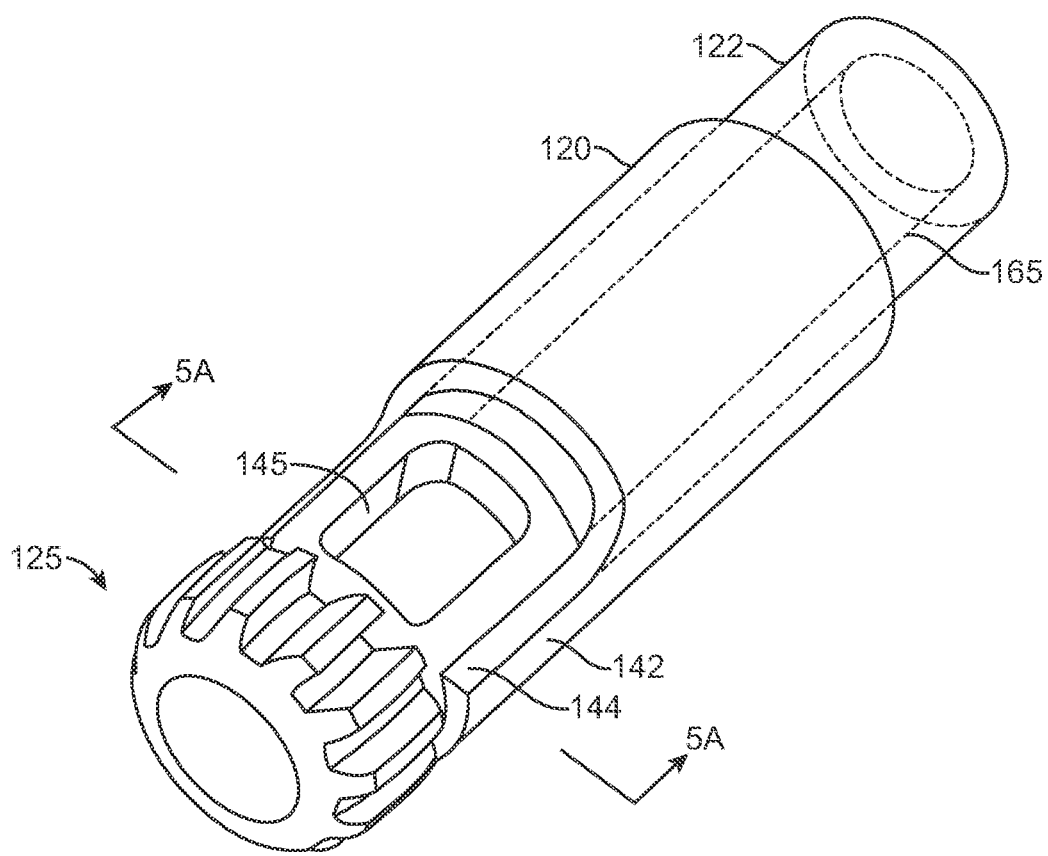
FIG. 2 is an enlarged perspective view of the ceramic cutting member of the arthroscopic cutter or burr assembly of FIG. 1.

In one variation shown in FIGS. 1-2, an arthroscopic cutter or burr assembly 100 is provided for cutting and removing hard tissue, which operates in a manner similar to commercially available metals shavers and burrs. FIG. 1 shows disposable burr assembly 100 that is adapted for detachable coupling to a handle 104 and motor drive unit 105 therein as shown in FIG. 3.

The cutter assembly 100 has a shaft 110 extending along longitudinal axis 115 that comprises an outer sleeve 120 and an inner sleeve 122 rotatably disposed therein with the inner sleeve 122 carrying a distal ceramic cutting member 125. The shaft 110 extends from a proximal hub assembly 128 wherein the outer sleeve 120 is coupled in a fixed manner to an outer hub 140A which can be an injection molded plastic, for example, with the outer sleeve 120 insert molded therein. The inner sleeve 122 is coupled to an inner hub 140B (phantom view) that is configured for coupling to the motor drive unit 105 (FIG. 3). The outer and inner sleeves 120 and 122 typically can be a thin wall stainless steel tube, but other materials can be used such as ceramics, metals, plastics or combinations thereof.

Referring to FIG. 2, the outer sleeve 120 extends to distal sleeve region 142 that has an open end and cut-out 144 that is adapted to expose a window 145 in the ceramic cutting member 125 during a portion of the inner sleeve's rotation. Referring to FIGS. 1 and 3, the proximal hub 128 of the burr assembly 100 is configured with a J-lock, snap-fit feature, screw thread or other suitable feature for detachably locking the hub assembly 128 into the handle 104. As can be seen in FIG. 1, the outer hub 140A includes a projecting key 146 that is adapted to mate with a receiving J-lock slot 148 in the handle 104 (see FIG. 3).

Figure 3:
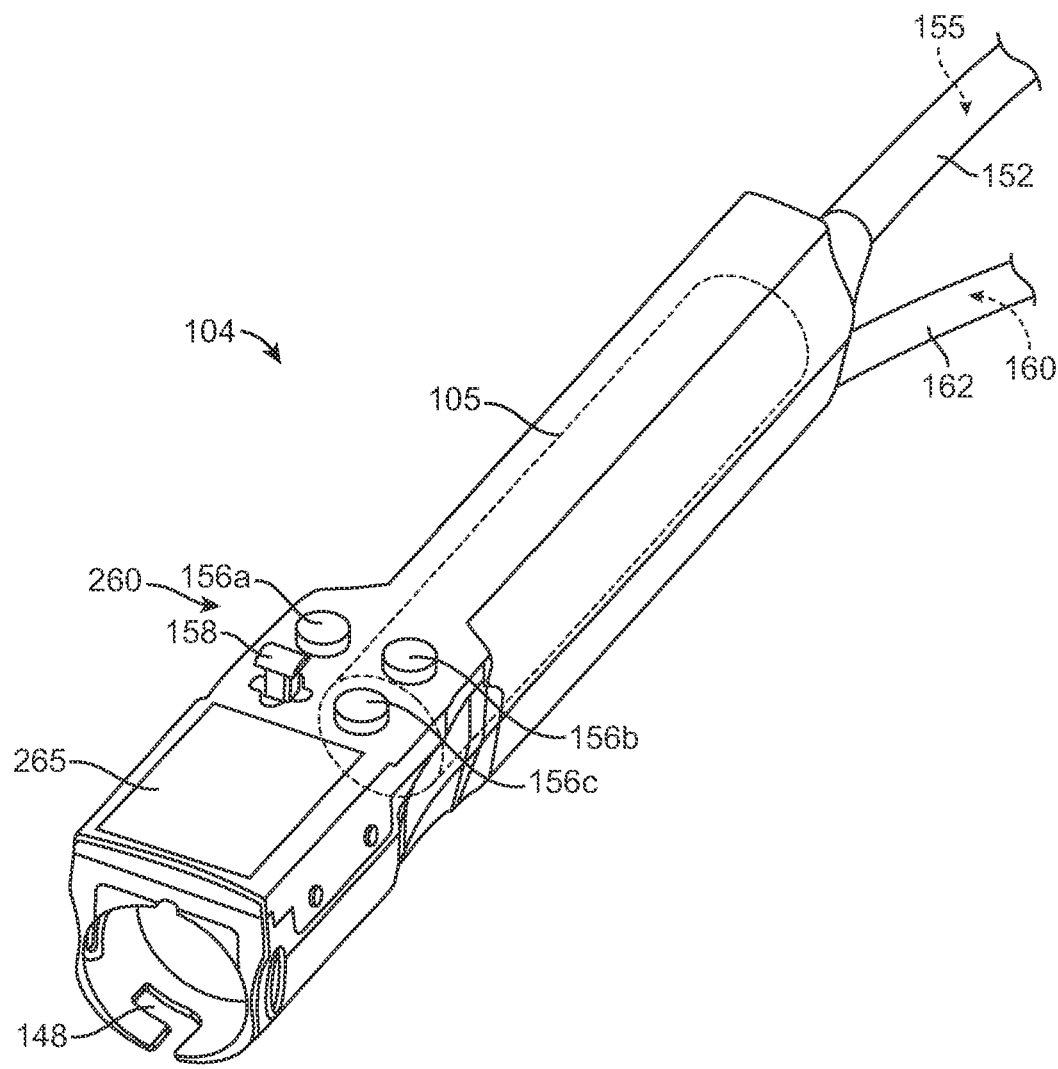
FIG. 3 is a perspective view of a handle body with a motor drive unit to which the burr assembly of FIG. 1 can be coupled, with the handle body including an LCD screen for displaying operating parameters of device during use together with a joystick and mode control actuators on the handle.

In FIG. 3, it can be seen that the handle 104 is operatively coupled by electrical cable 152 to a controller 155 which controls the motor drive unit 105. Actuator buttons 156a, 156b or 156c on the handle 104 can be used to select operating modes, such as various rotational modes for the ceramic cutting member. In one variation, a joystick 158 may be moved forward and backward to adjust the rotational speed of the ceramic cutting member 125. The rotational speed of the cutter can be continuously adjustable, or can be adjusted in increments up to 20,000 RPM. FIG. 3 further shows that negative pressure source 160 is coupled to aspiration tubing 162 which communicates with a flow channel in the handle 104 and lumen 165 in inner sleeve 122 which extends to window 145 in the ceramic cutting member 125 (FIG. 2).

Figure 4:
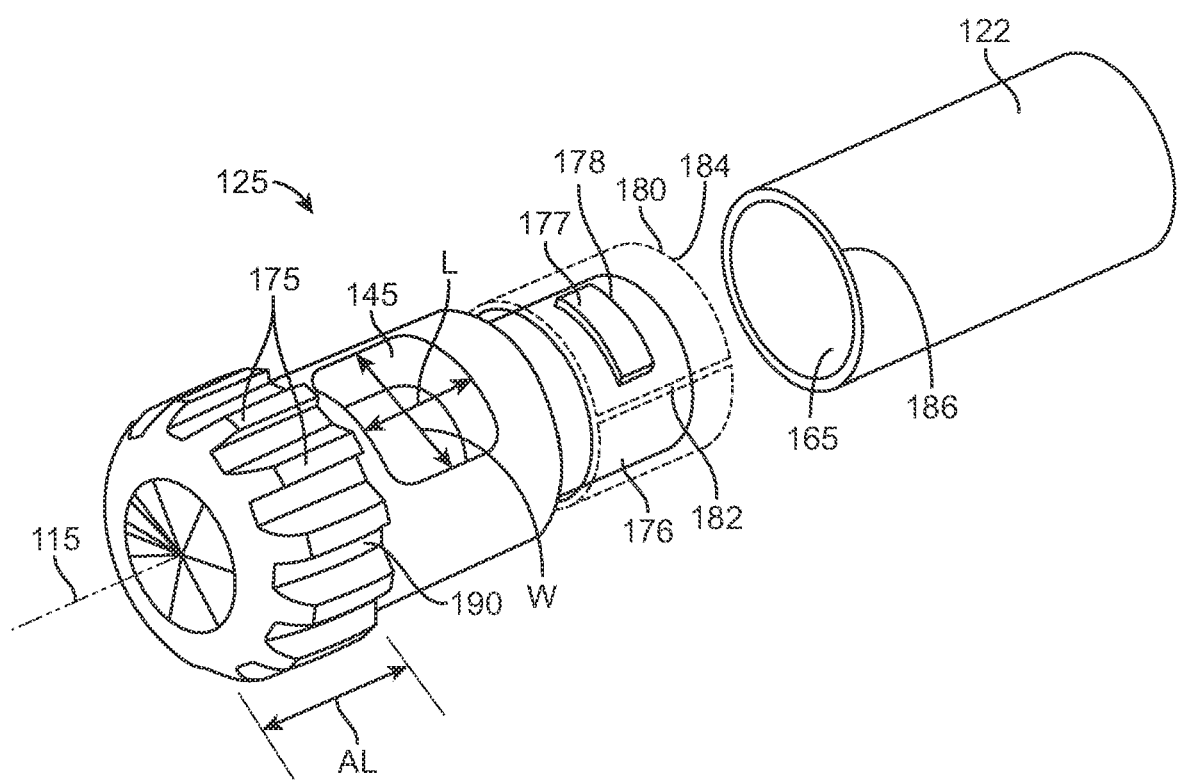
FIG. 4 is an enlarged perspective view of the ceramic cutting member showing a manner of coupling the cutter to a distal end of the inner sleeve of the burr assembly.

Now referring to FIGS. 2 and 4, the cutting member 125 comprises a ceramic body or monolith that is fabricated entirely of a technical ceramic material that has a very high hardness rating and a high fracture toughness rating, where "hardness" is measured on a Vickers scale and "fracture toughness" is measured in $MPam^{1/2}$. Fracture toughness refers to a property which describes the ability of a material containing a flaw or crack to resist further fracture and expresses a material's resistance to brittle fracture. The occurrence of flaws is not completely avoidable in the fabrication and processing of any components.

The authors evaluated technical ceramic materials and tested prototypes to determine which ceramics are best suited for the non-metal cutting member 125. When comparing the material hardness of the ceramic cutters of the invention to prior art metal cutters, it can easily be understood why typical stainless steel bone burrs are not optimal. Types 304 and 316 stainless steel have hardness ratings of 1.7 and 2.1, respectively, which is low and a fracture toughness ratings of 228 and 278, respectively, which is very high. Human bone has a hardness rating of 0.8, so a stainless steel cutter is only about 2.5 times harder than bone. The high fracture toughness of stainless steel provides ductile behavior which results in rapid cleaving and wear on sharp edges of a stainless steel cutting member. In contrast, technical ceramic materials have a hardness ranging from approximately 10 to 15, which is five to six times greater than stainless steel and which is 10 to 15 times harder than cortical bone. As a result, the sharp cutting edges of a ceramic remain sharp and will not become dull when cutting bone. The fracture toughness of suitable ceramics ranges from about 5 to 13 which is sufficient to prevent any fracturing or chipping of the ceramic cutting edges. The authors determined that a hardness-to-fracture toughness ratio ("hardness-toughness ratio") is a useful term for characterizing ceramic materials that are suitable for the invention as can be understood form the Chart A below, which lists hardness and fracture toughness of cortical bone, a 304 stainless steel, and several technical ceramic materials.

CHART A

|  | Hardness (GPa) | Fracture Toughness (MPam$^{1/2}$) | Ratio Hardness to Fracture Toughness |
|---|---|---|---|
| Cortical bone | 0.8 | 12 | .07:1 |
| Stainless steel 304 | 2.1 | 22.8 | .01:1 |
| Yttria-stabilized zirconia (YTZP) YTZP 2000 (Superior Technical Ceramics) | 12.5 | 10 | 1.25:1 |
| YTZP 4000 (Superior Technical Ceramics) | 12.5 | 10 | 1.25:1 |
| YTZP (CoorsTek) | 13.0 | 13 | 1.00:1 |
| Magnesia stabilized zirconia (MSZ) Dura-Z ® (Superior Technical Ceramics) | 12.0 | 11 | 1.09:1 |
| MSZ 200 (CoorsTek) | 11.7 | 12 | 0.98:1 |
| Zirconia toughened alumina (ZTA) YTA-14 (Superior Technical Ceramics) | 14.0 | 5 | 2.80:1 |
| ZTA (CoorsTek) | 14.8 | 6 | 2.47:1 |
| Ceria stabilized zirconia CSZ (Superior Technical Ceramics) | 11.7 | 12 | 0.98:1 |
| Silicon Nitride SiN (Superior Technical Ceramics) | 15.0 | 6 | 2.50:1 |

As can be seen in Chart A, the hardness-toughness ratio for the listed ceramic materials ranges from 98× to 250× greater than the hardness-toughness ratio for stainless steel 304. In one aspect of the invention, a ceramic cutter for cutting hard tissue is provided that has a hardness-toughness ratio of at least 0.5:1, 0.8:1 or 1:1.

In one variation, the ceramic cutting member 125 is a form of zirconia. Zirconia-based ceramics have been widely used in dentistry and such materials were derived from structural ceramics used in aerospace and military armor. Such ceramics were modified to meet the additional requirements of biocompatibility and are doped with stabilizers to achieve high strength and fracture toughness. The types of ceramics used in the current invention have been used in dental implants, and technical details of such zirconia-based ceramics can be found in Volpato, et al., "Application of Zirconia in Dentistry: Biological, Mechanical and Optical Considerations", Chapter 17 in *Advances in Ceramics—Electric and Magnetic Ceramics, Bioceramics, Ceramics and Environment* (2011).

In one variation, the ceramic cutting member 125 is fabricated of an yttria-stabilized zirconia as is known in the field of technical ceramics, and can be provided by CoorsTek Inc., 16000 Table Mountain Pkwy., Golden, CO 80403 or Superior Technical Ceramics Corp., 600 Industrial Park Rd., St. Albans City, VT 05478. Other technical ceramics that may be used consist of magnesia-stabilized zirconia, ceria-stabilized zirconia, zirconia toughened alumina and silicon nitride. In general, in one aspect of the invention, the monolithic ceramic cutting member 125 has a hardness rating of at least 8 Gpa (kg/mm$^2$). In another aspect of the invention, the ceramic cutting member 125 has a fracture toughness of at least 2 MPam$^{1/2}$.

The fabrication of such ceramics or monoblock components are known in the art of technical ceramics, but have not been used in the field of arthroscopic or endoscopic cutting or resecting devices. Ceramic part fabrication includes molding, sintering and then heating the molded part at high temperatures over precise time intervals to transform a compressed ceramic powder into a ceramic monoblock which can provide the hardness range and fracture toughness range as described above. In one variation, the molded ceramic member part can have additional strengthening through hot isostatic pressing of the part. Following the ceramic fabrication process, a subsequent grinding process optionally may be used to sharpen the cutting edges 175 of the burr (see FIGS. 2 and 4).

In FIG. 4, it can be seen that in one variation, the proximal shaft portion 176 of cutting member 125 includes projecting elements 177 which are engaged by receiving openings 178 in a stainless steel split collar 180 shown in phantom view. The split collar 180 can be attached around the shaft portion 176 and projecting elements 177 and then laser welded along weld line 182. Thereafter, proximal end 184 of collar 180 can be laser welded to the distal end 186 of stainless steel inner sleeve 122 to mechanically couple the ceramic body 125 to the metal inner sleeve 122. In another aspect of the invention, the ceramic material is selected to have a coefficient of thermal expansion between is less than 10 ($1\times10^6/°$ C.) which can be close enough to the coefficient of thermal expansion of the metal sleeve 122 so that thermal stresses will be reduced in the mechanical coupling of the ceramic member 125 and sleeve 122 as just described. In another variation, a ceramic cutting member can be coupled to metal sleeve 122 by brazing, adhesives, threads or a combination thereof.

Referring to FIGS. 1 and 4, the ceramic cutting member 125 has window 145 therein which can extend over a radial angle of about 10° to 90° of the cutting member's shaft. In the variation of FIG. 1, the window is positioned proximally to the cutting edges 175, but in other variations, one or more windows or openings can be provided and such openings can extend in the flutes 190 (see FIG. 6) intermediate the cutting edges 175 or around a rounded distal nose of the ceramic cutting member 125. The length L of window 145 can range from 2 mm to 10 mm depending on the diameter and design of the ceramic member 125, with a width W of 1 mm to 10 mm.

Figure 6:
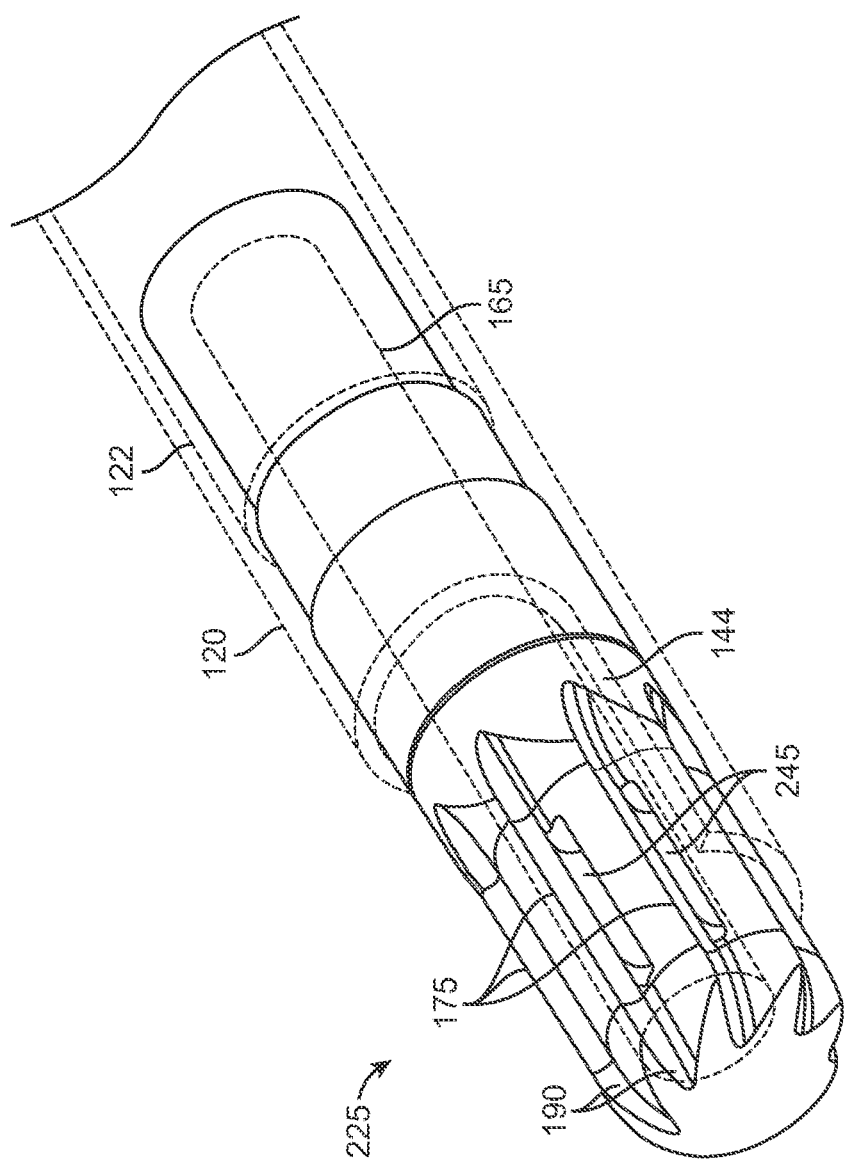
FIG. 6 is a perspective view of another ceramic cutting member carried at the distal end of an inner sleeve with a somewhat rounded distal nose and deeper flutes than the cutting member of FIGS. 2 and 4, and with aspiration openings or ports formed in the flutes.
Figure 7:
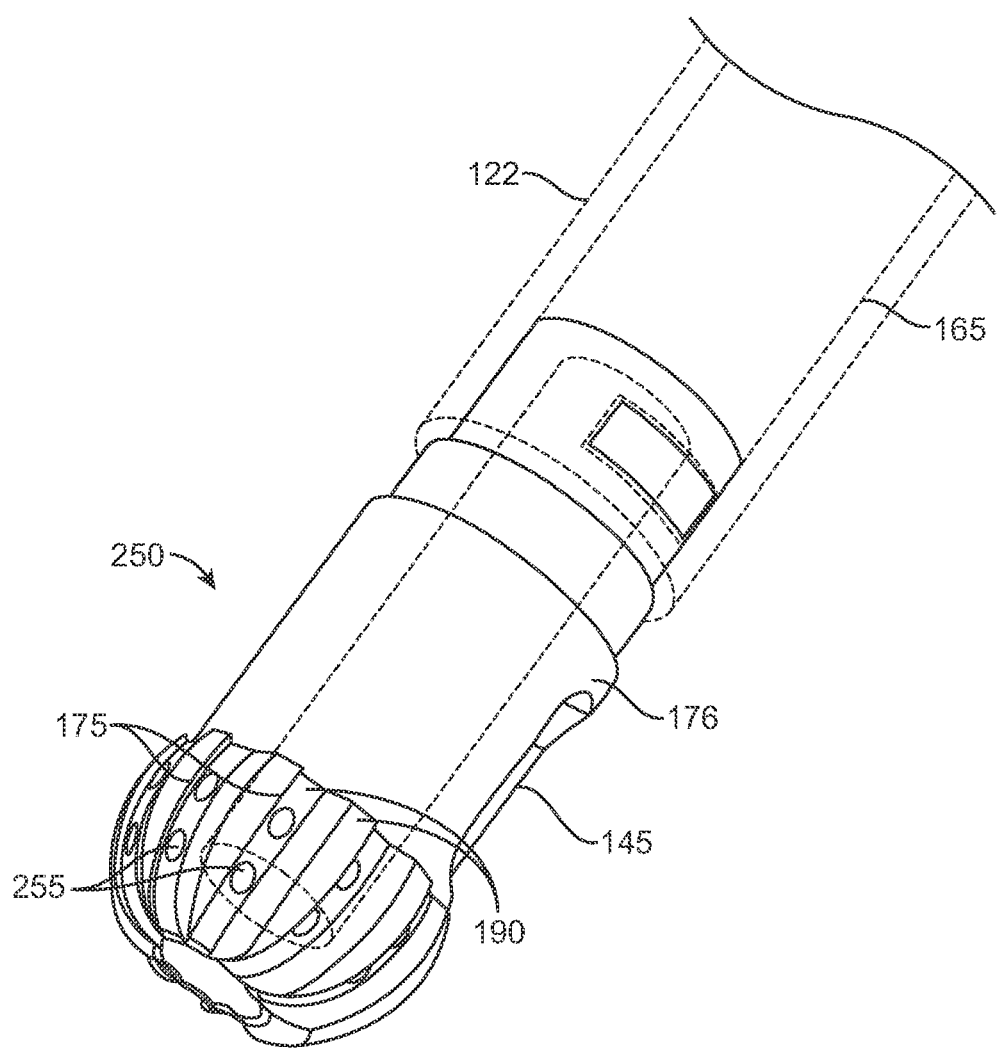
FIG. 7 is a perspective view of another ceramic cutting member with cutting edges that extend around a distal nose of the cutter together with an aspiration window in the shaft portion and aspiration openings in the flutes.

FIGS. 1 and 4 shows the ceramic burr or cutting member 125 with a plurality of sharp cutting edges 175 which can extend helically, axially, longitudinally or in a cross-hatched configuration around the cutting member, or any combination thereof. The number of cutting edges 175 ands intermediate flutes 190 can range from 2 to 100 with a flute depth ranging from 0.10 mm to 2.5 mm. In the variation shown in FIGS. 2 and 4, the outer surface or periphery of the cutting edges 175 is cylindrical, but such a surface or periphery can be angled relative to axis 115 or rounded as shown in FIGS. 6 and 7. The axial length AL of the cutting edges can range between 1 mm and 10 mm. While the cutting edges 175 as depicted in FIG. 4 are configured for optimal bone cutting or abrading in a single direction of rotation, it should be appreciated the that the controller 155 and motor drive 105 can be adapted to rotate the ceramic cutting member 125 in either rotational direction, or oscillate the cutting member back and forth in opposing rotational directions.

Figure 5A:
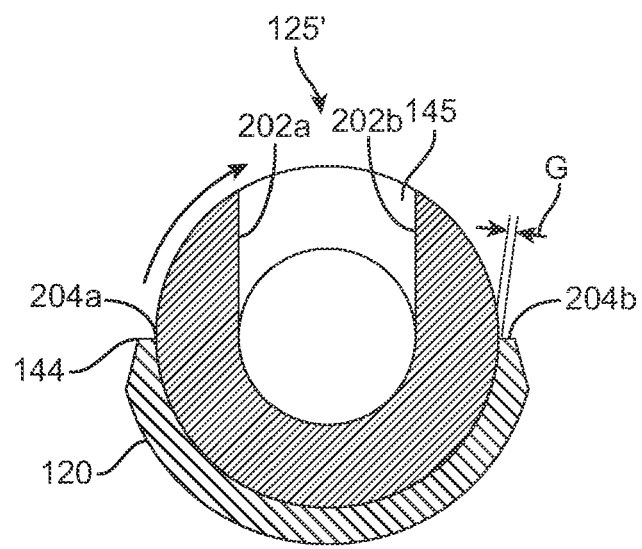
FIG. 5A is a cross-sectional taken along line 5A-5A of FIG. 2 showing the close tolerance between sharp cutting edges of a window in a ceramic cutting member and sharp lateral edges of the outer sleeve which provides a scissor-like cutting effect in soft tissue.
Figure 5B:
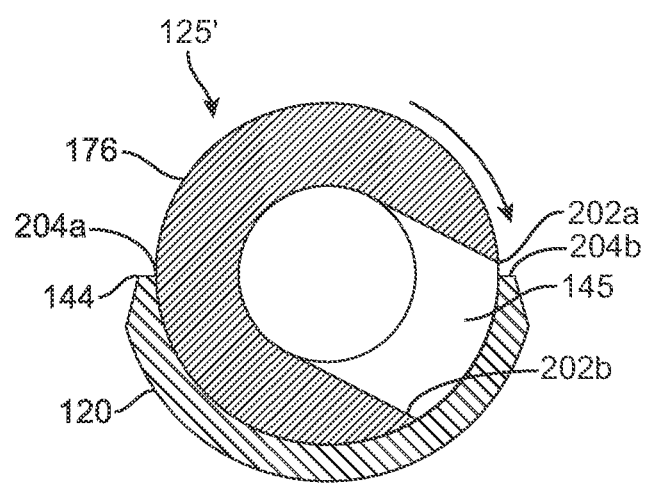
FIG. 5B is a cross-sectional view similar to FIG. 5A with the ceramic cutting member in a different rotational position than in FIG. 5A.

FIGS. 5A-5B illustrate a sectional view of the window 145 and shaft portion 176 of a ceramic cutting member 125' that is very similar to the ceramic member 125 of FIGS. 2 and 4. In this variation, the ceramic cutting member has window 145 with one or both lateral sides configured with sharp cutting edges 202a and 202b which are adapted to resect tissue when rotated or oscillated within close proximity, or in scissor-like contact with, the lateral edges 204a and 204b of the sleeve walls in the cut-out portion 144 of the distal end of outer sleeve 120 (see FIG. 2). Thus, in general, the sharp edges of window 145 can function as a cutter or shaver for resecting soft tissue rather than hard tissue or bone. In this variation, there is effectively no open gap G between the sharp edges 202a and 202b of the ceramic cutting member 125' and the sharp lateral edges 204a, 204b of the sleeve 120. In another variation, the gap G between the window cutting edges 202a, 202b and the sleeve edges 204a, 204b is less than about 0.020", or less than 0.010".

FIG. 6 illustrates another variation of ceramic cutting member 225 coupled to an inner sleeve 122 in phantom view. The ceramic cutting member again has a plurality of sharp cutting edges 175 and flutes 190 therebetween. The outer sleeve 120 and its distal opening and cut-out shape 144 are also shown in phantom view. In this variation, a plurality of windows or opening 245 are formed within the flutes 190 and communicate with the interior aspiration channel 165 in the ceramic member as described previously.

FIG. 7 illustrates another variation of ceramic cutting member 250 coupled to an inner sleeve 122 (phantom view) with the outer sleeve not shown. The ceramic cutting member 250 is very similar to the ceramic cutter 125 of FIGS. 1, 2 and 4, and again has a plurality of sharp cutting edges 175 and flutes 190 therebetween. In this variation, a plurality of windows or opening 255 are formed in the flutes 190 intermediate the cutting edges 175 and another window 145 is provided in a shaft portion 176 of ceramic member 225 as described previously. The openings 255 and window 145 communicate with the interior aspiration channel 165 in the ceramic member as described above.

It can be understood that the ceramic cutting members can eliminate the possibility of leaving metal particles in a treatment site. In one aspect of the invention, a method of preventing foreign particle induced inflammation in a bone treatment site comprises providing a rotatable cutter fabricated of a ceramic material having a hardness of at least 8 Gpa (kg/mm$^2$) and/or a fracture toughness of at least 2 MPam$^{1/2}$ and rotating the cutter to cut bone without leaving any foreign particles in the treatment site. The method includes removing the cut bone tissue from the treatment site through an aspiration channel in a cutting assembly.

Figure 8:
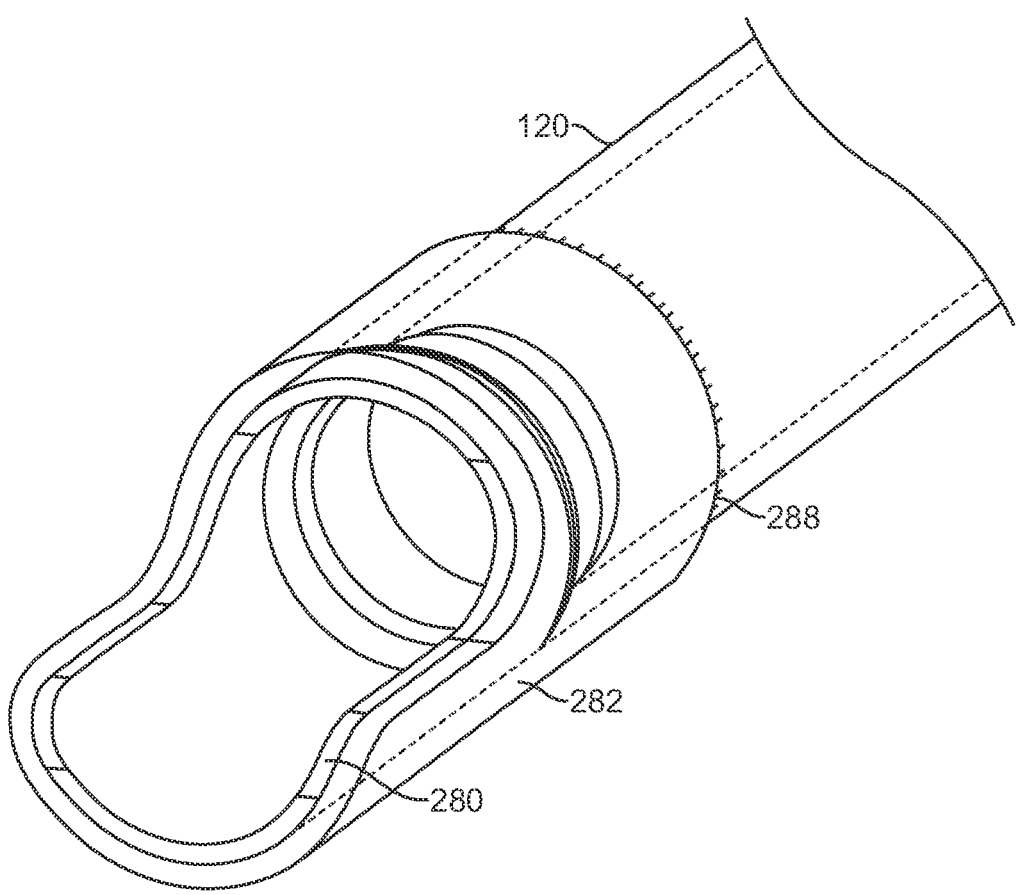
FIG. 8 is a perspective view of a ceramic housing carried at the distal end of the outer sleeve.

FIG. 8 illustrates variation of an outer sleeve assembly with the rotating ceramic cutter and inner sleeve not shown. In the previous variations, such as in FIGS. 1, 2 and 6, shaft portion 176 of the ceramic cutter 125 rotates in a metal outer sleeve 120. FIG. 8 illustrates another variation in which a ceramic cutter (not shown) would rotate in a ceramic housing 280. In this variation, the shaft or a ceramic cutter would thus rotate is a similar ceramic body which may be advantageous when operating a ceramic cutter at high rotational speeds. As can be seen in FIG. 8, a metal distal metal housing 282 is welded to the outer sleeve 120 along weld line 288. The distal metal housing 282 is shaped to support and provide strength to the inner ceramic housing 282.

Figure 9:
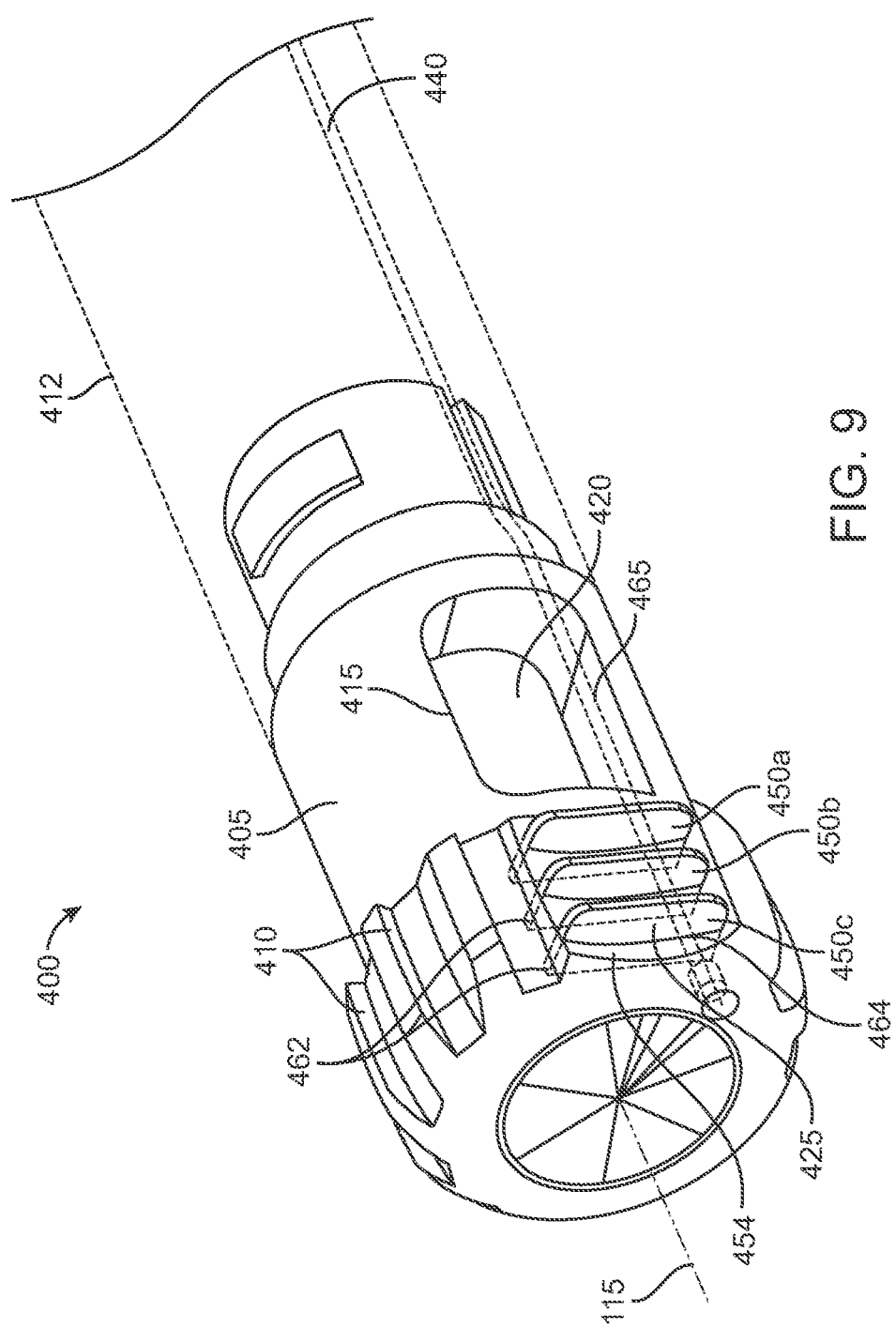
FIG. 9 is a perspective of another variation of a ceramic member with cutting edges that includes an aspiration window and an electrode arrangement positioned distal to the window.
Figure 10:
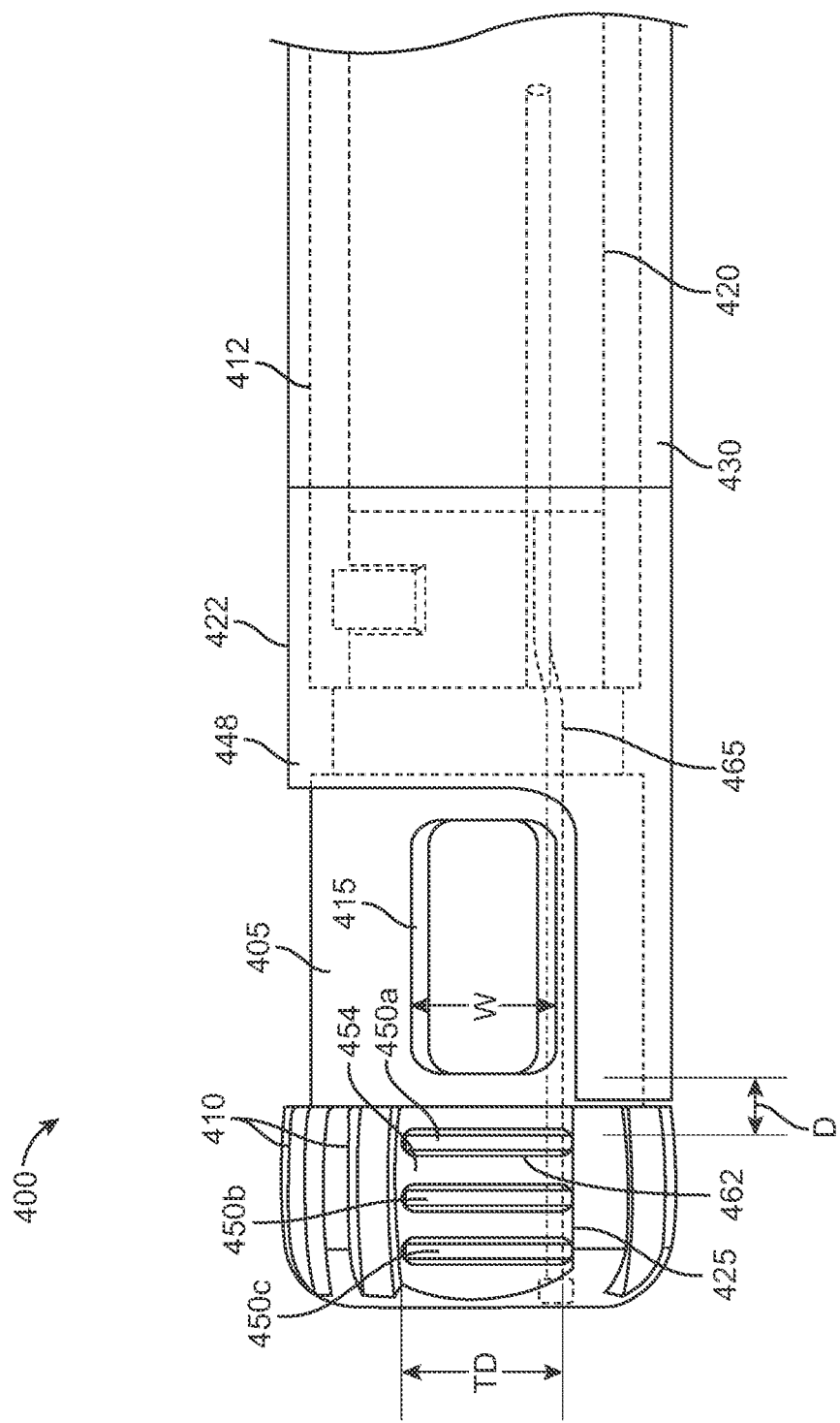
FIG. 10 is an elevational view of a ceramic member and shaft of FIG. 9 showing the width and position of the electrode arrangement in relation to the window.
Figure 11:
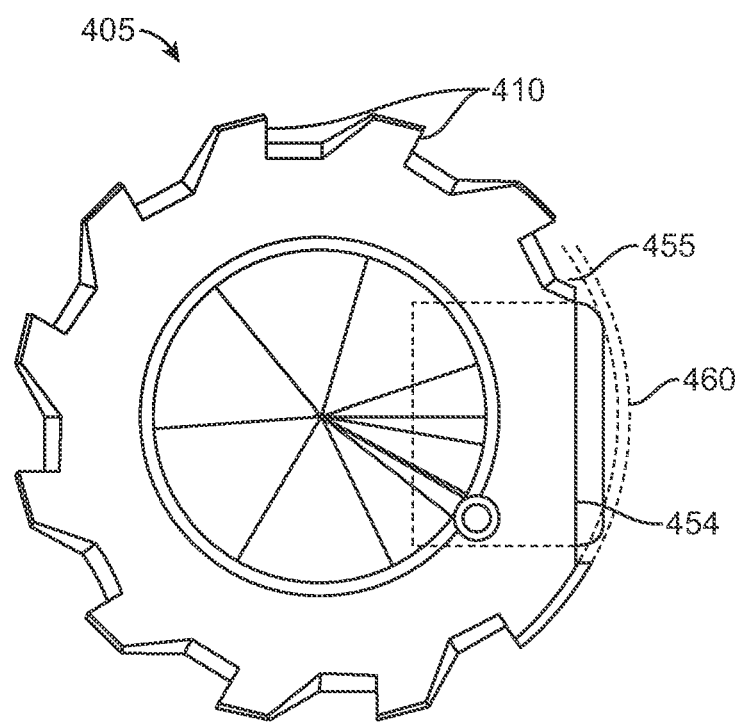
FIG. 11 is an end view of a ceramic member of FIGS. 9-10 the outward periphery of the electrode arrangement in relation to the rotational periphery of the cutting edges of the ceramic member.

FIGS. 9-11 are views of an alternative tissue resecting assembly or working end 400 that includes a ceramic member 405 with cutting edges 410 in a form similar to that described previously. FIG. 9 illustrates the monolithic ceramic member 405 carried as a distal tip of a shaft or inner sleeve 412 as described in previous embodiments. The ceramic member 405 again has a window 415 that communicates with aspiration channel 420 in shaft 412 that is connected to negative pressure source 160 as described previously. The inner sleeve 412 is operatively coupled to a motor drive 105 and rotates in an outer sleeve 422 of the type shown in FIG. 2. The outer sleeve 422 is shown in FIG. 10.

In the variation illustrated in FIG. 9, the ceramic member 405 carries an electrode arrangement 425, or active electrode, having a single polarity that is operatively connected to an RF source 440. A return electrode, or second polarity electrode 430, is provided on the outer sleeve 422 as shown in FIG. 10. In one variation, the outer sleeve 422 can comprise an electrically conductive material such as stainless steel to thereby function as return electrode 445, with a distal portion of outer sleeve 422 is optionally covered by a thin insulative layer 448 such as parylene, to space apart the active electrode 425 from the return electrode 430.

The active electrode arrangement 425 can consist of a single conductive metal element or a plurality of metal elements as shown in FIGS. 9 and 10. In one variation shown in FIG. 9, the plurality of electrode elements 450a, 450b and 450c extend transverse to the longitudinal axis 115 of ceramic member 405 and inner sleeve 412 and are slightly spaced apart in the ceramic member. In one variation shown in FIGS. 9 and 10, the active electrode 425 is spaced distance D from the distal edge 452 of window 415 which is less than 5 mm and often less than 2 mm for reasons described below. The width W and length L of window 415 can be the same as described in a previous embodiment with reference to FIG. 4.

As can be seen in FIGS. 9 and 11, the electrode arrangement 425 is carried intermediate the cutting edges 410 of the ceramic member 405 in a flattened region 454 where the cutting edges 410 have been removed. As can be best understood from FIG. 11, the outer periphery 455 of active electrode 425 is within the cylindrical or rotational periphery of the cutting edges 410 when they rotate. In FIG. 11, the rotational periphery of the cutting edges is indicated at 460. The purpose of the electrode's outer periphery 455 being equal to, or inward from, the cutting edge periphery 460 during rotation is to allow the cutting edges 410 to rotate at high RPMs to engage and cut bone or other hard tissue without the surface or the electrode 425 contacting the targeted tissue.

FIG. 9 further illustrates a method of fabricating the ceramic member 405 with the electrode arrangement 425 carried therein. The molded ceramic member 405 is fabricated with slots 462 that receive the electrode elements 450a-450c, with the electrode elements fabricated from stainless steel, tungsten or a similar conductive material. Each electrode element 450a-450c has a bore 464 extending therethrough for receiving an elongated wire electrode element 465. As can be seen in FIG. 9, and the elongated wire electrode 465 can be inserted from the distal end of the ceramic member 405 through a channel in the ceramic member 405 and through the bores 464 in the electrode elements 450a-450c. The wire electrode 465 can extend through the shaft 412 and is coupled to the RF source 440. The wire electrode element 465 thus can be used as a means of mechanically locking the electrode elements 450a-450c in slots 462 and also as a means to deliver RF energy to the electrode 425.

Another aspect of the invention is illustrated in FIGS. 9-10 wherein it can be seen that the electrode arrangement 425 has a transverse dimension TD relative to axis 115 that is substantial in comparison to the window width W as depicted in FIG. 10. In one variation, the electrode's transverse dimension TD is at least 50% of the window width W, or the transverse dimension TD is at least 80% of the window width W. In the variation of FIGS. 9-10, the electrode transverse dimension TD is 100% or more of the window width W. It has been found that tissue debris and byproducts from RF ablation are better captured and extracted by a window 415 that is wide when compared to the width of the RF plasma ablation being performed.

In general, the tissue resecting system comprises an elongated shaft with a distal tip comprising a ceramic member, a window in the ceramic member connected to an interior channel in the shaft and an electrode arrangement in the ceramic member positioned distal to the window and having a width that is at 50% of the width of the window, at 80% of the width of the window or at 100% of the width of the window. Further, the system includes a negative pressure source 160 in communication with the interior channel 420.

Figure 12A:
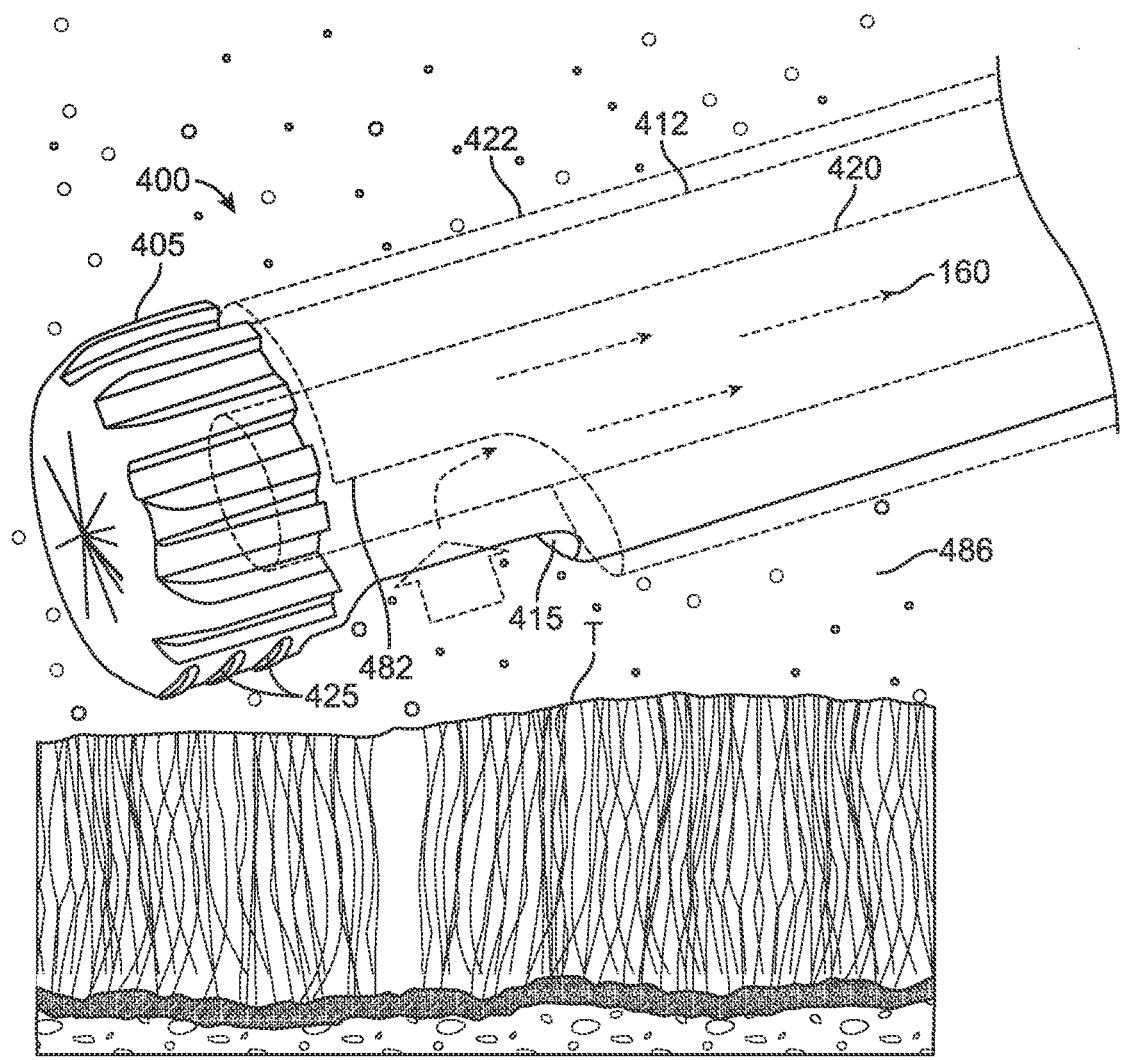
FIG. 12A is a schematic view of the working end and ceramic cutting member of FIGS. 9-11 illustrating a step in a method of use.
Figure 12B:
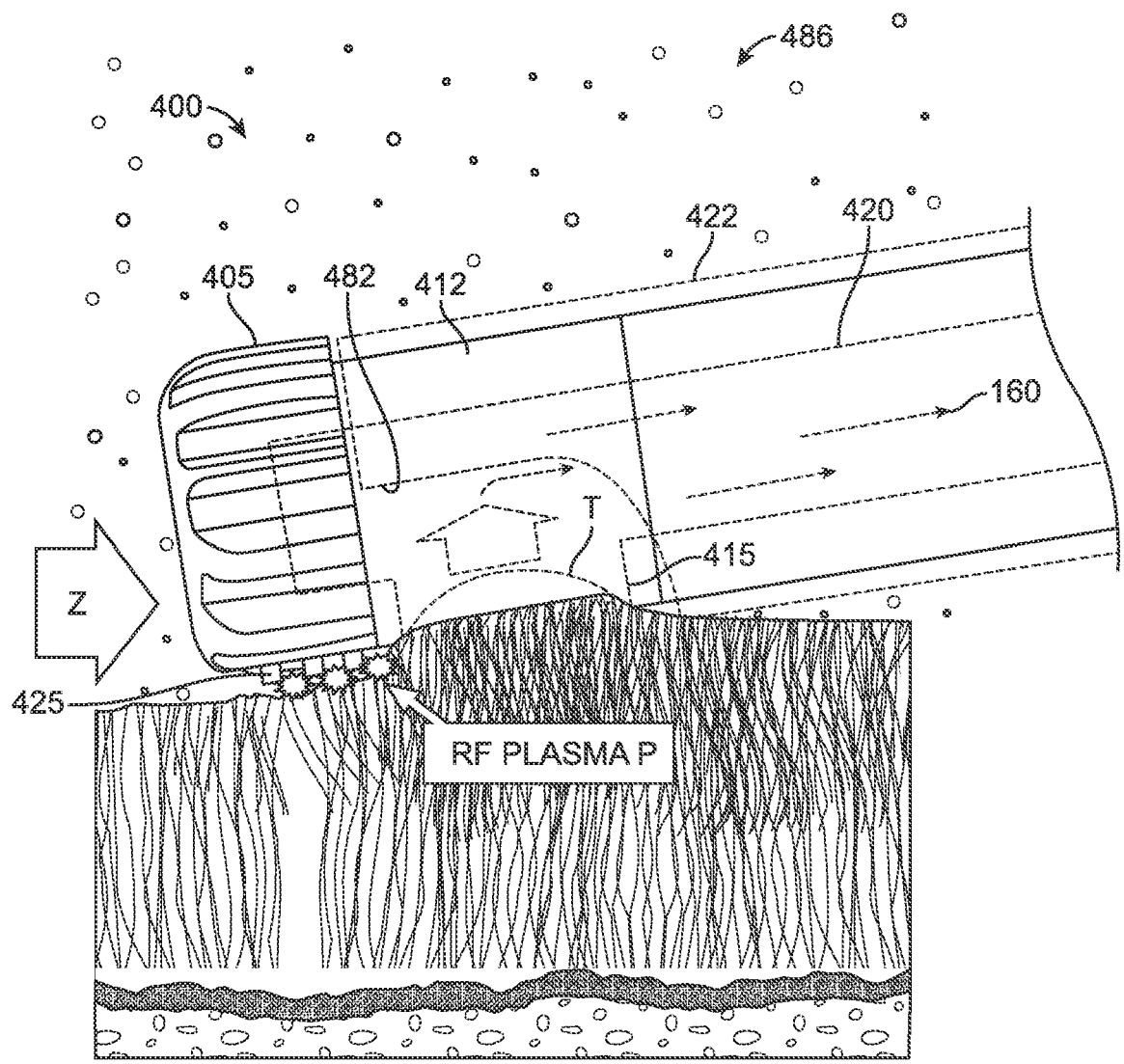
FIG. 12B is another view of the working end of FIG. 12A illustrating a subsequent step in a method of use to ablate a tissue surface.
Figure 12C:
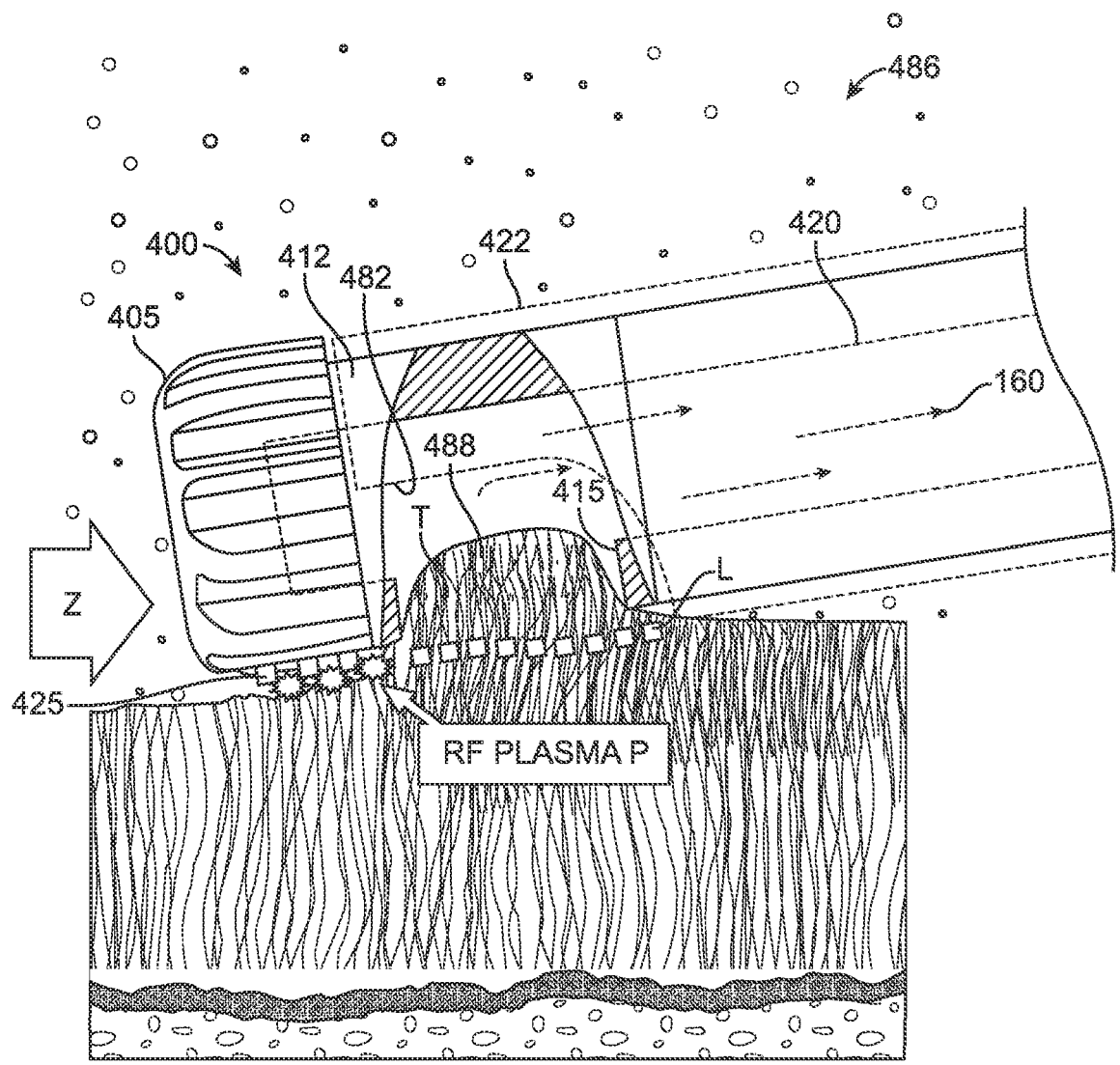
FIG. 12C is a view of the working end of FIG. 12A illustrating a method of tissue resection and aspiration of tissue chips to rapidly remove volumes of tissue.

Now turning to FIGS. 12A-12C, a method of use of the resecting assembly 400 of FIG. 9 can be explained. In FIG. 12A, the system and a controller is operated to stop rotation of the ceramic member 405 in a selected position were the window 415 is exposed in the cut-out 482 of the open end of outer sleeve 422 shown in phantom view. In one variation, a controller algorithm can be adapted to stop the rotation of the ceramic 405 that uses a Hall sensor 484a in the handle 104 (see FIG. 3) that senses the rotation of a magnet 484b carried by inner sleeve hub 140B as shown in FIG. 2. The controller algorithm can receive signals from the Hall sensor which indicated the rotational position of the inner sleeve 412 and ceramic member relative to the outer sleeve 422. The magnet 484b can be positioned in the hub 140B (FIG. 2) so that when sensed by the Hall sensor, the controller algorithm can de-activate the motor drive 105 so as to stop the rotation of the inner sleeve in the selected position.

Under endoscopic vision, referring to FIG. 12B, the physician then can position the electrode arrangement 425 in contact with tissue targeted T for ablation and removal in a working space filled with fluid 486, such as a saline solution which enables RF plasma creation about the electrode. The negative pressure source 160 is activated prior to or contemporaneously with the step of delivering RF energy to electrode 425. Still referring to FIG. 12B, when the ceramic member 405 is positioned in contact with tissue and translated in the direction of arrow Z, the negative pressure source 160 suctions the targeted tissue into the window 415. At the same time, RF energy delivered to electrode arrangement 425 creates a plasma P as is known in the art to thereby ablate tissue. The ablation then will be very close to the window 415 so that tissue debris, fragments, detritus and byproducts will be aspirated along with fluid 486 through the window 415 and outwardly through the interior extraction channel 420 to a collection reservoir. In one method shown schematically in FIG. 12B, a light movement or translation of electrode arrangement 425 over the targeted tissue will ablate a surface layer of the tissue and aspirate away the tissue detritus.

FIG. 12C schematically illustrates a variation of a method which is of particular interest. It has been found if suitable downward pressure on the working end 400 is provided, then axial translation of working end 400 in the direction arrow Z in FIG. 12C, together with suitable negative pressure and the RF energy delivery will cause the plasma P to undercut the targeted tissue along line L that is suctioned into window 415 and then cut and scoop out a tissue chips indicated at 488. In effect, the working end 400 then can function more as a high volume tissue resecting device instead of, or in addition to, its ability to function as a surface ablation tool. In this method, the cutting or scooping of such tissue chips 488 would allow the chips to be entrained in outflows of fluid 486 and aspirated through the extraction channel 420. It has been found that this system with an outer shaft diameter of 7.5 mm, can perform a method of the invention can ablate, resect and remove tissue greater than 15 grams/min, greater than 20 grams/min, and greater than 25 grams/min.

In general, a method corresponding to the invention includes providing an elongated shaft with a working end 400 comprising an active electrode 425 carried adjacent to a window 415 that opens to an interior channel in the shaft which is connected to a negative pressure source, positioning the active electrode and window in contact with targeted tissue in a fluid-filled space, activating the negative pressure source to thereby suction targeted tissue into the window and delivering RF energy to the active electrode to ablate tissue while translating the working end across the targeted tissue. The method further comprises aspirating tissue debris through the interior channel 420. In a method, the working end 400 is translated to remove a surface portion of the targeted tissue. In a variation of the method, the working end 400 is translated to undercut the targeted tissue to thereby remove chips 488 of tissue.

Figure 13A:
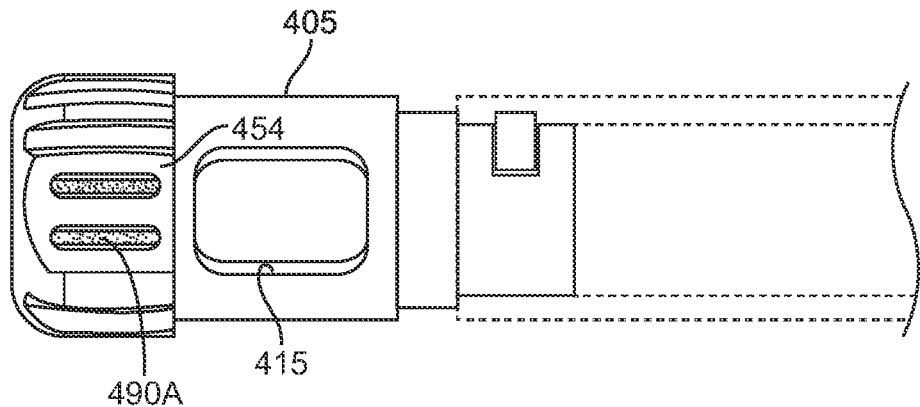
FIG. 13A is an elevational view of an alternative ceramic member and shaft similar to that of FIG. 9 illustrating an electrode variation.
Figure 13B:
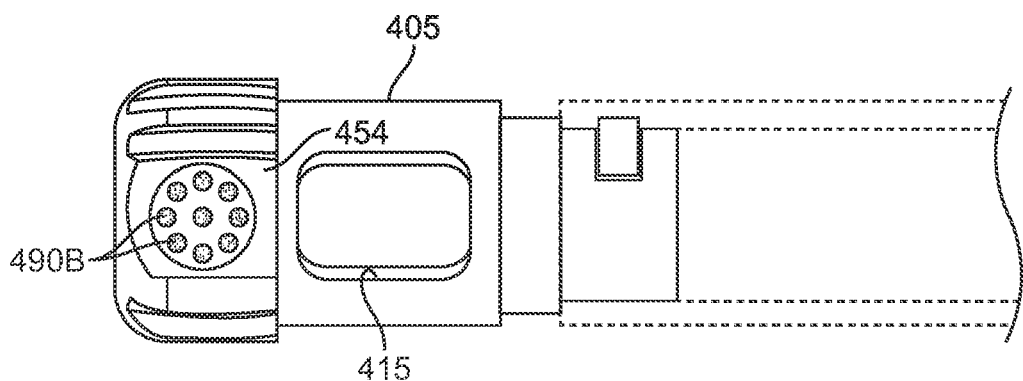
FIG. 13B is an elevational view of another ceramic member similar to that of FIG. 12A illustrating another electrode variation.
Figure 13C:
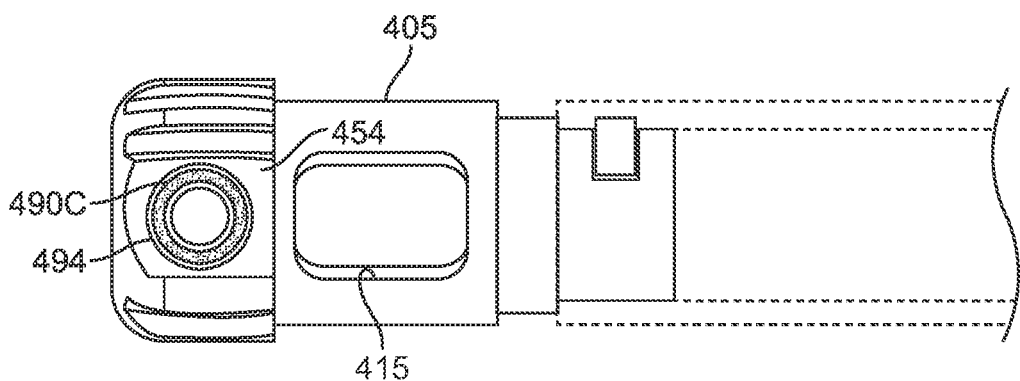
FIG. 13C is an elevational view of another ceramic member similar to that of FIGS. 12A-12B illustrating another electrode variation.

Now turning to FIGS. 13A-13C, other distal ceramic tips of cutting assemblies are illustrated that are similar to that of FIGS. 9-11, except the electrode configurations carried by the ceramic members 405 are varied. In FIG. 13A, the electrode 490A comprises one or more electrode elements extending generally axially distally from the window 415. FIG. 13B illustrates an electrode 490B that comprises a plurality of wire-like elements 492 projecting outwardly from surface 454. FIG. 13C shows electrode 490C that comprises a ring-like element that is partly recessed in a groove 494 in the ceramic body. All of these variations can produce an RF plasma that is effective for surface ablation of tissue, and are positioned adjacent to window 415 to allow aspiration of tissue detritus from the site.

Figure 14:
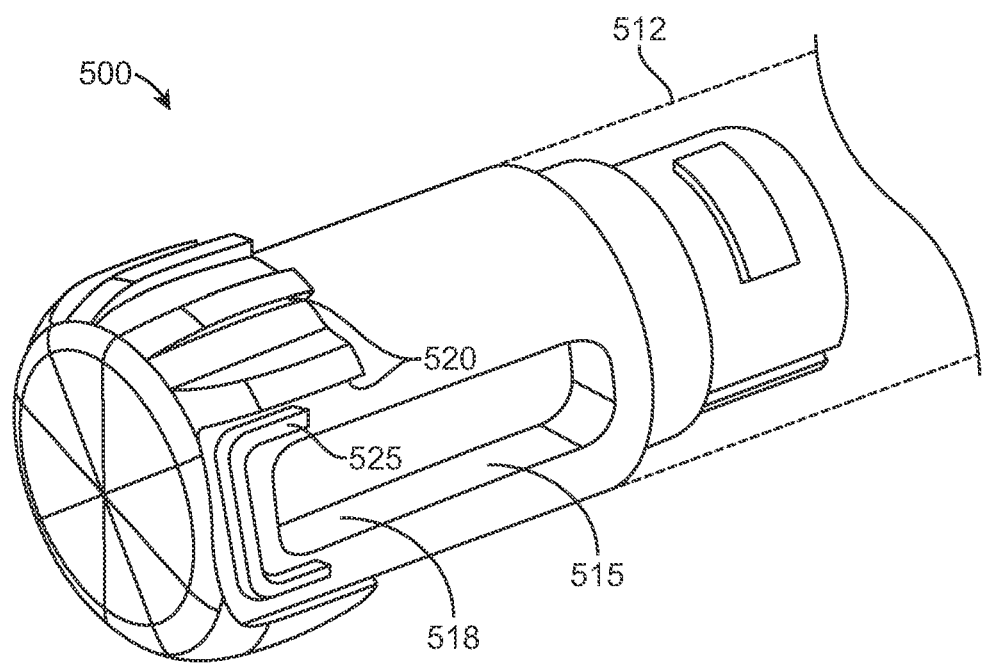
FIG. 14 is a perspective view of an alternative working end and ceramic cutting member with an electrode partly encircling a distal portion of an aspiration window.

FIG. 14 illustrates another variation of a distal ceramic tip 500 of an inner sleeve 512 that is similar to that of FIG. 9 except that the window 515 has a distal portion 518 that extends distally between the cutting edges 520, which is useful for aspirating tissue debris cut by high speed rotation of the cutting edges 520. Further, in the variation of FIG. 14, the electrode 525 encircles a distal portion 518 of window 515 which may be useful for removing tissue debris that is ablated by the electrode when the ceramic tip 500 is not rotated but translated over the targeted tissue as described above in relation to FIG. 12B. In another variation, a distal tip 500 as shown in FIG. 14 can be energized for RF ablation at the same time that the motor drive rotates back and forth (or oscillates) the ceramic member 500 in a radial arc ranging from 1° to 180° and more often from 10° to 90°.

Figure 15A:
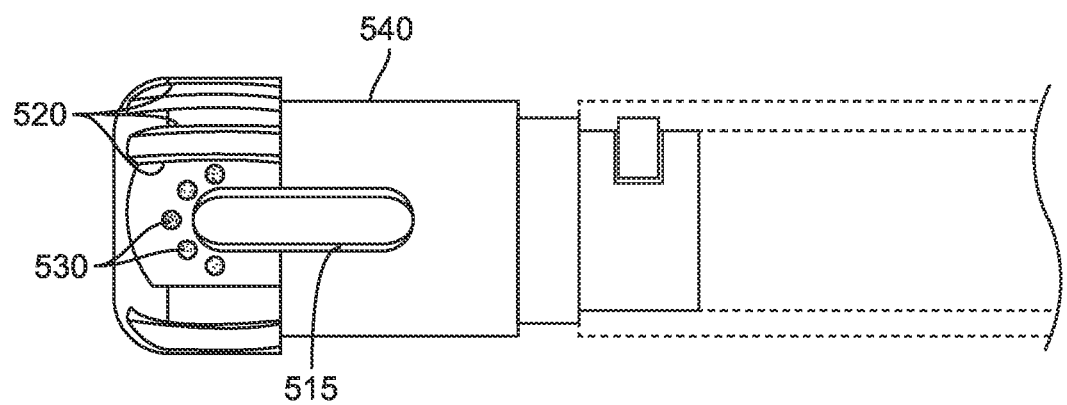
FIG. 15A is an elevational view of a working end variation with an electrode arrangement partly encircling a distal end of the aspiration window.
Figure 15B:
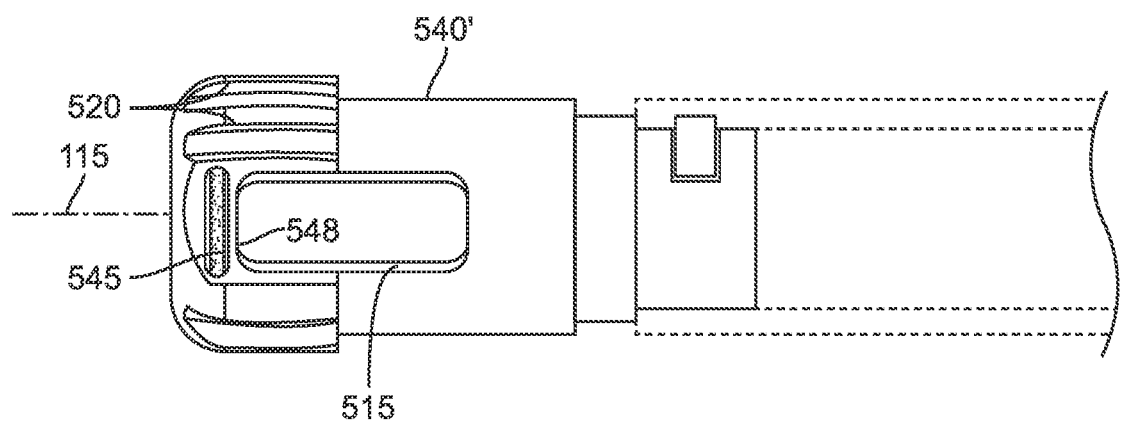
FIG. 15B is an elevational view of another working end variation with an electrode positioned adjacent a distal end of the aspiration window.

FIGS. 15A-15B illustrate other distal ceramic tips 540 and 540' that are similar to that of FIG. 14 except the electrode configurations differ. In FIG. 15A, the window 515 has a distal portion 518 that again extends distally between the cutting edges 520, with electrode 530 comprising a plurality of projecting electrode elements that extend partly around the window 515. FIG. 15B shows a ceramic tip 540' with window 515 having a distal portion 518 that again extends distally between the cutting edges 520. In this variation, the electrode 545 comprises a single blade element that extends transverse to axis 115 and is in close proximity to the distal end 548 of window 515.

Figure 16:
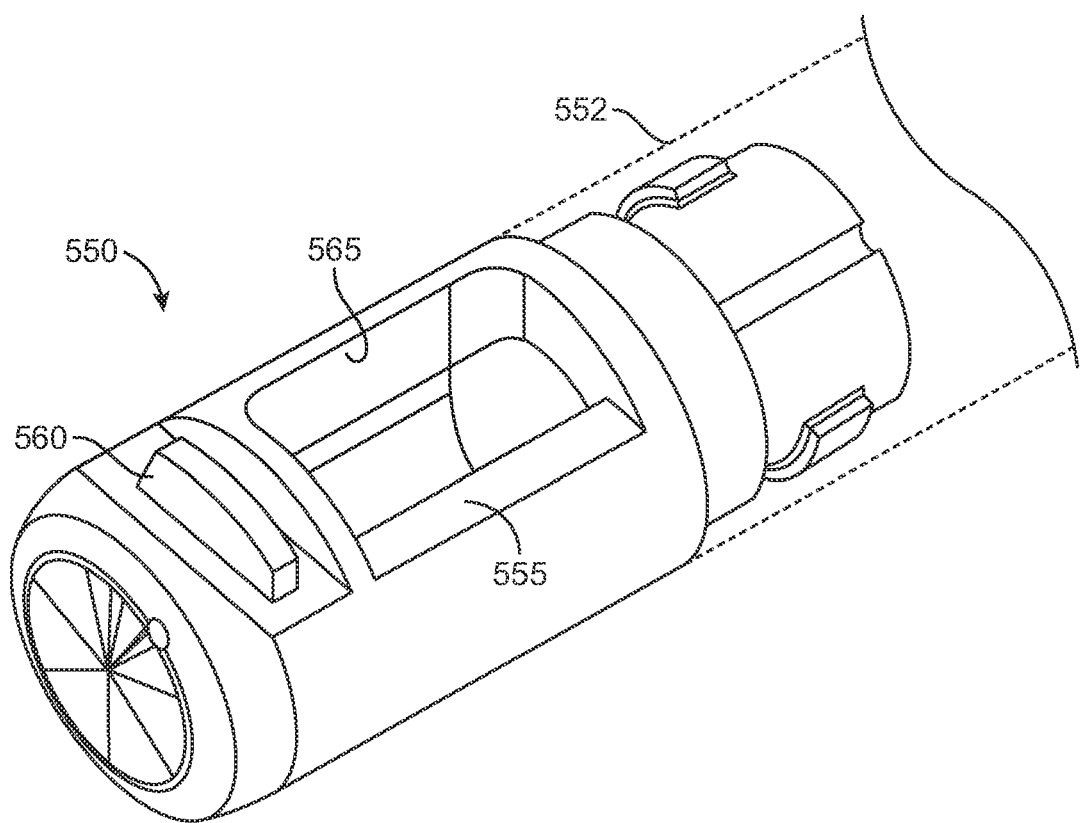
FIG. 16 is a perspective view of a variation of a working end and ceramic member with an electrode adjacent a distal end of an aspiration window having a sharp lateral edge for cutting tissue.

FIG. 16 illustrates another variation of distal ceramic tip 550 of an inner sleeve 552 that is configured without the sharp cutting edges 410 of the embodiment of FIGS. 9-11. In other respects, the arrangement of the window 555 and the electrode 560 is the same as described previously. Further, the outer periphery of the electrode is similar to the outward surface of the ceramic tip 550. In the variation of FIG. 16, the window 555 has at least one sharp edge 565 for cutting soft tissue when the assembly is rotated at a suitable speed from 500 to 5,000 RPM. When the ceramic tip member 550 is maintained in a stationary position and translated over targeted tissue, the electrode 560 can be used to ablate surface layers of tissue as described above.

Figure 17:
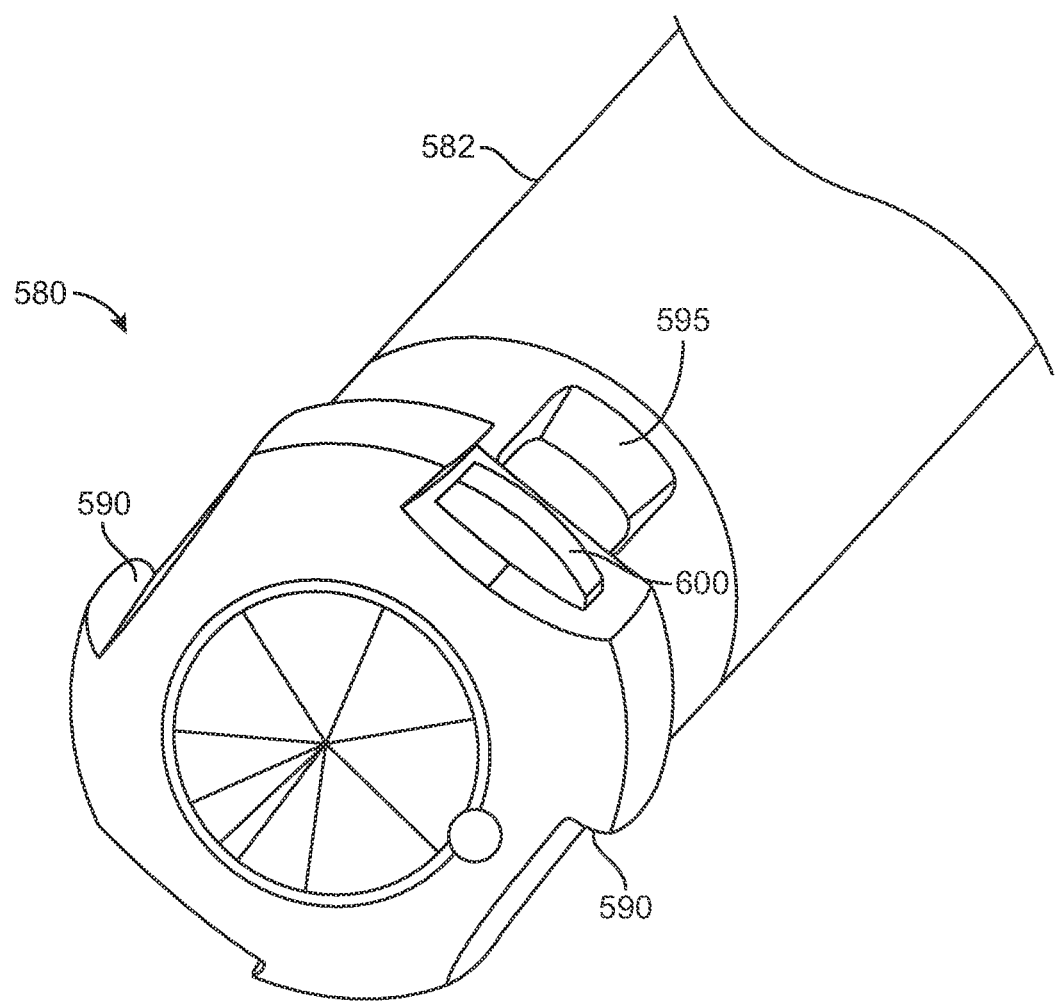
FIG. 17 is a perspective view of a variation of a working end and ceramic member with four cutting edges and an electrode adjacent a distal end of an aspiration window.

FIG. 17 depicts another variation of distal ceramic tip 580 coupled to an inner sleeve 582 that again has sharp burr edges or cutting edges 590 as in the embodiment of FIGS. 9-11. In this variation, the ceramic monolith has only 4 sharp edges 590 which has been found to work well for cutting bone at high RPMs, for example from 8,000 RPM to 20,000 RPM. In this variation, the arrangement of window 595 and electrode 600 is the same as described previously. Again, the outer periphery of electrode 595 is similar to the outward surface of the cutting edges 590.

Figure 21A:
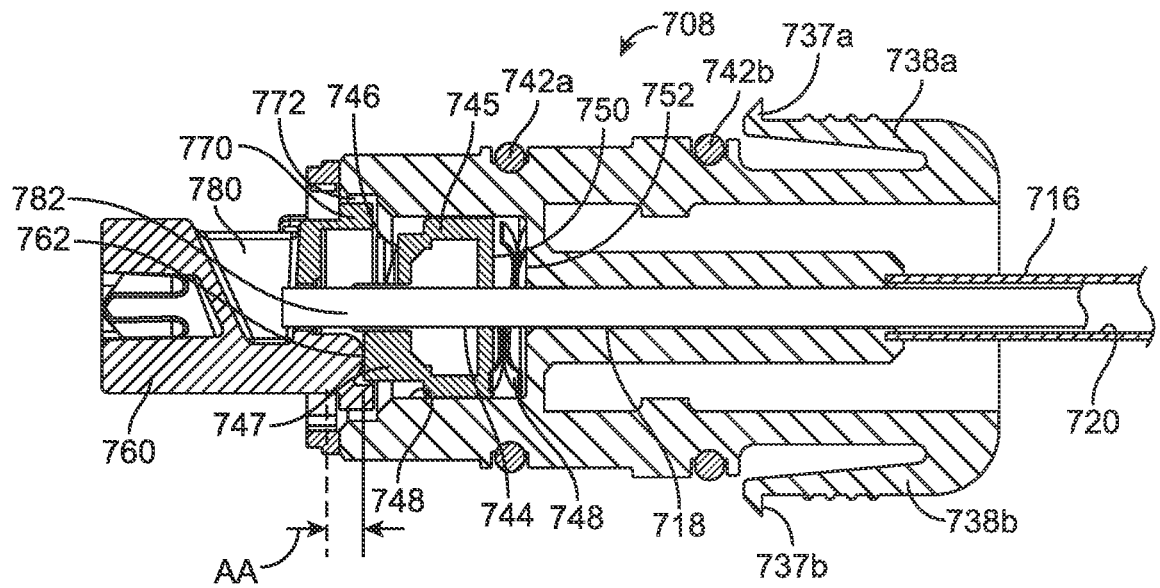
FIG. 21A is a sectional view of the hub of the probe of FIG. 18 taken along line 21A-21A of FIG. 18 showing an actuation mechanism in a first position.
Figure 21B:
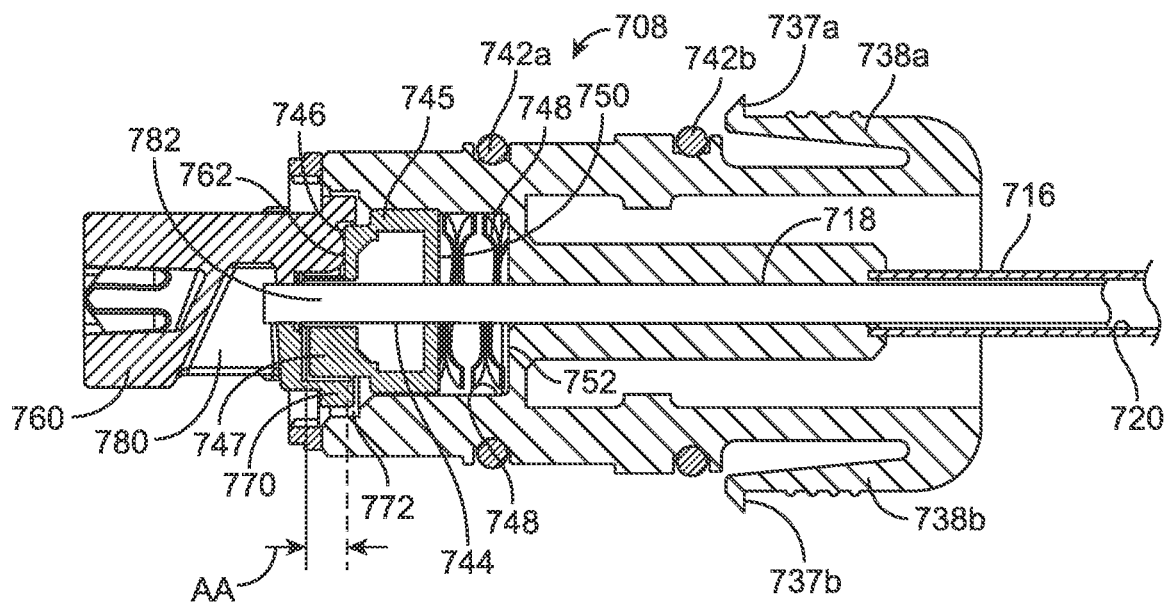
FIG. 21B is a sectional view of the hub of FIG. 21A showing the actuation mechanism in a second position.
Figure 22:
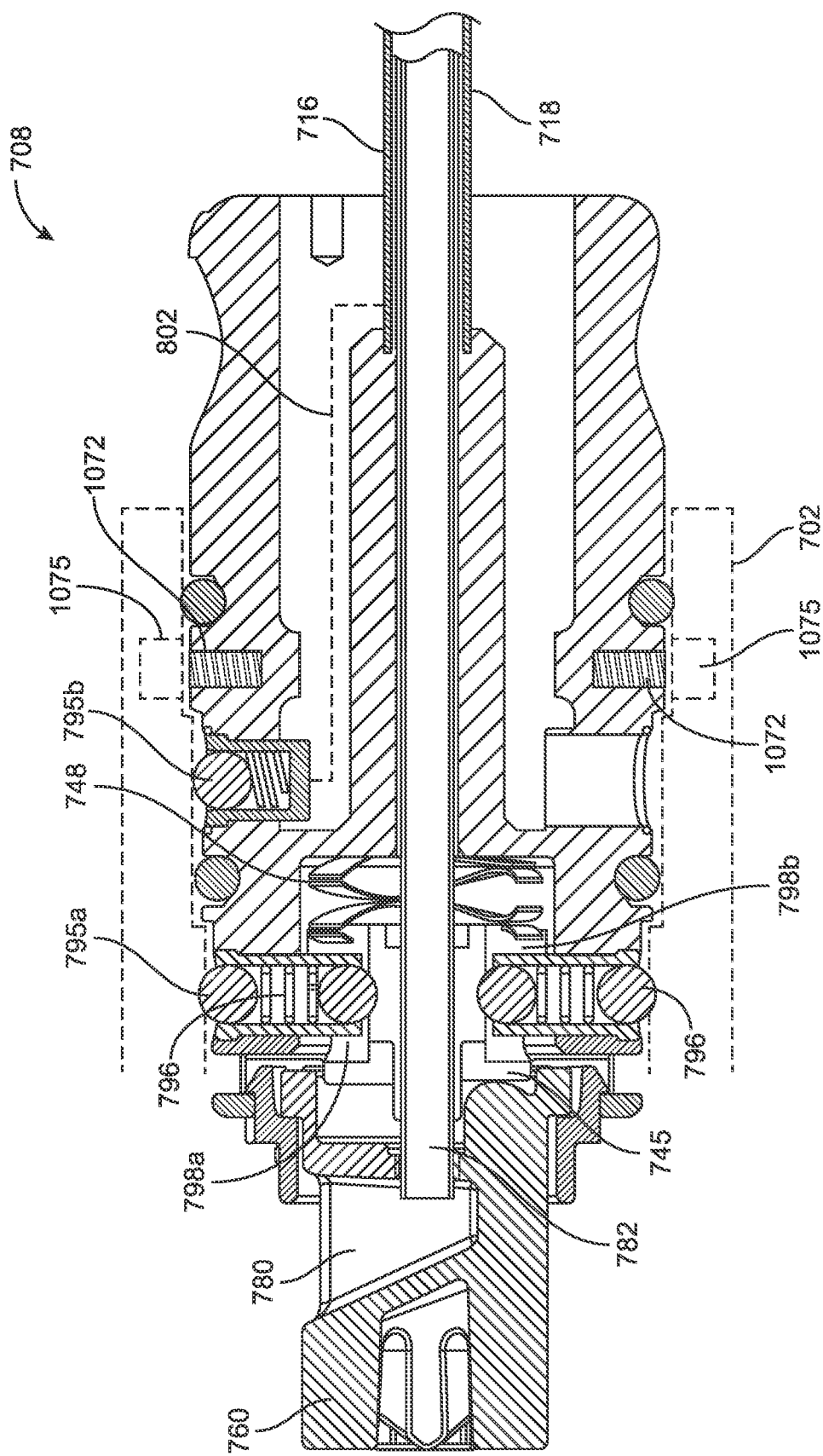
FIG. 22 is a sectional view of the hub of FIG. 21A rotated 90° to illustrate electrical contacts and pathways in the hub.
Figure 23:
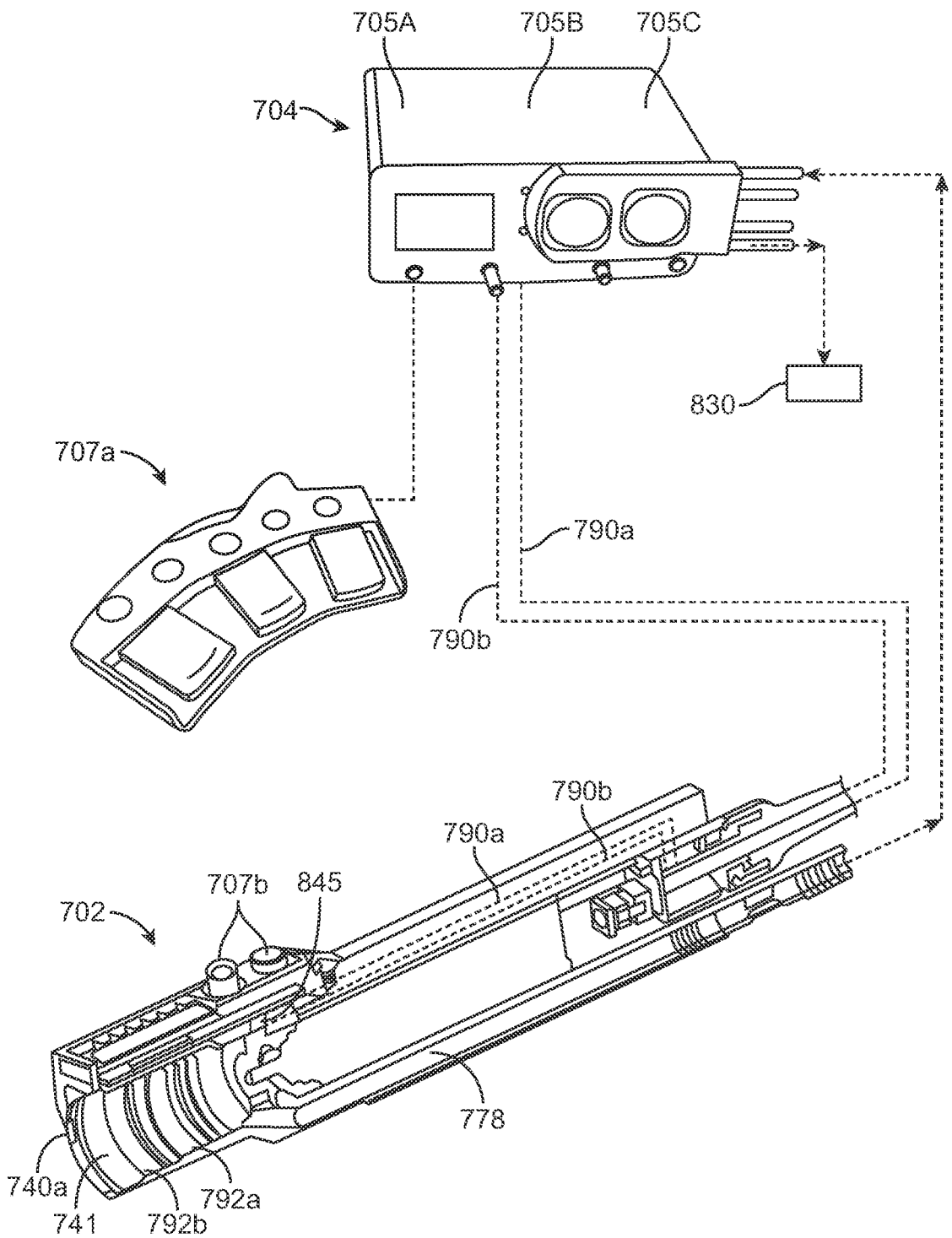
FIG. 23 is a schematic diagram of as RF system that includes a controller console, handpiece with a motor drive and a footswitch.

FIGS. 18-24 illustrate another electrosurgical RF ablation device or probe 700 (FIG. 18) that is adapted for use with a handpiece 702 and motor drive unit 105 (see FIG. 23). In FIG. 23, the console 704 carries RF source 705A and a negative pressure source or outflow pump 705B which can comprise a peristaltic pump and cassette to provide suction though tubing 706 coupled to the handpiece 702 as is known in the art. The console 704 further can carry a controller 705C that operates the motor drive as well as actuation and/or modulation of the RF source 705A and negative pressure source 705B. A footswitch 707a is provided for operation of RF source 705A, negative pressure source 705B and optionally the motor drive. In addition, the motor drive 105, RF source and negative pressure source can be operated by control buttons 707b in the handpiece 702 (FIG. 23). In the RF probe of FIGS. 18 to 22, the motor drive 105 does not rotate a cutting blade or electrode but instead moves or reciprocates an RF electrode axially at a selected reciprocation rate (which may be a high or low reciprocation rate or a single reciprocation) to dynamically ablate, resect and remove tissue.

Figure 18:
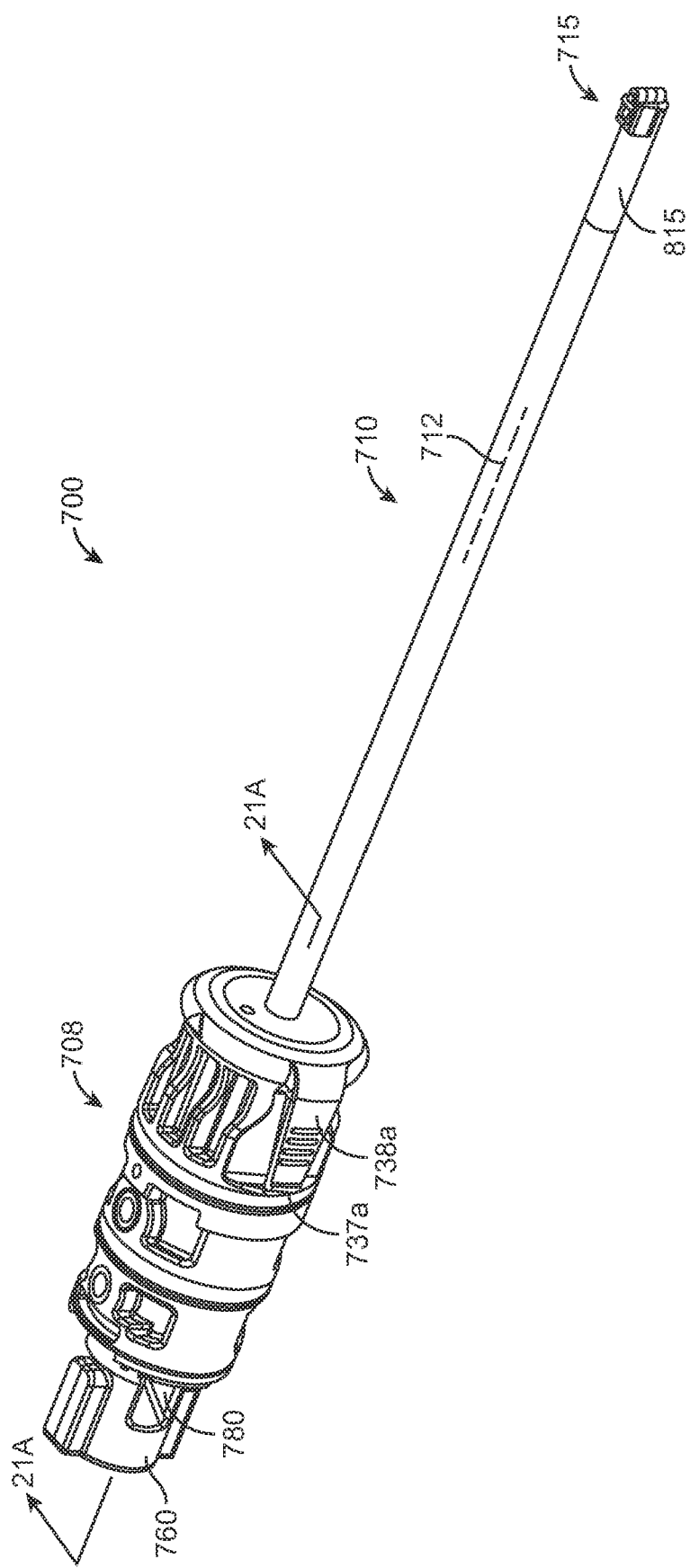
FIG. 18 is a perspective view of a variation of another type of electrosurgical ablation device that can be detachably coupled to a handpiece as shown in FIG. 23.

More in particular, referring to FIG. 18, the detachable RF ablation probe 700 has a proximal housing portion or hub 708 that is coupled to an elongated shaft or extension portion 710 that has an outer diameter ranging from about 2 mm to 7 mm, and in one variation is from 5 mm to 6 mm in diameter. The shaft 710 extends about longitudinal axis 712 to a working end including a housing or body 715 that comprises a dielectric material such as a ceramic as described above, referred to hereinbelow as ceramic housing 715. Referring to FIGS. 18, 19A-19B and 20A-20B, it can be seen that elongated shaft 710 comprises an outer sleeve 716 and an inner sleeve 718. Both sleeves 716 and 718 may comprise a thin wall stainless steel tube or another similar material or composite that is electrically conductive. The outer sleeve 716 has a distal end 719 that is coupled to the ceramic housing 715. An interior channel 720 extends through the housing 715 to a distal channel opening 722 in housing 715. In this variation or embodiment, the channel opening 722 in part faces sideways or laterally in the housing 715 relative to axis 712 and also faces in the distal direction. That is, the distal opening 722 extends over both distal and lateral faces of the ceramic housing 715.

Figure 19A:
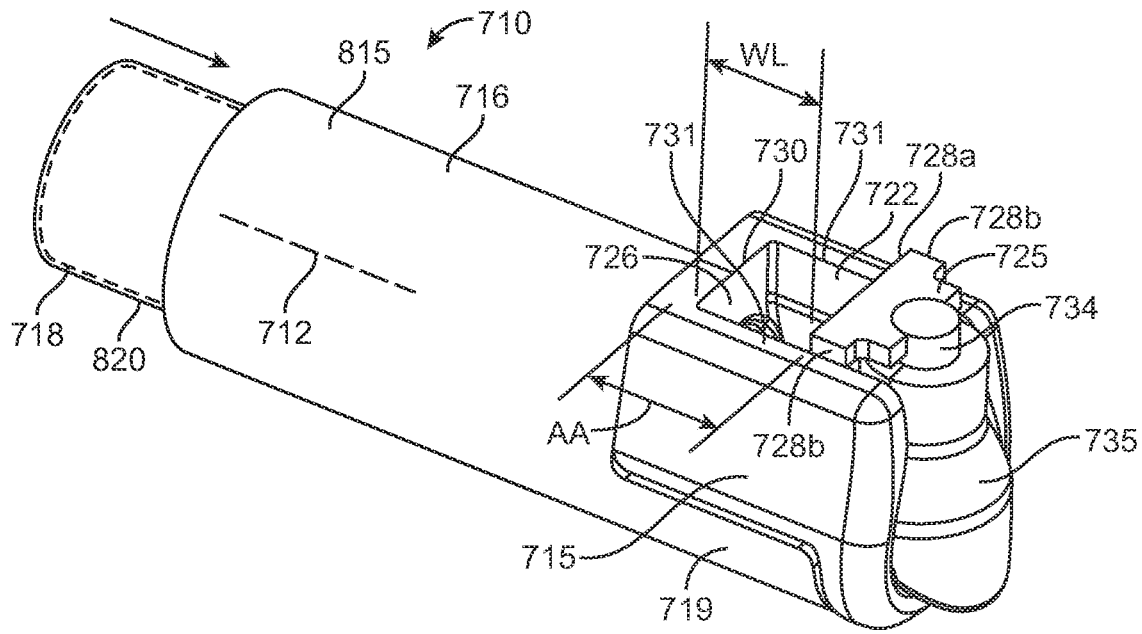
FIG. 19A is a perspective view of the working end and ceramic housing of the device of FIG. 18 showing an electrode in a first position relative to a side-facing window.
Figure 19B:
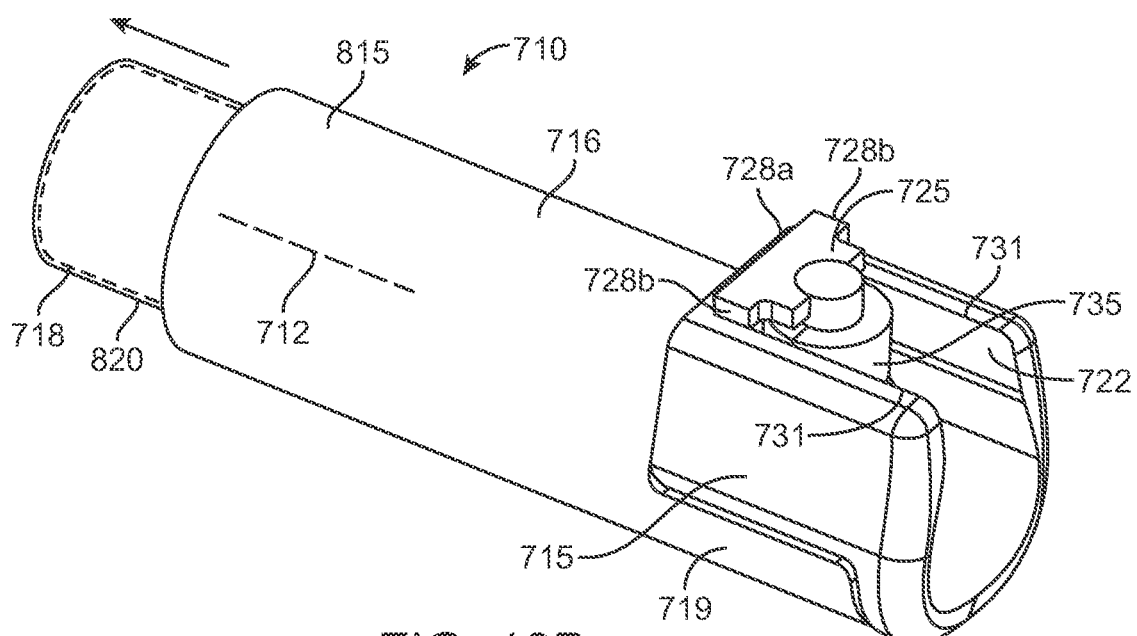
FIG. 19B is a perspective view of the working end of FIG. 19A showing the electrode in a second position relative to the window.
Figure 20A:
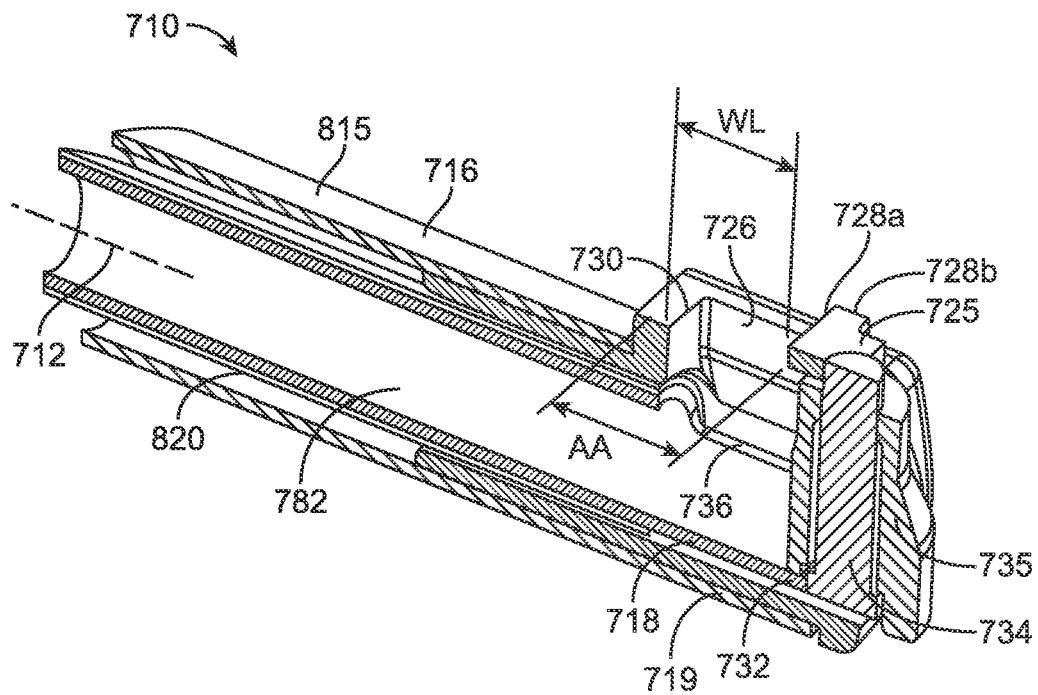
FIG. 20A is a sectional view of the working end and electrode of FIG. 19A.
Figure 20B:
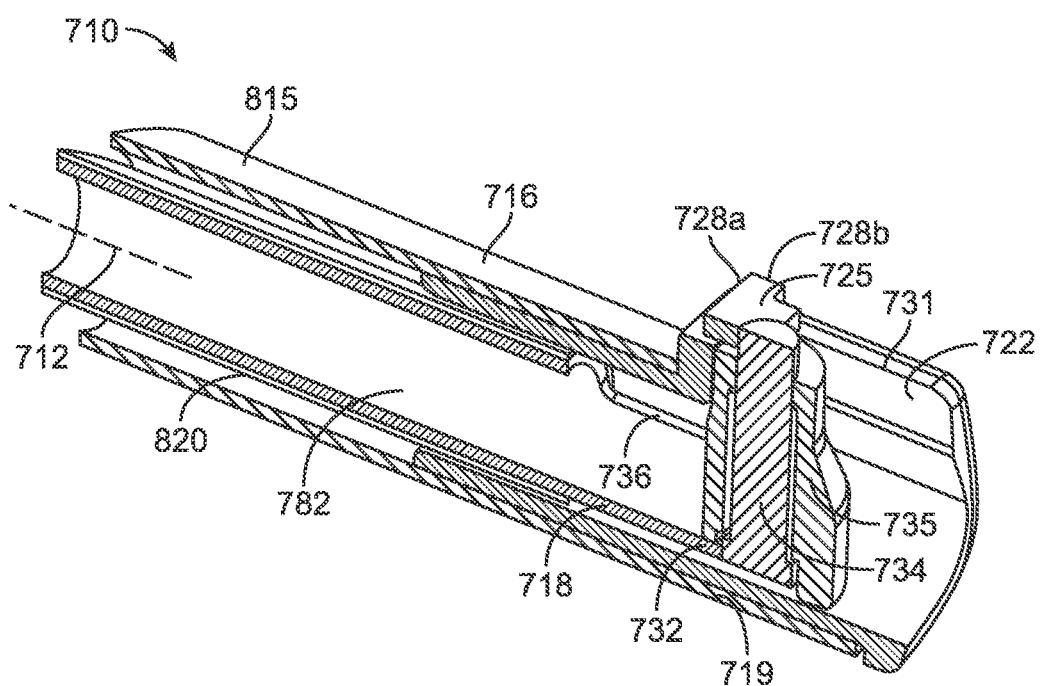
FIG. 20B is a sectional view of the working end and electrode of FIG. 19B.

Referring to FIGS. 19A-19B, a moveable active electrode 725 is configured to extend laterally across a window 726 which has a planar surface and is a section of opening 722 in housing 715. As can be seen in FIGS. 20A-20B, the electrode 725 is carried at the distal end of reciprocating inner sleeve 718. The electrode 725 is adapted to be driven by motor drive unit 105 in handpiece 702 (see FIG. 23) so that proximal-facing edge 728a and side-facing edges 728b of electrode 725 move axially relative to the window 726. FIG. 19A and the corresponding sectional view of FIG. 20A show the inner sleeve 718 and electrode 725 moved by motor drive 105 to an extended or distal axial position relative to window 726. FIGS. 19B and 20B show the inner sleeve 718 and electrode 725 moved by the motor drive to a non-extended or retracted position relative to window 726. In FIGS. 19A and 20A, the window 726 has an open window length WL that can be defined as the dimension between the proximal window edge 730 and the proximal-facing electrode edge 728. The moving electrode 725 moves through a stroke between a distally extended position (FIGS. 19A and 20A) and a distally retracted position (FIGS. 19B and 20B) wherein the electrode edge 728a in the retracted position (FIGS. 19B and 20B) is adapted to extend over the proximal window edge 730 to shear tissue and clean the electrode surface. Likewise, referring to FIGS. 19A-19B, the side-facing edges 728b of electrode 725 extend over the lateral edges 731 of window 726 to shear tissue engaged by suction in the window.

As can be seen in FIGS. 20A-20B, the inner sleeve 718 comprises a thin-wall tube of stainless steel or another conductive material, and is coupled to RF source 705A (FIG. 23) to carry RF current to the electrode 725. The inner sleeve 718 has a distal end 732 that coupled by a weld to a conductive metal rod or element 734 that extends transversely through a dielectric body 735 carried by the inner sleeve. The conductive element 734 is welded to electrode 725 that extends laterally across the window 726. The dielectric body 735 can be a ceramic, polymer or combination thereof and is in part configured to provide an insulator layer around to electrical conductive components (inner sleeve 718 and transverse rod 734) to define the "active electrode" as the limited surface area of electrode 725 which enhances RF energy delivery to the electrode edges 728a and 728b for tissue cutting. The inner sleeve 718 also has side-facing window 736 therein that cooperates or aligns with window 726 in housing 715 to provide suction through the windows 736 and 726 from negative pressure source 705B (see FIGS. 20A and 23) to draw tissue into the window 726.

Now turning to FIGS. 18, 21A-21B, 22 and 23, the mechanism that axially translates the electrode 725 in window 726 is described in more detail. As can be understood from FIGS. 18, 21A and 23, the RF ablation probe 700 can be locked into handpiece 702 of FIG. 22 by inserting tabs 737a and 737b on flex arms 738a and 738b (FIGS. 18 and 21A) into receiving openings 740a and 740b in handpiece 702 (FIG. 23). O-rings 742a and 742b are provided in hub 708 (FIG. 21A-21B) to seal the hub 708 into the receiving channel 741 in the handpiece 702 (FIG. 23).

Referring now to FIGS. 21A-21B, the hub 708 is fixed to outer sleeve 716 that has a bore or channel 720 therein in which the inner sleeve 718 is slidably disposed. A proximal end 744 of inner sleeve 718 has an actuator collar 745 of an electrically conductive material attached thereto with a proximal-facing surface 746 that has a bump or cam surface 747 thereon. The actuator collar 745 is adapted to reciprocate within bore 748 in the hub 708. FIG. 21A shows the actuator collar 745 in an extended position which corresponds to the extended electrode position of FIGS. 19A and 20A. FIG. 21B shows the actuator collar 745 in a non-extended or retracted position which corresponds to the retracted electrode position of FIGS. 19B and 20B.

The actuator collar 745 and hub 708 include slot and key features described further below to allow for axial reciprocation of the sliding actuator collar 745 and inner sleeve 718 while preventing rotation of the collar 745 and sleeve 718. A spring 748 between a distal surface 750 of actuator collar 745 and a proximally facing internal surface 752 of hub 708 urges the sliding actuator collar 745 and the moveable active electrode 725 toward the retracted or proximal-most position as shown in FIGS. 19B, 20B and 21B.

The motor drive 105 of handpiece 702 (FIG. 23) couples to a rotating drive coupling 760 fabricated of a non-conductive material that rotates in hub 708 as shown in FIGS. 18 and 21A-21B. The drive coupling 760 has a distal cam surface 762 that engages the proximal-facing cam surface 747 on the actuator collar 745 so that rotation of drive coupling 760 will reciprocate the sliding actuator collar 745 through a forward and backward stroke AA, as schematically shown in FIGS. 21A-21B. While the cam surfaces 762 and 747 are illustrated schematically as bumps or cams, one of skill in the art will appreciate that the surfaces can be undulating or "wavy" or alternately comprise multiple facets to provide a ratchet-like mechanism wherein rotation of the rotating drive coupling in 360° will reciprocate the sliding actuator collar 745 through a selected length stroke multiple times, for example from 1 to 100 times per rotation of the drive coupling 760. It should also be appreciated that while full and continuous rotation of the rotating coupling 760 will usually be preferred, it would also be possible to rotationally oscillate (periodically reverse the direction of rotation between clockwise and counter-clockwise) the rotating drive coupling 760, for example to control a length of travel of the moveable active electrode 725 in the window 726 where a rotation of less than 360° will result in a shortened length of travel. The stroke of the sliding actuator collar 745 and electrode 725 can be between 0.01 mm and 10 mm, and in one variation is between 0.10 mm and 5 mm. The selected RPM of the motor determines the reciprocation rate, and in one variation a controller 705C can select a motor operating RPM to provide a reciprocation rate between 1 Hz and 1,000 Hz, usually between 1 Hz and 500 Hz. In another variation, the RF ablation probe 700 can be selectively operated in different reciprocation modes (by controller 705C) to provide different reciprocation rates to provide different RF effects when treating tissue. In an additional variation, the length of the electrode stroke can be selected for different modes, wherein the housing 708 can be provided with a slidable adjustment (not shown) to adjust the distance between the cam surfaces 747 and 762 of the sliding collar 745 and rotating coupling 760, respectively.

The RF probe of FIGS. 18-22 also can be operated in different RF modes. As described above, a typical RF mode for dynamic RF ablation reciprocates the electrode 725 at a selected high speed while delivering RF current in a cutting waveform to thereby create a plasma that ablates tissue. In another RF mode, the controller 705C can include an algorithm that stops the reciprocation of electrode 725 in the extended position of FIGS. 19A and 20A and then RF RF current in a coagulation waveform can be delivered to the electrode 725. The operator can then move the stationary electrode over a targeted site for coagulation of tissue. In yet another RF mode, the controller 705C can reciprocate the electrode 725 as at slow rate (e.g., 1 Hz to 500 Hz) while delivering a coagulation waveform to coagulate tissue.

Figure 24:
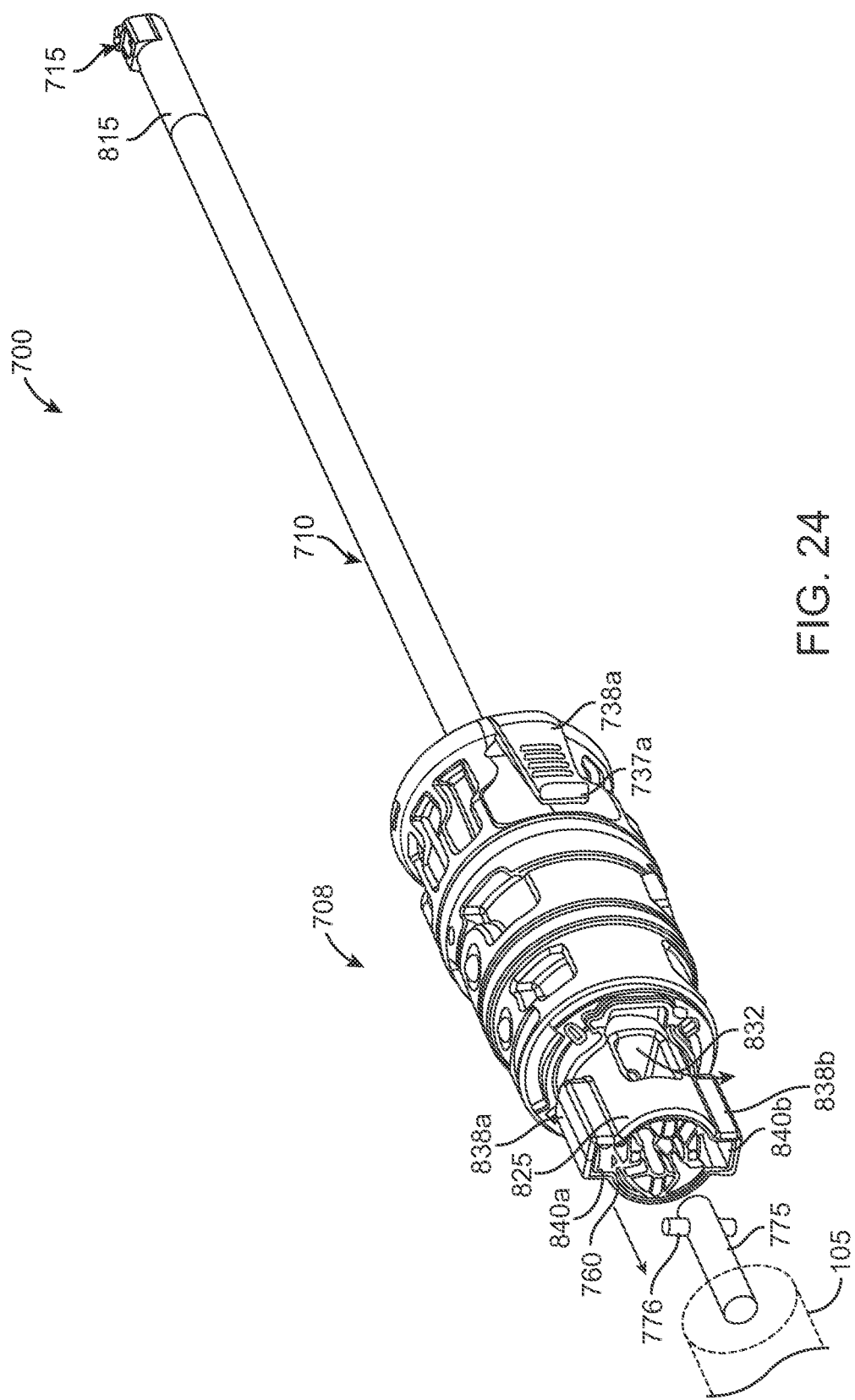
FIG. 24 is a perspective view of the RF probe of FIG. 18 from a different angle showing the drive coupling.

Referring to FIGS. 18, 21A-21B and 24, the rotating coupling 760 is rotationally maintained in hub 708 by a flange 770 that projects into annular groove 772 in the hub 708. The rotating drive coupling 760 is configured for coupling with the drive shaft 775 and transverse pin 776 of motor drive unit 105 as shown in FIG. 24. As in previous embodiments of cutting or shaver assemblies, the negative pressure source 705B is coupled to a passageway 778 in handpiece 702 (FIG. 23) that further communicates through the interior of the handpiece with opening 780 in the drive coupling 760 (see FIGS. 21A-21B) and lumen 782 in inner sleeve 718 to suction tissue into window 726, as can be understood from FIGS. 19A-21B.

FIG. 22 is a longitudinal sectional view of the device hub 708 rotated 90° from the sectional views of FIGS. 21A-21B. FIG. 22 shows the means provided for connecting the RF source 705A to the probe 700 and electrodes. In FIG. 23, first and second electrical leads 790a and 790b are shown schematically extending from RF source 705A through handpiece 702 to electrical contact surfaces 792a and 792b in the receiving channel 741 in the handpiece 702. FIG. 22 shows electrical contacts 795a and 795b in hub 708 as described previously which engage the contact surfaces 792a and 792b in the handpiece. In FIG. 22, the first electrical lead 790a and contact surface 792a delivers RF electrical current to contact 795a in hub 708 which provides at least one ball and spring contact assembly 796 to deliver current to the conductive actuator collar 745 and inner sleeve 718 which is connected to active electrode 725 as described above. It can be understood that the ball and spring contact assembly 796 will allow the actuator collar 745 to reciprocate while engaging the contact assembly 796. In one variation, two ball and spring contact assemblies 796 are provided on opposing sides of the hub 708 for assuring RF current delivery to the actuator collar 745. The inward portions of the two ball and spring contact assemblies 796 also are disposed in axial channels or slots 798a and 798b in the actuator collar 745 and thus function as a slot and key features to allow the actuator collar 745 to reciprocate but not rotate.

Referring again to FIG. 22, the second electrical lead 790b connects to contact surface 792b in handpiece receiving channel 741 which engages the electrical contact 795b in hub 708 of the RF probe 700. It can be seen that an electrical path 802 extends from electrical contact 795b in the hub 708 to outer sleeve 716 wherein and an exposed portion of the outer sleeve 716 comprises a return electrode 815 as shown in FIGS. 18, 19A-19B and 24. It should be appreciated that the outer sleeve 716 can be covered on the inside and outside with a thin electrically insulating cover or coating (not shown) except for the exposed portion which comprises the return electrode 815. The inner sleeve 718 has an insulative exterior layer 820 such as a heat shrink polymer shown in FIGS. 19A-19B and 20A-20B. The insulative exterior layer 820 on the inner sleeve 718 is provided to electrically insulate the inner sleeve 718 from the outer sleeve 716.

In a method of operation, it can be understood that the device can be introduced into a patient's joint that is distended with saline solution together with an endoscope for viewing the working space. Under endoscopic vision, the device working end is oriented to place the electrode 725 against a targeted tissue surface in the patient's joint, and thereafter the RF source 705A and negative pressure source 705B can be actuated contemporaneously to thereby suction tissue into the window 726 at the same time that an RF plasma is formed about the reciprocating electrode 725 which then ablates tissue. The ablated tissue debris is suctioned through the windows 726 and 736 into lumen 782 of inner sleeve 718 to the fluid outflow pathway in the handpiece 702. Ultimately, the tissue debris is carried though the outflow pump system to the collection reservoir 830 (FIG. 23). The device and system can be actuated by the footswitch 707a or a button 707b in the control panel of the handpiece 702 as described previously.

FIG. 24 shows the RF ablation probe or assembly 700 from a different angle where it can be seen that the rotating drive coupling 760 has a bore 822 and at least one slot 824 therein to receive that motor drive shaft 775 and transverse pin 776. In another aspect of the invention, the drive coupling 760 has a smooth exterior surface 825 in 360° around the coupling to provide an enclosure that surrounds and enclosed shaft 775 and transverse pin 776. The exterior surface 825 and 360° enclosure is configured to prevent a fluid outflow indicated by arrow 832 (which carries resected tissue debris) from clogging the system. It can be understood that resected tissue may include elongated, sinewy tissue strips that can wrap around the drive coupling 760 which is spinning at 5,000-15,000 RPM after being suctioned with fluid through opening 780 in the drive coupling 760. Prior art devices typically have a drive shaft and pin arrangement that is exposed which then is susceptible to "catching" tissue debris that may wrap around the coupling and eventually clog the flow pathway. For this reason, the rotating drive coupling 760 has a continuous, smooth exterior surface 825. In an aspect of the present invention, a disposable arthroscopic cutting or ablation device is provided that includes a rotating drive coupling that is adapted to couple to a motor drive shaft in a handpiece, wherein the rotating drive coupling has a continuous 360° enclosing surface that encloses the drive shaft and shaft-engaging features of the drive coupling. In other words, the drive coupling 760 of the invention has motor shaft-engaging features that are within an interior receiving channel of the drive coupling. In another aspect of the invention, referring to FIG. 24, the drive collar 760 of a shaver blade includes enclosing features 838a and 838b that are configured to carry magnets 840a and 840b. Such magnets are adapted to cooperate with at least one Hall sensor 845 in the handpiece 702. The at least one Hall sensor 845 can be used for multiple purposes, including (i) calculating shaft RPM, (ii) stopping shaft rotation and thus electrode 725 and the inner sleeve window 736 in a selected axial position, and (iii) identifying the type of shaver blade out of a catalog of different shaver blades wherein the controller 704 that operates the RF source 705A, negative pressure source 705B and motor controller 705C then can select different operating parameters for different shaver blades based on identifying the blade type.

FIGS. 25-28 illustrate another electrosurgical RF ablation assembly or probe 1000 that is adapted for use with the handle or handpiece 702 and motor drive unit 105 of FIG. 23. In this variation, the motor drive 105 again does not rotate a cutting blade but is configured only for moving a hook shape electrode 1005 (FIG. 25) between a first non-extended position and a second extended position as can be seen in FIGS. 26A and 26B.

Figure 25:
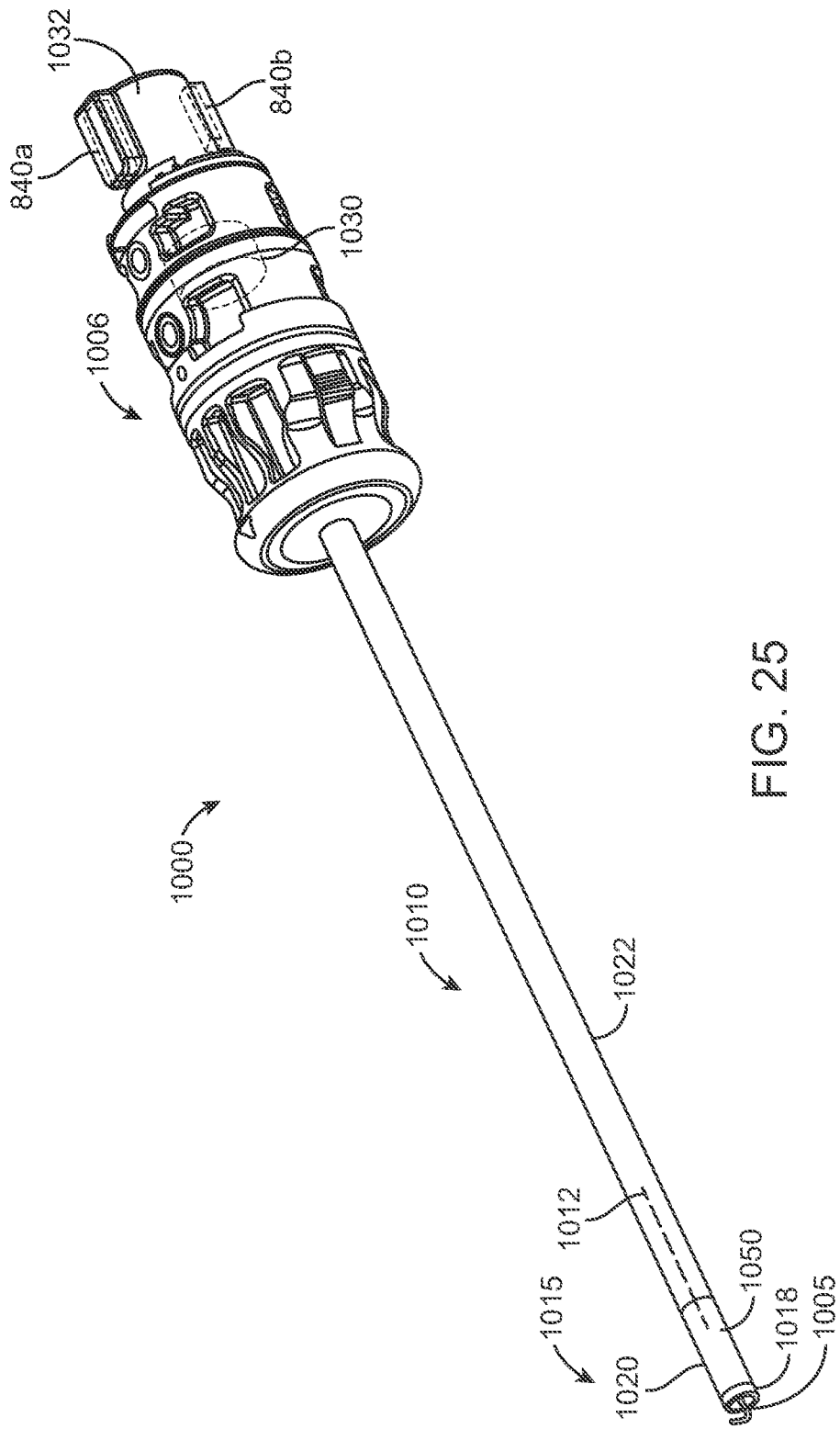
FIG. 25 is a perspective view is a perspective view of a variation of another type of electrosurgical ablation device that can be detachably coupled to a handpiece as shown in FIG. 23, which has a hook type electrode that is moveable with a motor drive.
Figure 26A:
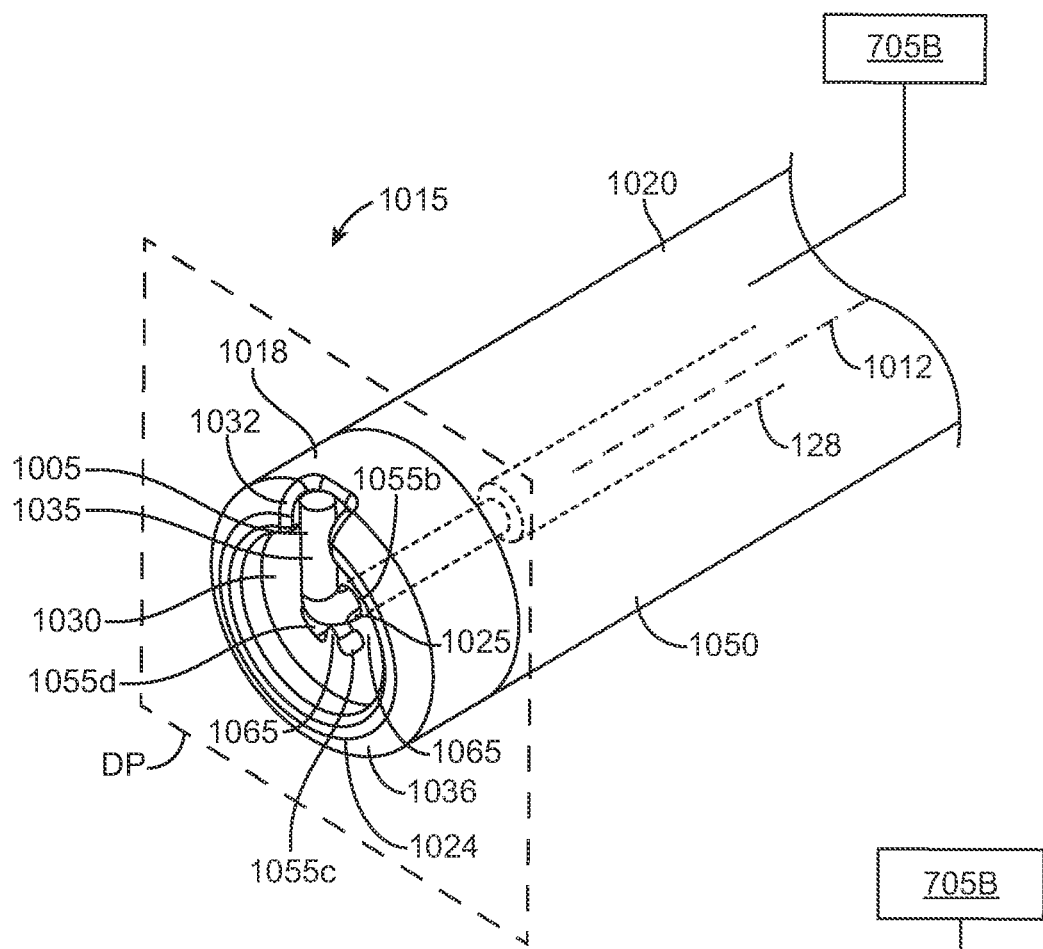
FIG. 26A is a perspective view of the working end of the probe FIG. 25 with the hook electrode in a non-extended position relative to a dielectric distal tip.
Figure 26B:
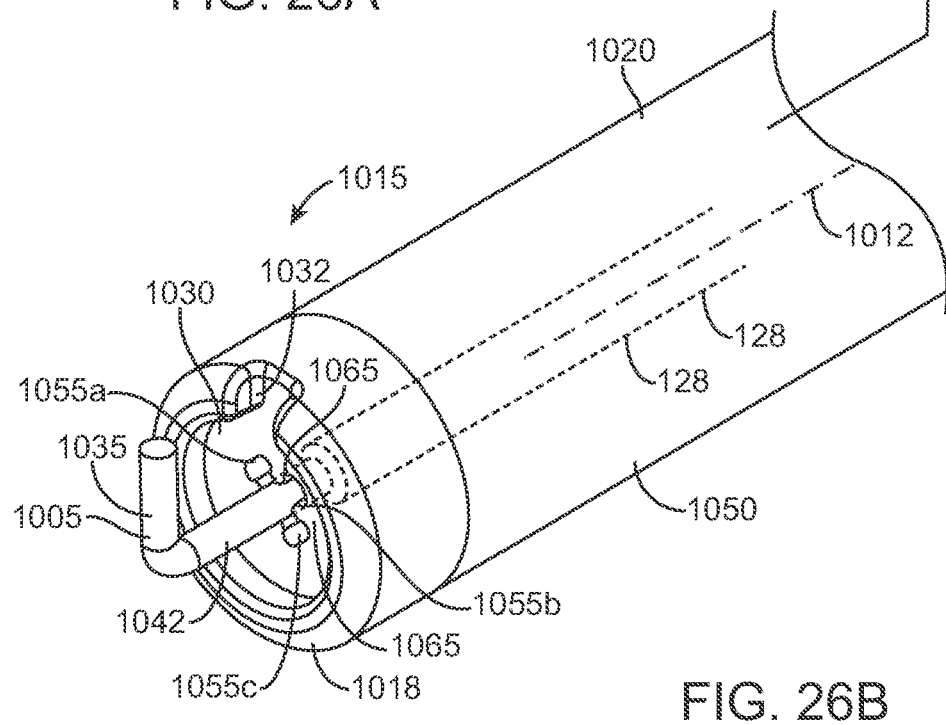
FIG. 26B is a view of the working end of FIG. 26A with the hook electrode in an extended position.
Figure 27:
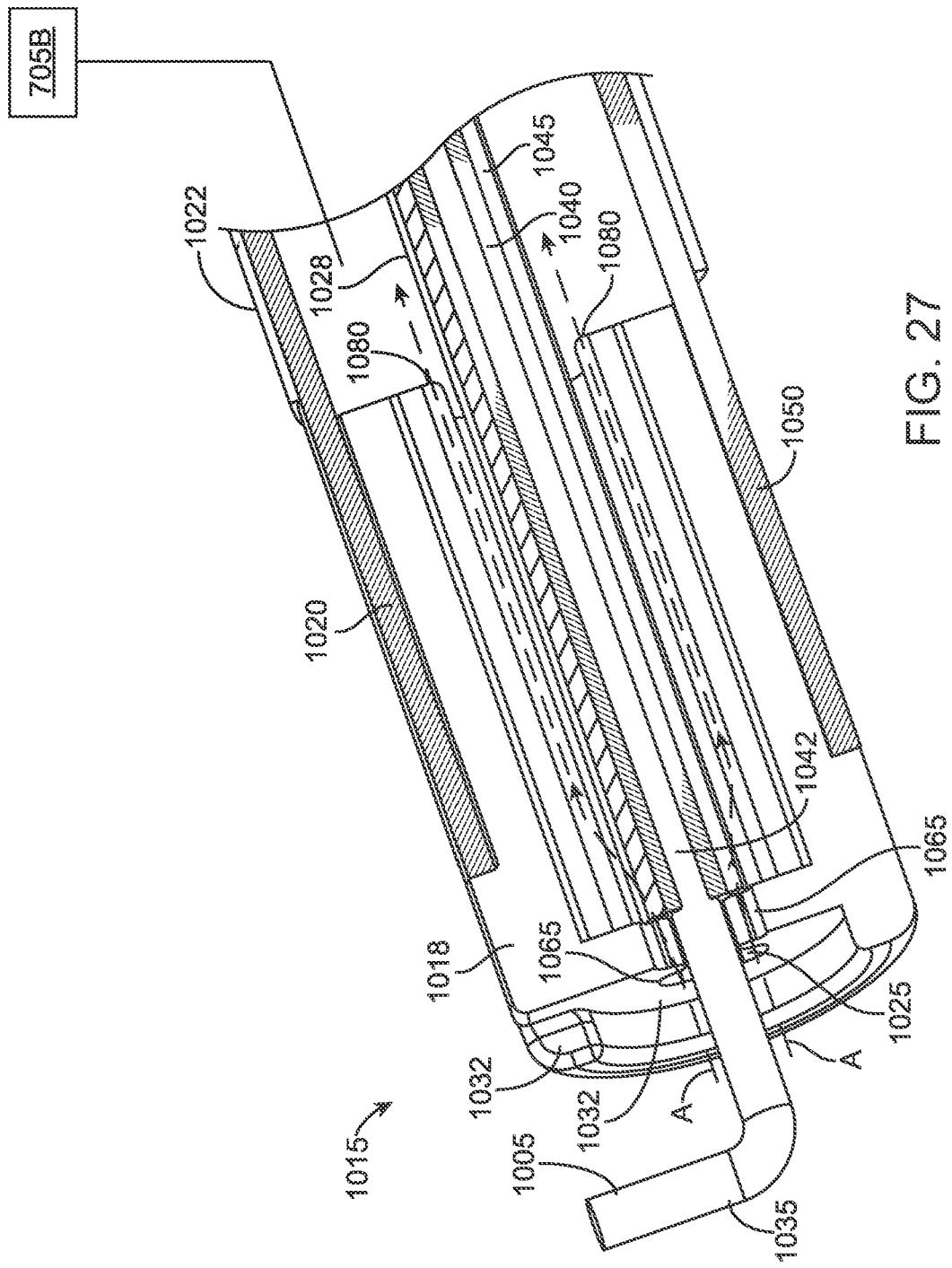
FIG. 27 is a sectional view of the working end of FIG. 26B with the hook electrode in an extended position.

As can be seen in FIG. 25, the RF probe 1000 again has a proximal housing or hub 1006 that is coupled to an elongated extension portion or shaft 1010 with an outer diameter ranging from about 2 mm to 7 mm, and in one variation is 3 mm to 5 mm in diameter. The shaft 1010 extends about longitudinal axis 1012 to a working end 1015 that includes a ceramic or other dielectric tip or body 1018 which can be a ceramic or glass material as described above. Referring to FIGS. 25 and 27, it can be understood that the elongated shaft 1010 includes a thin wall sleeve 1020 having an interior channel or lumen 121 therein and is fabricated of a conductive material such as stainless steel. An optional insulator layer 1022 is disposed around a proximal and medial portion of the sleeve 1020. The ceramic tip or body 1018 is coupled to the distal end of sleeve 1020 by adhesives or other suitable means. In a variation, as shown in FIGS. 26A and 26B, the ceramic body 1018 has a distal surface 1024 the defines a distal plane DP that is flat and orthogonal to the sleeve 1020, i.e., the axis 1012 of the sleeve is angled at 90° relative to plane DP. In another variation, the distal surface 1024 and distal plane DP can be sloped or inclined at an angle between 45° to 90° relative to the axis 1012. Alternatively, such a distal surface can be curved in a concave or convex shape, or in other cases could have combinations of planar and curved segments.

Referring to FIGS. 26A-26B and 27, the moveable hook electrode 1005 extends through opening 1025 in a distal face 1026 of the dielectric tip 1018. An electrode shaft 1028 that extends entirely through sleeve 1020 which is connected to proximal drive mechanism 1030 (FIG. 25) in the interior of hub 1006 for moving the electrode 1005 between the non-extended position of FIG. 26A and the extended position of FIG. 26B. In the fully extended position of electrode 1005 shown is FIG. 26B, the surface of the hook portion of the electrode can extend from 0.05" to 0.50" from the distal surface 1024 of the dielectric tip 1018. As can be seen in FIGS. 26A-26B, the dielectric tip 1018 has a recess 1030 in its distal surface and a notch 1033 to receive the transverse portion 1035 of the electrode 1005 when in the non-extended position of FIG. 26A. Thus, in the configuration shown in FIG. 26A, the distalmost surface of the working end 1015 comprises only the rounded edge 1036 of the dielectric member 1018 which is suited for introduction through an access incision or an introducer sleeve into a treatment site.

In this variation, the drive mechanism that moves the electrode 1005 axially can be the same mechanism as described above in the previous embodiment and shown in FIGS. 21A, 21B and 22. That is, the motor drive 105 in the handpiece 702 detachably couples to a drive coupling 1032 in the hub 1006 and the motor's rotation is converted to linear motion as described previously (FIG. 25). In FIGS. 26A, 26B and 27, it can be seen that interior channel or lumen 121 in sleeve 120 is connected to the negative pressure source 705B for aspirating fluid and tissue debris from a treatment site. FIGS. 21A-22 illustrate the proximal end 1038 of the elongated member 1028 (phantom view) that carries hook electrode 1005 can be coupled to an shortened inner sleeve 718 to allow for fluid outflows indicated at arrows AR through the hub 708.

In the variation shown in FIGS. 26A-26B, the controller 704 (FIG. 23) includes control algorithms that slow down the motor speed and can be adapted to only move the electrode between the non-extended electrode position (FIG. 26A) and the extended electrode position (FIG. 26B). The controller can use the Hall sensor signals as described above to indicate the rotational position of the drive coupling 1032 (FIG. 25), that again carries magnets 840a and 840b wherein control algorithms can determine or confirm the linear position of the electrode 1005. A Hall sensor 845 is shown in FIG. 23 that is proximate the magnets 840a and 840b. A joystick or button 707b on the handpiece 702 (FIG. 23) can be actuated by the physician to move the electrode 1005 between the non-extended and extended electrode positions (FIGS. 26A-26B).

Referring to FIG. 27, it can be seen that the electrode 1005 can comprise a tungsten wire or other similar material, and in one variation, the electrode is a tungsten wire with a diameter of 0.020", although other diameters are suitable depending on the overall dimensions of the device. As can be seen in FIG. 27, the elongated member or electrode shaft portion 1028 comprises a conductive hypotube 1040 with the longitudinal portion 1042 of the electrode 1005 extending into and fixed in the lumen 1044 of hypotube 1040, which is one variation can be a 0.032" OD stainless steel hypotube. The longitudinal portion 1042 of electrode 1005 can be fixed to the hypotube 1040 by crimping, welding, press fitting or other suitable means. FIG. 27 further shows an insulator layer 1045 around the hypotube 1040 which can be a heat-shrink sleeve which is used to electrically insulate the hypotube 1040 (which carries RF current to active electrode 1005) from the outer sleeve 1020 which comprises a return electrode 1050.

Figure 29:
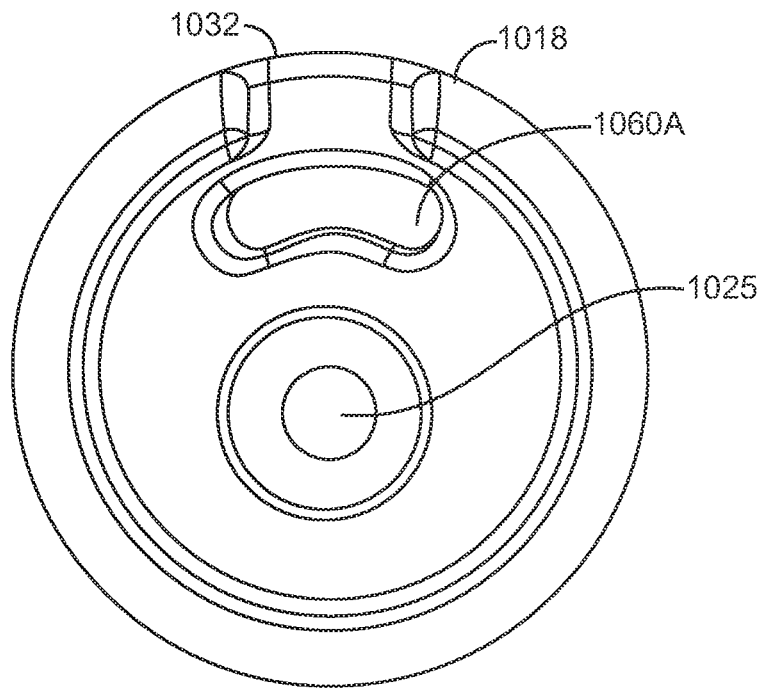
FIG. 29 is an end view of an alternative dielectric tip similar to that of FIGS. 26A-28 with a different configuration of fluid flow channels therein.
Figure 30:
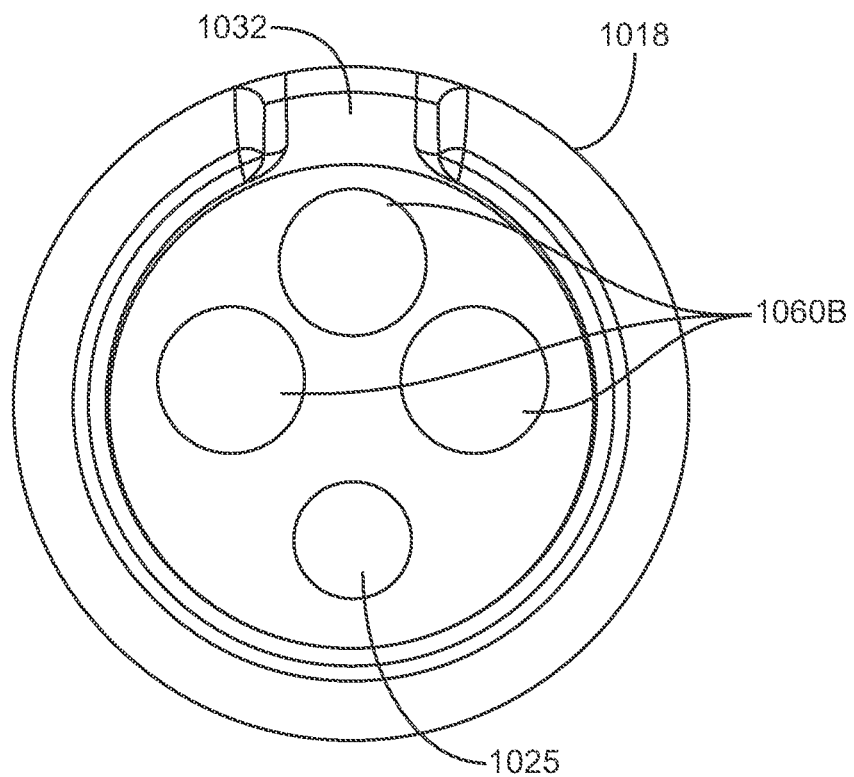
FIG. 30 is an end view of another dielectric tip with a different configuration of fluid flow channels.

In another aspect of the invention, the dielectric distal tip 1018 includes at least one fluid flow passageway therethrough that can comprise the opening 1025 in distal face 1026 which receives the translatable electrode 1005. Such a flow passageway communicates with the negative pressure source 705B (i.e., outflow pump) for removing fluid and tissue debris from a treatment site. In the variation of FIGS. 26A-27, such a flow passageway includes a plurality of channel portions 1055a-1055d projecting radially outwardly from opening 1025 through which the electrode 1005 extends. FIGS. 29-30 illustrate other dielectric tips 1018' and 1018" with other configurations of flow channels 1060A and 1060B that may be used. The electrode shaft may extend through opening 1025 in the center of the dielectric tip 1018 or any off-center position.

Still referring to FIGS. 26A-27, the distal tip 1018 and flow channels 1055a-1055d have certain characteristics and features to perform optimally for removing fluids and tissue debris from a treatment site. In one aspect, the flow channels 1055a-1005d are provided with a sufficient cross-section to allow for fluid flows of at least 50 ml/min, and more often at least 100 ml/min or at least 200 ml/min. As a reference, the negative pressure source or outflow pump 705B used in one variation of the invention is capable of fluid outflows of 1,250 ml/min when there are no restrictions to such fluid outflows.

In order to accommodate the fluid outflows described above, the total cross-sectional area of the flow channels 1055-1055d in the variation shown in FIGS. 26A-27 indicated at CA is least 0.001 square inches and often greater than 0.002 square inches.

Figure 28:
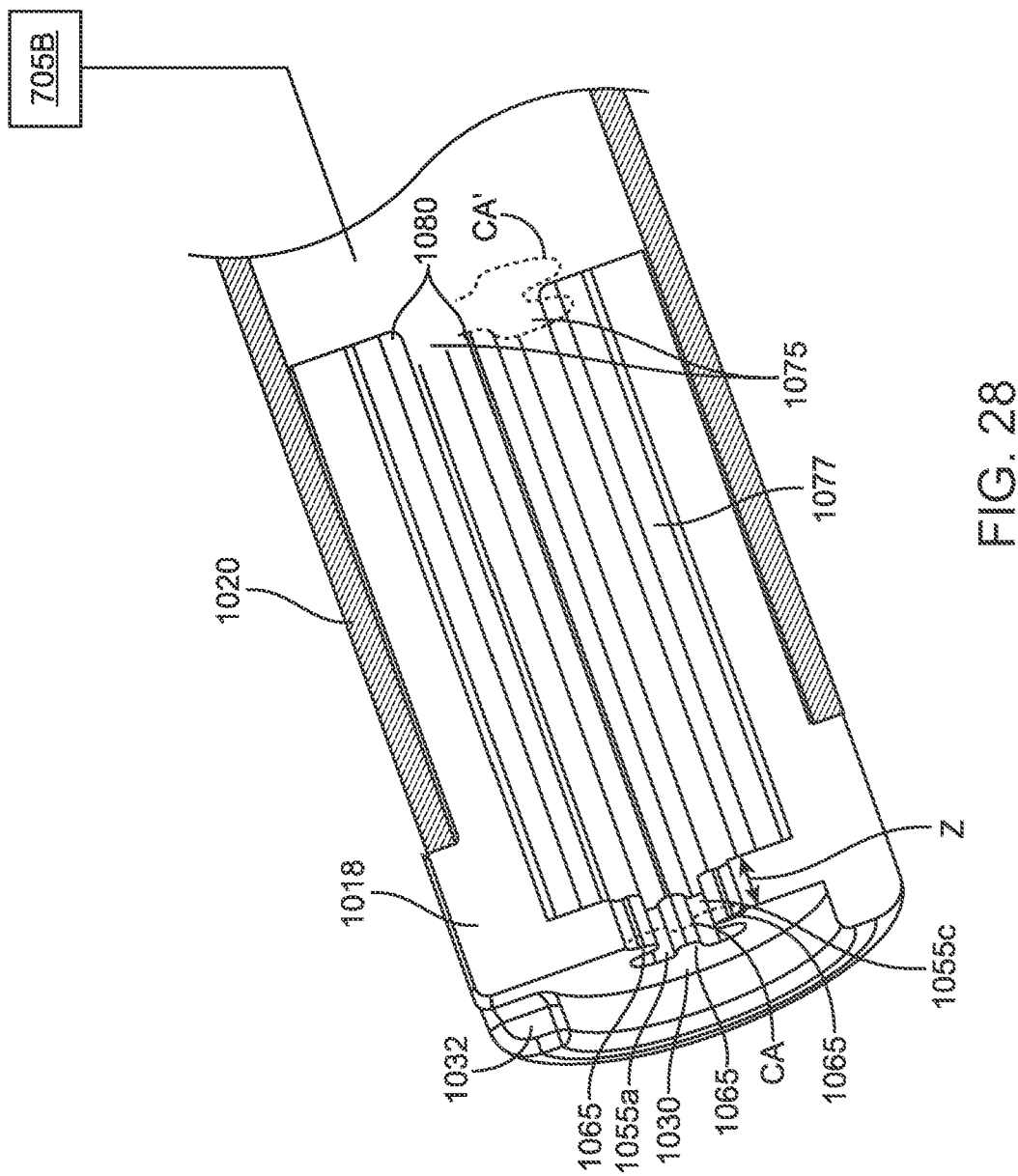
FIG. 28 is a sectional view of the dielectric tip of FIGS. 26A-27 with the hook electrode removed to show the fluid flow channels therein.

In another aspect, referring to FIGS. 27 and 28, the distal tip 1018 is configured with a plurality of longitudinal elements 1065 intermediate the flow channels 1055a-1055d that support the electrode's longitudinal portion 1042. The sectional view of FIG. 28 shows the dielectric tip 1018 without the electrode to better view the longitudinal elements 1065. As shown in FIG. 28, the elements 1065 only contact the electrode longitudinal portion 1042 at a single point or over a short longitudinal dimension Z, for example, less than 2 mm or less than 1 mm. In another aspect, the channels 1055a-1055d transition from the first distal cross-sectional area described above to channels 1075 that have a much larger cross-sectional area in the proximal direction as shown in FIGS. 27 and 28. It has been found that tissue debris can get entangled in elongate flow channels, therefore it is useful to provide such flow channels 1055a-1055d with a cross-section that increases to larger channels 1075 in the proximal direction, that is, in the direction of fluid outflows indicated by arrows AR in FIG. 27.

FIG. 28 is a slightly off-center sectional view of the dielectric tip 1018 without showing the electrode 1005. It can be seen that the cross-sectional area of the channels 1055a-1055d increase in the proximal direction from channel area CA in opening 1025 to channel area CA' in the proximal portion 1077 of the dielectric tip 1018, ignoring the area of the electrode 1005 or shaft 1028. In the variation shown in FIG. 28, it can be seen that more proximal longitudinal rails or features 1080 are dimensioned to support the hypotube 1040 that carries the electrode 1005 as described above.

In a method of use, the single-use probe 1000 of FIGS. 25-26B is assembled with handpiece 702 and the default position of the electrode 1005 is the non-extended or retracted position of FIG. 267A. After assembling the disposable probe 1000 and handpiece, the controller 704 and control algorithms therein can recognize the type of probe, which can be accomplished with Hall sensors that recognize the strength one or more magnets 1072 in hub 708 as shown in the probe variation of FIG. 22. It can be understood that a magnet 1072 in FIG. 22 could be provided with from 2 to 10 different strengths that can be distinguished by a Hall sensor 1075 (FIG. 22), then a corresponding 2 to 10 different probe types can be identified. If two magnets are disposed on opposing sides of the hub 708 as shown in FIG. 22, each having from 2 to 10 different strengths, then the large number of permutations would allow for identification of a larger number of probe types. It should also be appreciated that the rotating magnets 840a and 840b in the drive coupling 760 of FIG. 24 can have different strengths in different probe types and then can be used for acquiring Hall sensor signals for (i) rotating operating parameters as well as being used for (ii) device recognition or probe type identification. The controller 704 is configured with a control algorithm to activate and de-activate the motor drive unit to thereby stop movement of the elongate member or shaft 1028 and electrode 1005 in both the non-extended position (FIG. 26A) and the extended position (FIG. 26B). In one variation, the control algorithm is further configured to deliver RF current to the electrode 1005 only in the electrode-extended position of FIG. 26B. The system further is configured to selectively deliver RF current to the electrode in a cutting waveform or a coagulation waveform.

In a method of use, after the probe 1000 has been recognized and identified, the controller optionally can be configured to actuate the motor drive unit 105 to then move and stop electrode 1005 in the non-extended position of FIG. 26A. Thereafter, the physician can introduce the working end 1015 through an incision into a treatment site in a patient's joint. The physician then can use control button 707b on the handpiece 702 to actuate the motor drive 105 which moves and stops the electrode 1005 in the extended position as shown in FIG. 26B. Thereafter, the physician can engage targeted tissue with the hook electrode 1005 and activate RF energy delivery with either an actuator button 707b on the handpiece 702 or a foot pedal 770a (FIG. 23). The controller 704 can be configured to activate the negative pressure source 705B contemporaneous with the activation of RF delivery. Alternatively, the negative pressure source 705B can be operating at a first aspiration level as the physician prepares to use RF, and then a second increase aspiration level when the RF is activated. Then, with the RF activated, the physician can move or translate the electrode 1005 to cut and ablate tissue. When the treatment is completed, the physician then can use an actuator button or joystick to move the electrode to the non-extended position of FIG. 26A and withdraw the probe 1000 from the treatment site.

The method of using probe 1000 as described above contemplates that electrode 1005 being static in the extended position shown in FIG. 26B with the physician manually translating the hook electrode 1005 against targeted tissue, for example, to cut a ligament. In another method of use, herein called a "dynamic ablation mode", the controller 704 can be provided with control algorithms that rotate the motor drive 105 to rapidly reciprocate the wire electrode 1005 during RF energy delivery to the electrode. It has been found that such a rapid reciprocation of the electrode 1005 over a relatively short stroke can facilitate RF cutting of tissue, which is similar to the RF cutting effect with the probe variations of FIGS. 18-22 above. In one variation, the stroke of electrode 1005 in the dynamic ablation mode can range from 0.01 mm and 5 mm, often being in a range between 0.1 mm and 4 mm. The rate of reciprocation can range from 5 Hz to 500 Hz, and often in the range from 10 Hz to 100 Hz. In another variation, the dynamic ablation method can be use used to rotationally oscillate an electrode which is part of a rotating ceramic cutter as described above. The cutter body and electrode can be moved back and forth from 1° to 20° on each side of a default "stop" position.

In various embodiments, at least one magnet (two magnets 840*a*, 840*b* in FIG. 24) is carried by the rotating coupler 760 as shown in FIG. 24 that couples the moving component of the cutter assembly to the motor shaft 775. Referring to FIG. 23, a Hall sensor 845 is carried by the handpiece 702 in axial alignment with the magnets 840*a*, 840*b* when the cutter assembly 700 is coupled to the handpiece 702. It can be understood that each time the coupler 760 and magnets rotates in 360°, the Hall sensor 845 will sense the magnet's field and can signal the controller of each rotation and then a software tachometer algorithm can calculate and optionally display the RPM of the cutting member.

In another aspect of the invention, the magnets 840*a*, 840*b* and Hall sensor 845 are used in a set of controller algorithms to stop the rotation of the cutting member in a pre-selected rotational default position, for example, with an inner sleeve window exposed in the cut-out opening of outer sleeve, or an electrode positioned relative in an outer member window or opening.

As can be understood from FIGS. 23-24, the controller 704 can always determine in real time the orientation of a window or other feature (e.g., an electrode) of the inner sleeve component, such as coupler 760, relative to the outer sleeve and stationary hub by means of the Hall sensor 845 sensing the rotation of a magnet or magnets 840*a*, 840*b* in the coupler. The controller algorithms can further calculate in real time the rotational angle of the inner sleeve window or electrode away from the magnet/Hall sensor interface since the rotational speed is calculated by the algorithms.

In one variation, the stop mechanism of the invention uses (i) a dynamic braking method and algorithm used to stop the rotation of the inner sleeve or coupler 760 in an initial or potential default position, and (2) in combination with a secondary "checking" algorithm that checks the initial or potential default position attained with the dynamic braking algorithm which is then followed by a slight reverse or forward rotation of the inner sleeve coupler as needed to position the inner sleeve coupler 760 within 0°-5° of the targeted default stop position. Dynamic braking may typically stop the inner sleeve rotation with a variance of up to about 15° of the targeted stop point or default stop position, but this can vary even further when different types of tissue are being cut and impeding rotation of the cutting member, and also depending on whether the physician has completely disengaged the cutting member from the tissue interface when the motor is de-activated. Therefore, dynamic braking alone cannot assure that the initial stop position is within the desired variance from the targeted default position.

As background, the concept of dynamic braking is described in the following literature: https://www.ab.com/support/abdrives/documentation/techpapers/RegenOverview01.pdf and http://literature.ockwelautomation.comidc/goups/literature/documents/wp/drives-wp004-en-p.pdf. Basically, a dynamic braking system provides a chopper transistor on the DC bus of the AC PWM drive that feeds a power resistor that transforms the regenerative electrical energy into heat energy. The heat energy is dissipated into the local environment. This process is generally called "dynamic braking" with the chopper transistor and related control and components called the "chopper module" and the power resistor called the "dynamic brake resistor". The entire assembly of chopper module with dynamic brake resistor is sometimes referred to as the "dynamic brake module". The dynamic brake resistor allows any magnetic energy stored in the parasitic inductance of that circuit to be safely dissipated during turn off of the chopper transistor.

The method is called dynamic braking because the amount of braking torque that can be applied is dynamically changing as the load decelerates. In other words, the braking energy is a function of the kinetic energy in the spinning mass and as it declines, so does the braking capacity. So the faster it is spinning or the more inertia it has, the harder you can apply the brakes to it, but as it slows, you run into the law of diminishing returns and at some point, you actually have no braking power left.

The braking method corresponding to the invention improves upon dynamic braking by adding an additional controller or processor step that calculates the position of magnet relative to Hall sensor after the inner sleeve component has stopped rotating, which can be called an initial stop position which may be the default position or a non-default position. Thereafter, if the inner sleeve component is in a non-default position, the processor instantly can actuate the motor in reverse (or forward) to adjust the rotation direction of inner sleeve component to then stop rotation of the inner sleeve component exactly in the desired default position. It has been found that by using dynamic braking plus the checking algorithm or additional processor step, the inner sleeve component can be positioned within 0° to 5° of the targeted rotational orientation or default position, or at the default orientation with 0° variance. In other words, in one variation, the window or electrode can be precisely positioned within the cut-out opening of the outer sleeve.

Referring to FIG. 22, additional magnets 1072 are shown in phantom view in the shaver blade 708 and can cooperate with another Hall sensor 1075 in handpiece 708 to allow for an additional signal for identification of shaver blades types. For example, with magnets 1072 and Hall sensor 1075 used for blade type identification, the various magnetic strengths may be stratified into 4 to 10 ranges that can be identified by the Hall sensor thus allowing for the identification of 4 to 10 blade types. By using additional magnets (not shown) one of which would pass by Hall sensor 1075 when the blade is inserted into receiver of handpiece 702 (either up or down), a class of 4 to 10 blade types can be identified, and then the signal from the magnets read by the Hall sensor 1075 to identify 4 to 10 sub-types allowing for a wider range of blade identification.

In general, an arthroscopic system comprises a handpiece carrying a motor drive and first and second types of shaver blades each having a proximal hub and a shaft extending about a longitudinal axis to a working end wherein each hub is adapted to be received by a receiver of the handpiece. The hub of the first shaver blade has at least one first magnet with first magnetic parameters, and the hub of the second shaver blade has at least one second magnet having second different magnetic parameters. The handpiece carries a sensor coupled to a controller that is configured to distinguish between the first and second magnetic parameters to identify the shaver blade type received by the handpiece receiver. In this embodiment, the sensor is a Hall sensor and the magnetic parameter can be magnetic field strength or an orientation of poles of the magnets.

In a variation, the arthroscopic system has a controller 704 (FIG. 23) configured to allow or disallow selected operating parameters and programs based on the shaver blade type that is identified. The operating parameters are at least one of rotation of a cutting surface, oscillation of a cutting surface, reciprocation of a cutting surface, speed of rotation, oscillation and reciprocation, RF energy delivery to a cutting surface, and an up/down orientation of a shaver blade relative to the handpiece.

In another aspect of the invention, a disposable arthroscopic shaver blade comprises a proximal hub with a shaft extending about a longitudinal axis to a working end, a first magnet carried by the hub with the poles of said first magnet having a first orientation relative to the longitudinal axis, and a second magnet carried by the hub with the poles of said second magnet having a second relative to the longitudinal axis that differs from said first orientation. The first and second magnets are disposed on opposing sides of the hub, which allows the controller to identify the an up/down orientation of a shaver blade relative to the handpiece, which is needed, for example, to stop movement of the inner sleeve relative to the outer sleeve in a default stop position as described above.

In another aspect of the invention, an arthroscopic system comprises a handpiece carrying a motor, a shaver blade having a proximal hub and a shaft extending about a longitudinal axis to a working end, the hub adapted to be received by a receiver of the handpiece, a magnet carried in a rotating coupling carried by the hub, and a sensor in the handpiece adapted to sense the rotation of the magnet and coupling as a signal from which rotational speed can be calculated by a controller.

In another aspect of the invention, an arthroscopic system comprises a probe having a motor driven inner member that disposed in a passageway in an outer sleeve, a controller operatively configured to control the motor to stop movement of the inner member relative to the outer sleeve in a pre-selected stop or default position, a first dynamic braking algorithm adapted to control the motor to a stop movement of the inner member in a potential default position, and a second algorithm adapted to control the motor to move the inner member from the potential default position to the pre-selected default position if necessary.

In an other aspect, a system comprises a probe coupled to an elongated shaft assembly having a longitudinal axis including first and second members, a motor drive adapted to moves the first member relative to the second member and a processor configured to stop movement of the first member relative to the second member in a selected default position using a sensor that is stationary relative to the second member that senses a magnetic parameter of a magnet that moves in unison with the first member to indicate default and non-default positions. In this variation, the processor is further configured to determine if the first member is in the default position upon pre-selected events, and to move the first member to the default position if the first member is determined to be in a non-default position. In this system, the default position can consist of positioning an electrode carried by the first member in a selected location relative a window in the second member. In another variation, the default position can consist of positioning a window in the first member in a pre-selected location relative a window in the second member.

In another aspect of the invention a predetermined event as described above can be activation of the electrode, or actuation of the negative pressure source in communication with the window in the first member. In another aspect, the predetermined event can be a time interval. For example, the time interval can be between 0.1 ms and 10 seconds, or between 1 ms and 5 seconds, so that the system is effectively checking the inner sleeve position constantly during use.

In another aspect, the processor can be further configured to modulate a treatment parameter in response to determining that the first member is in a non-default position. As an example, the processor can be configured to modulate or terminate activation of the electrode or modulate or terminate actuation of the negative pressure source. Further, the processor can be configured to move the first member to the default position following any of the steps of modulating or terminating treatment modes just described above. Still further, the processor can be configured to re-activate the electrode or re-actuate the negative pressure source after moving the first member to the default position. This method of operating the system is important because, for example, the physician may activate RF energy delivery while moving the working end over tissue which may bump the inner sleeve out of the default position. If the electrode has been inadvertently moved from the default position, the RF current could arc to outer sleeve when it function as a return electrode which would be undesirable.

In general, the default position consists of positioning the electrode or an opening in the first member in a center region of the window in the second member, or at a position away from edges of the window in the second member. In some variations, the default position places the electrode at a selected rotational angle relative to the axis of the cutter assembly and the window in the second member. In other variations, the default position consists of positioning the electrode at a selected axial position relative to the axis or an opening in the second member.

In another aspect, the system includes a handpiece carrying a motor drive detachably coupled to disposable tool with a first member disposed within a hub fixed to a second member, wherein the motor drive is adapted to move the first member relative to the hub and second member, a first sensor in the handpiece adapted to sense a magnetic parameter of at least one magnet in the hub to indicate a first orientation or a second orientation of the hub relative to the handpiece, a second sensor in the handpiece adapted to sense a magnetic parameter of at least one magnet in the first member to indicate a position of the first member relative to the second member, and a processor configured (i) to determine if the hub is in said first orientation or said second orientation using the first sensor and (ii) to stop movement of the first member relative to the second member in a pre-selected default position using the second sensor.

In another aspect, the system comprises a handpiece with a motor drive having a shaft, a shaver blade having a hub coupled to an elongated sleeve assembly comprising an outer sleeve fixed to the hub and a rotatable inner sleeve, the hub adapted to be detachably received by a receiver of the handpiece, a drive coupling connected to the inner sleeve configured to be detachably coupled to the motor shaft, a first sensor in the handpiece adapted to sense a magnetic parameter of at least one magnet carried in the hub to indicate a first orientation or a second orientation of the hub relative to the handpiece, and a second sensor in the handpiece adapted to sense a magnetic parameter of at least one magnet in the drive coupling to indicate a position of the inner sleeve relative to the outer sleeve.

In another aspect, the system comprises a handpiece carrying a motor drive having a shaft, a shaver blade having a hub coupled to an elongated sleeve assembly extending along a central axis, the sleeve assembly comprising an outer sleeve fixed to the hub and a rotatable inner sleeve, a drive coupling connected to the inner sleeve configured to be detachably coupled to the motor shaft, and first and second magnets carried in opposing surfaces of the drive coupling wherein the North and South poles of each magnet are oriented differently relative to said central axis.

In another aspect of the invention, the fluid management system pumps and controller 704 (FIG. 23) may need to be calibrated during set up prior to use in a patient. In use, the system has an inflow pump coupled to inflow line for delivering a distention fluid from fluid source through an access cannula to a working space. Further, the controller has a pressure sensor coupled to the inflow line that is configured to sense fluid pressure in the working space during a procedure, wherein the sensor is adapted to send signals to a controller to modulate inflows to maintain a set fluid pressure in the working space. As can be easily understood, the pressure sensor will read back pressure in the inflow line and cannula along with the actual fluid pressure in the working space. Typically, each physician may use a different size cannula, and further, there may be an endoscope introduced through the cannula so there cannot be a predetermined back pressure that can be use by the controller. To determine the back pressure for each potentially unique situation, a method of operating the system includes the steps of actuating the inflow pump to provide a flow through the inflow line and cannula prior to introduction of the cannula into the working space to thereby determine a inflow line and cannula to determine a back pressure value, and then calibrating the control system with said back pressure value to allow for calculation of actual fluid pressure in the working space during a procedure. Thereafter, the method of use included introducing the cannula into the working space and operating the inflow pump to maintain a selected fluid set pressure in the working space based on signals from said pressure sensor as adjusted by the back pressure value.

Figure 31:
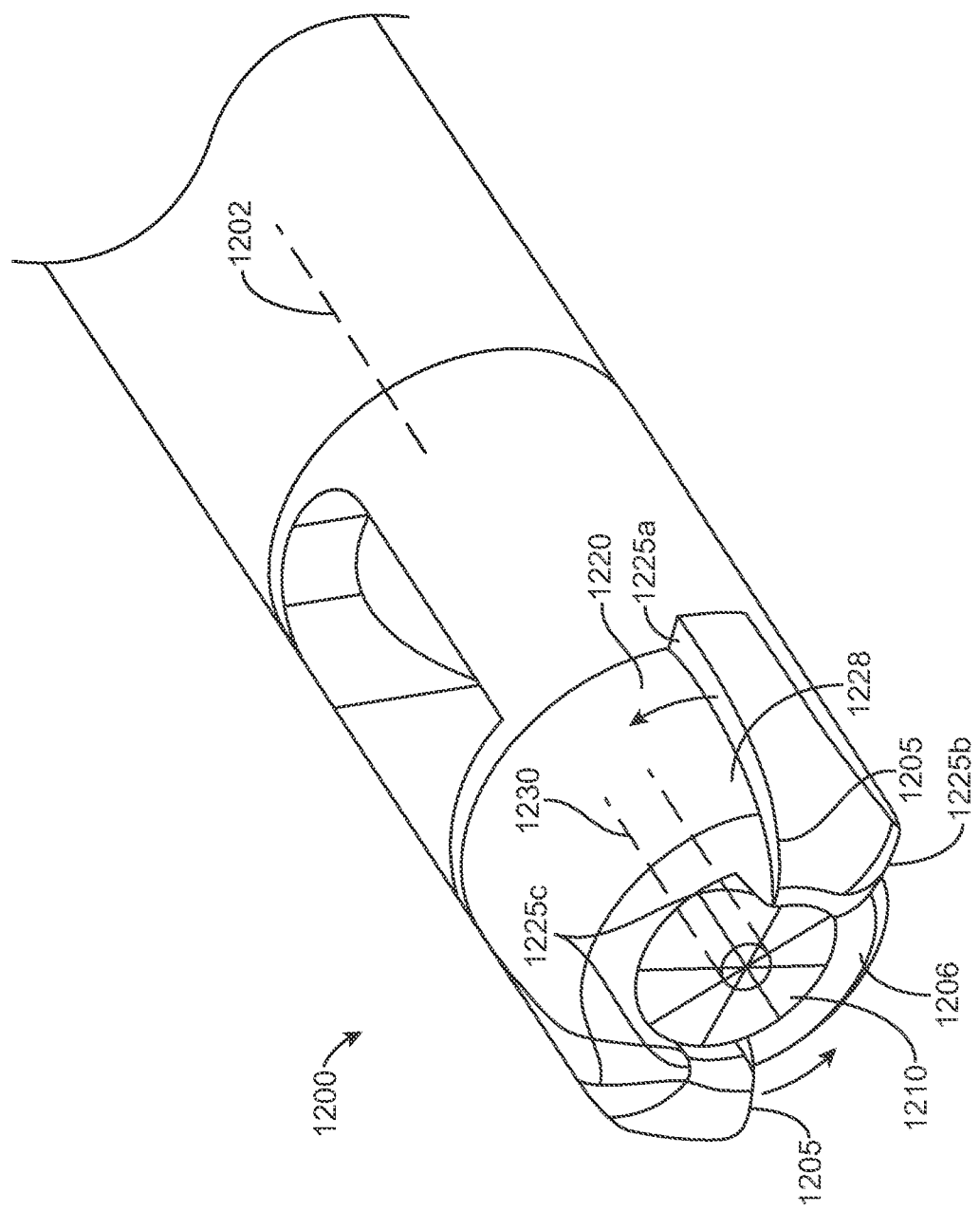
FIG. 31 is a perspective view of another ceramic cutter with distal cutting edges extending around a distal nose of the cutter into a recess or concavity for drilling in bone.
Figure 32:
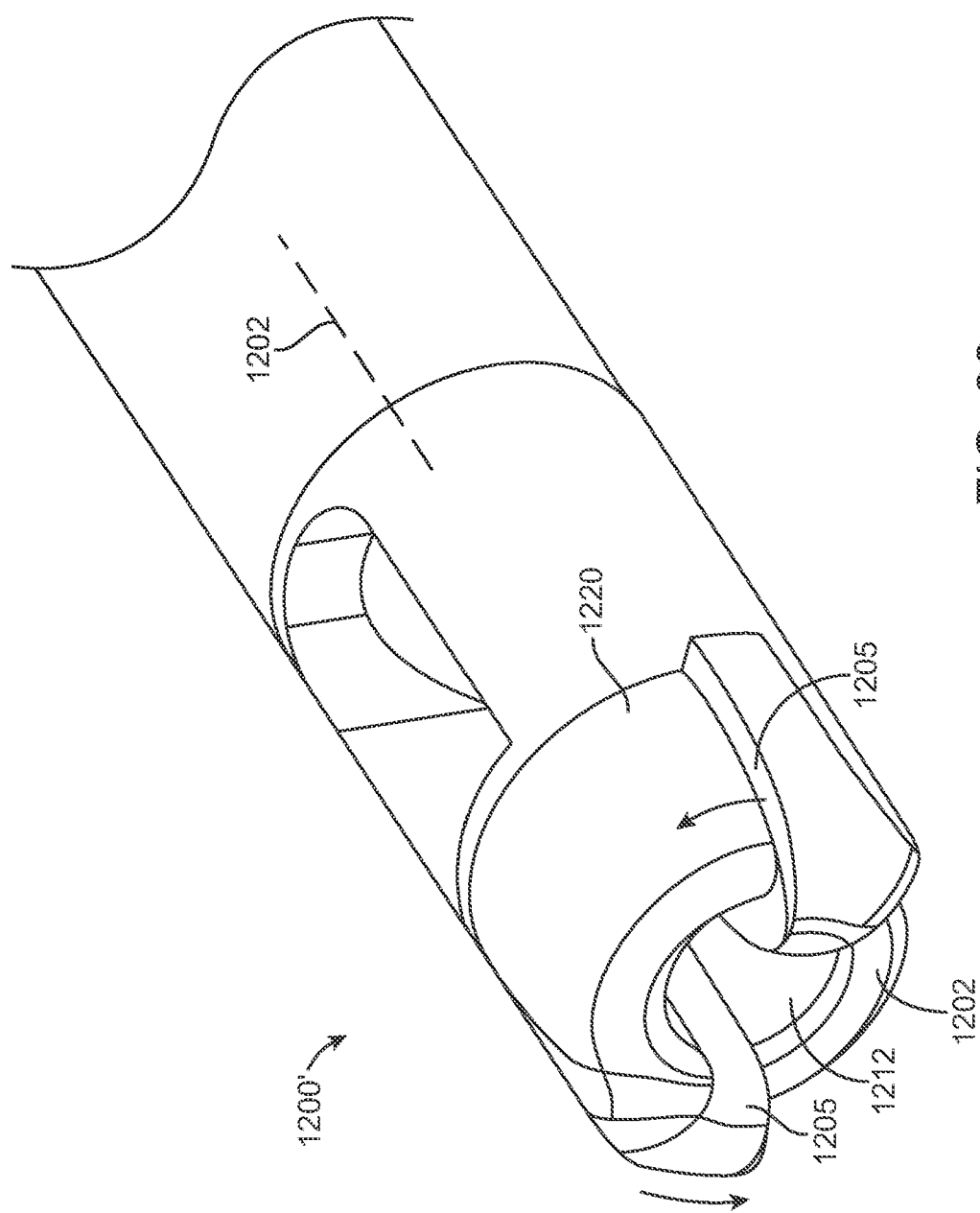
FIG. 32 is a perspective view of a ceramic cutter similar to that of FIG. 31 with cutting edges extending around a nose of the cutter into an axial passageway therein.

Now referring to FIGS. 31-32, another variation of a ceramic cutter 1200 with axis 1202 is shown (without outer sleeve) which has cutting edges 1205 that extend around a distal nose 1206 of the cutter into a recess or concavity 1210 of the cutter body wherein such features allow for drilling into bone. FIG. 32 shows a variation of cutter 1200' in which the cutting edges 1205 extend into an axial passageway 1212 that communicates with a negative pressure source.

In general, the cutter body 1200 of FIG. 31 has a central axis 1202 and a plurality of cutting edges 1205 separated by flutes 1220 wherein the cutting edges have cutting edge portions 1225*a* that (i) face radially outward from an outer surface 1228 of the cutter body, (ii) edge portions 1225*b* that face distally from a distal nose 1206 of the body, and edge portions 1225*c* that face radially inward toward said central axis 1202 in a distal recess 1210 in the cutter body. The distal recess can have an axial depth of at least 1 mm or at least 2 mm. In another variation, the distal recess 1206 transitions to a bore 1230 (phantom view) extending through the cutter body. The cutter body can be formed from a wear-resistant ceramic material as described previously. The cutting edges 1205 can be non-helical and aligned with said central axis 1202 to facilitate ceramic injection molding of the cutter body. Alternatively, such cutting edged 1205 can be helical. The number of cutting edges can range from 2 to 100. In other variations, the cutter body can carry an electrode in a surface of the cutter body as described previously.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A surgical method of treatment, comprising:
    operating a medical system to treat tissue in a working space in a patient, the medical system comprising:
        a handpiece with a motor drive and a first sensor;
        a probe with a proximal hub and an elongated shaft assembly that extends about a longitudinal axis to a working end of the probe, the elongated shaft assembly including a first elongated member longitudinally received within a second elongated member, the proximal hub detachably coupled to the handpiece such that the motor drive is coupled to a rotating drive coupling in the proximal hub, the rotating drive coupling coupled to a proximal portion of the first elongated member and including a first magnet coupled thereto to rotate with the rotating drive coupling, wherein the first sensor in the handpiece is configured to sense rotation of the first magnet as the rotating drive coupling rotates for generating signals about the rotational position of the rotating drive coupling in the proximal hub, and wherein a distal portion of the first elongated member includes an electrode thereon and is actuatable to at least a first default position relative to the second elongated member at the working end of the probe; and
        a controller configured to receive signals from the first sensor about the rotational position of the rotating drive coupling in the proximal hub,
    wherein said operating comprises:
        applying a first electrical current to the electrode with the working end of the probe in the working space in the patient and with the distal portion of the first elongated member in the first default position, wherein, during said applying, the controller receives signals from the first sensor about the rotational position of the rotating drive coupling in the proximal hub, and while receiving said signals, repeatedly checks at a predetermined time interval of between 0.1 ms and 10 seconds to determine if the distal portion of the first elongated member has inadvertently migrated from the first default position.

2. The surgical method of claim 1, wherein the predetermined time interval is between 1 ms and 5 seconds.

3. The surgical method of claim 1, wherein the controller is programmed to terminate the first electrical current if the controller has determined that the distal portion of the first elongated member has inadvertently migrated from the first default position during said applying.

4. The surgical method of claim 3, wherein the controller is programmed to activate the motor drive to rotate the rotating drive coupling about the longitudinal axis and thereby actuate the distal portion of the first elongated member relative to the second elongated member at the working end of the probe to return the distal portion of the first elongated member to the first default position following termination of the first electrical current due to the controller determining that the distal portion of the first elongated member has inadvertently migrated from the first default position during said applying.

5. The surgical method of claim 4, wherein the controller is programmed to re-apply the first electrical current to the electrode with the distal portion of the first elongated member in the first default position following returning the distal portion of the first elongated member to the first default position following termination of the first electrical current due to the controller determining that the distal portion of the first elongated member has inadvertently migrated from the first default position during said applying.

6. The surgical method of claim 1, wherein the controller is programmed to modulate the first electrical current to a modulated condition if the controller has determined that the distal portion of the first elongated member has inadvertently migrated from the first default position during said applying.

7. The surgical method of claim 6, wherein the controller is programmed to activate the motor drive to rotate the rotating drive coupling about the longitudinal axis and thereby actuate the distal portion of the first elongated member relative to the second elongated member at the working end of the probe to return the distal portion of the first elongated member to the first default position following modulation of the first electrical current to the modulated condition due to the controller determining that the distal portion of the first elongated member has inadvertently migrated from the first default position during said applying.

8. The surgical method of claim 7, wherein the controller is programmed to re-apply the first electrical current to the electrode with the distal portion of the first elongated member in the first default position following returning the distal portion of the first elongated member to the first default position following modulation of the first electrical current to the modulated condition due to the controller determining that the distal portion of the first elongated member has inadvertently migrated from the first default position during said applying.

9. The surgical method of claim 1, wherein the controller is programmed to activate the motor drive to rotate the rotating drive coupling about the longitudinal axis and thereby actuate the distal portion of the first elongated member relative to the second elongated member at the working end of the probe to return the distal portion of the first elongated member to the first default position if the controller has determined that the distal portion of the first elongated member has inadvertently migrated from the first default position during said applying.

10. The surgical method of claim 1, wherein in the first default position the electrode on the distal portion of the first elongated member is positioned in an outer window in the second elongated member.

11. The surgical method of claim 10, wherein in the first default position the electrode on the distal portion of the first elongated member is positioned in a center region of the outer window in the second elongated member.

12. The surgical method of claim 10, wherein in the first default position the electrode on the distal portion of the first elongated member is positioned away from edges of the outer window in the second elongated member.

13. The surgical method of claim 10, wherein in the first default position the electrode on the distal portion of the first elongated member is positioned at a selected rotational angle relative to said longitudinal axis and the outer window in the second elongated member.

14. The surgical method of claim 1, wherein the first elongated member comprises an inner sleeve and the second elongated member comprises an outer sleeve.

15. The surgical method of claim 14, wherein the inner sleeve provides a lumen in the elongated shaft assembly.

16. The surgical method of claim 1, wherein the rotating drive coupling is rotatable about the longitudinal axis to cause the distal portion of the first elongated member to rotate relative to the second elongated member at the working end of the probe.

17. The surgical method of claim 1, wherein the rotating drive coupling is rotatable about the longitudinal axis to cause the distal portion of the first elongated member to reciprocate relative to the second elongated member at the working end of the probe.

18. The surgical method of claim 1, wherein the medical system further comprises a negative pressure source in communication with a lumen in the elongated shaft assembly, and wherein said operating further comprises actuating the negative pressure source during said applying.

19. The surgical method of claim 18, wherein the controller is programmed to terminate actuation of the negative pressure source if the controller has determined that the distal portion of the first elongated member has inadvertently migrated from the first default position during said applying.

20. The surgical method of claim 18, wherein the controller is programmed to modulate actuation of the negative pressure source if the controller has determined that the distal portion of the first elongated member has inadvertently migrated from the first default position during said applying.

21. The surgical method of claim 1, wherein in the first default position the electrode on the distal portion of the first elongated member is positioned at a selected axial position relative to said longitudinal axis and an opening in the second elongated member.

* * * * *